(12) United States Patent
Cerundolo et al.

(10) Patent No.: US 10,039,715 B2
(45) Date of Patent: Aug. 7, 2018

(54) LIPOSOMAL FORMULATION OF NONGLYCOSIDIC CERAMIDES AND USES THEREOF

(71) Applicant: LUDWIG INSTITUTE FOR CANCER RESEARCH LTD., New York, NY (US)

(72) Inventors: Vincenzo Cerundolo, Oxford (GB); Simon Eastman, Delta (CA)

(73) Assignee: LUDWIG INSTITUTE FOR CANCER RESEARCH LTD., New York, NY (US)

( * ) Notice: Subject to any disclaimer, the term of this patent is extended or adjusted under 35 U.S.C. 154(b) by 0 days.

(21) Appl. No.: 15/253,307

(22) Filed: Aug. 31, 2016

(65) Prior Publication Data

US 2017/0105936 A1    Apr. 20, 2017

Related U.S. Application Data

(63) Continuation of application No. 13/993,946, filed as application No. PCT/US2011/066840 on Dec. 22, 2011, now abandoned.

(60) Provisional application No. 61/442,755, filed on Feb. 14, 2011, provisional application No. 61/426,725, filed on Dec. 23, 2010.

(51) Int. Cl.
*A61K 9/127* (2006.01)
*A61K 39/00* (2006.01)
*A61K 45/06* (2006.01)

(52) U.S. Cl.
CPC .......... *A61K 9/1272* (2013.01); *A61K 9/1277* (2013.01); *A61K 39/0011* (2013.01); *A61K 45/06* (2013.01); *A61K 2039/55555* (2013.01)

(58) Field of Classification Search
CPC ..................................................... A61K 9/127
See application file for complete search history.

(56) References Cited

U.S. PATENT DOCUMENTS

| | | | |
|---|---|---|---|
| 5,008,050 A | 4/1991 | Cullis et al. | |
| 5,376,380 A * | 12/1994 | Kikuchi | A61K 9/1277 264/4.1 |

(Continued)

FOREIGN PATENT DOCUMENTS

| | | |
|---|---|---|
| WO | WO-89/08846 A1 | 9/1989 |
| WO | WO-00/20581 A1 | 4/2000 |

(Continued)

OTHER PUBLICATIONS

Adlakha-Hutcheon et al., Controlled destabilization of a liposomal drug delivery system enhances mitoxantrone antitumor activity, Nat. Biotechnol., 17:775-9 (1999).

(Continued)

*Primary Examiner* — Gollamudi Kishore
(74) *Attorney, Agent, or Firm* — Marshall, Gerstein & Borun LLP

(57) ABSTRACT

The invention provides liposomes containing nonglycosidic ceramides within their bilayers, and compositions thereof. These liposomes activate murine iNKT cells and induce dendritic cell (DC) maturation, both in vitro and in vivo at an efficacy that is comparable to their corresponding soluble nonglycosidic ceramides. Also provided are methods for treating diseases using the liposomes and compositions of the invention.

21 Claims, 12 Drawing Sheets

(56) References Cited

U.S. PATENT DOCUMENTS

| | | | |
|---|---|---|---|
| 5,543,152 | A | 8/1996 | Webb et al. |
| 5,589,178 | A | 12/1996 | Aubert et al. |
| 5,705,385 | A | 1/1998 | Bally et al. |
| 5,830,481 | A | 11/1998 | Cauwet-Martin et al. |
| 6,077,972 | A | 6/2000 | Tuloup et al. |
| 7,060,291 | B1 | 6/2006 | Meers et al. |
| 7,842,676 | B2 | 11/2010 | Janoff et al. |
| 7,850,990 | B2 | 12/2010 | Tardi et al. |
| 8,835,613 | B2 | 9/2014 | Berzofsky et al. |
| 2006/0094661 | A1 | 5/2006 | Liu et al. |
| 2009/0191259 | A1 | 7/2009 | Li et al. |
| 2009/0239813 | A1 | 9/2009 | Cerundolo et al. |
| 2010/0284965 | A1 | 11/2010 | Fahmy et al. |
| 2014/0050780 | A1 | 2/2014 | Cerundolo et al. |

FOREIGN PATENT DOCUMENTS

| | | |
|---|---|---|
| WO | WO-2007/050668 A1 | 5/2007 |
| WO | WO-2009/133378 A2 | 11/2009 |
| WO | WO-2010/055340 A1 | 5/2010 |

OTHER PUBLICATIONS

Barral et al., B cell receptor-mediated uptake of CD1d-restricted antigen augments antibody responses by recruiting invariant NKT cell help in vivo, Proc. Natl. Acad. Sci. USA, 105(24):8345-50 (2008).

Barral et al., CD169(+) macrophages present lipid antigens to mediate early activation of iNKT cells in lymph nodes, Nat. Immunol., 11(4):303-12 (2010).

Benoit et al., Regulation of airway eosinophil and neutrophil infiltration by alpha-galactosylceramide in a mouse model for respiratory syncytial virus (RSV) vaccine-augmented disease, Vaccine, 25(45):7754-62 (2007).

Colas et al., Microscopical investigations of nisin-loaded nanoliposomes prepared by Mozafari method and their bacterial targeting, Micron, 38(8):841-7 (2007).

Gad, Pharmaceutical Manufacturing Handbook: Product and Processes, Section 5.3, Hoboken, NJ: John Wiley & Sons (2008).

Holland et al., Poly(ethylene glycol)—lipid conjugates regulate the calcium-induced fusion of liposomes composed of phosphatidylethanolamine and phosphatidylserine, Biochemistry, 35(8):2618-24 (1996).

Ikehara et al., Recent advancements in cytotoxic T lymphocyte generation methods using carbohydrate-coated liposomes, J. Biomed. Biotechnol., vol. 2010, article ID 242539, 8 pages (2010).

Inoue et al., Comparative responses of liposomes prepared with different ceramide antigens to antibody and complement, Biochemistry, 10(13):2574-81 (1971).

International Search Report and Written Opinion, corresponding International Application No. PCT/US2011/066840, dated Jun. 11, 2012.

Ishii et al., Alpha-galactosylceramide-driven immunotherapy for allergy, Front Biosci., 13:6214-28 (2008).

Kaur et al., Preparation, characterisation and entrapment of a non-glycosidic threitol ceramide into liposomes for presentation to invariant natural killer T cells, J. Pharm. Sci., 100(7):2724-33 (2011).

Khazanov et al., Physicochemical and biological characterization of ceramide-containing liposomes: paving the way to ceramide therapeutic application, Langmuir, 24(13):6965-80 (2008).

Koch et al., The crystal structure of human CD1d with and without alpha-galactosylceramide, Nat. Immunol., 6(8):819-26 (2005).

Lopes et al., Immunization with a lentivector that targets tumor antigen expression to dendritic cells induces potent CD8+ and CD4+ T-cell responses, J. Virol., 82(1):86-95 (2008).

Mui et al., Immune stimulation by a CpG-containing oligodeoxynucleotide is enhanced when encapsulated and delivered in lipid particles, J. Pharmacol. Exp. Ther., 298(3):1185-92 (2001).

Riaz, Liposomes preparation methods, Pak. J. Pharm. Sci., 9(1):65-77 (1996).

Schwendener et al., Liposome-based vaccines, Methods Mol. Biol., 605:163-75 (2010).

Shabbits et al., High ceramide content liposomes with in vivo antitumor activity, Anticancer Res., 23(5A):3663-9 (2003).

Shabbits et al., Intracellular delivery of ceramide lipids via liposomes enhances apoptosis in vitro, Biochim. Biophys. Acta, 1612(1):98-106 (2003).

Silk et al., Cutting edge: nonglycosidic CD1d lipid ligands activate human and murine invariant NKT cells, J. Immunol., 180(10):6452-6 (2008).

Srinivas et al., Customizable, multi-functional fluorocarbon nanoparticles for quantitative in vivo imaging using 19F MRI and optical imaging, Biomaterials, 31(27):7070-7 (2010).

Stover et al., Liposomal delivery enhances short-chain ceramide-induced apoptosis of breast cancer cells, J. Pharmacol. Exp. Ther., 307(2):468-75 (2003).

Stover et al., Systemic delivery of liposomal short-chain ceramide limits solid tumor growth in murine models of breast adenocarcinoma, Clin. Cancer Res., 11(9):3465-74 (2005).

Tamura et al., Characterization of the immature dendritic cells and cytotoxic cells both expanded after activation of invariant NKT cells with alpha-galactosylceramide in vivo, Biochem. Biophys. Res. Commun., 369(2):485-92 (2008).

Tran et al., Combining nanoliposomal ceramide with sorafenib synergistically inhibits melanoma and breast cancer cell survival to decrease tumor development, Clin. Cancer Res., 14(11):3571-81 (2008).

Tran et al., Use of liposomes as drug delivery vehicles for treatment of melanoma, Pigment Cell Melnoma Res., 22(4):388-99 (2009).

Trosko et al., Mechanism of up-regulated gap junctional intercellular communication during chemoprevention and chemotherapy of cancer, Mutation Res., 480-81:219-29 (2001).

Zolnik et al., Rapid distribution of liposomal short-chain ceramide in vitro and in vivo, Drug Metab. Discos., 36(8):1709-15 (2008).

* cited by examiner

LIPOSOMAL FORMULATION OF NONGLYCOSIDIC CERAMIDES AND USES THEREOF

CROSS-REFERENCE TO RELATED APPLICATIONS

The present application claims the benefit of priority of U.S. Provisional Application No. 61/426,725, filed Dec. 23, 2010 and U.S. Provisional Application No. 61/442,755, filed Feb. 14, 2011. The disclosure of each priority application is incorporated herein by reference in its entirety.

TECHNICAL FIELD OF THE INVENTION

The invention generally relates to liposomes that contain nonglycosidic ceramides, compositions that comprise the liposomes, methods of making the liposomes, and methods of using the liposomes to treat diseases.

BACKGROUND OF THE INVENTION

Invariant natural killer T (iNKT) cells have important tumor immunosurveillance properties, and their activation with pharmacological agents is associated with tumour clearance in animal models. The archetypal iNKT cell agonist, α-galactoseceramide (α-GalCer, shown below) is a glycolipid that is currently being used in a limited number of clinical trials for the treatment of lung, myeloma, and head and neck tumors. Treatment with α-GalCer often results in side-effects, such as activation induced anergy of iNKT cells (i.e. long-term unresponsiveness to repeated α-GalCer treatment) and dendritic cell (DC) lysis by iNKT cells following presentation of α-GalCer. Loss of circulating levels of iNKT cells could represent a therapeutically significant limitation with iNKT-cell-based therapies if multi-dosing regimens are required.

α-Galactosylceramide

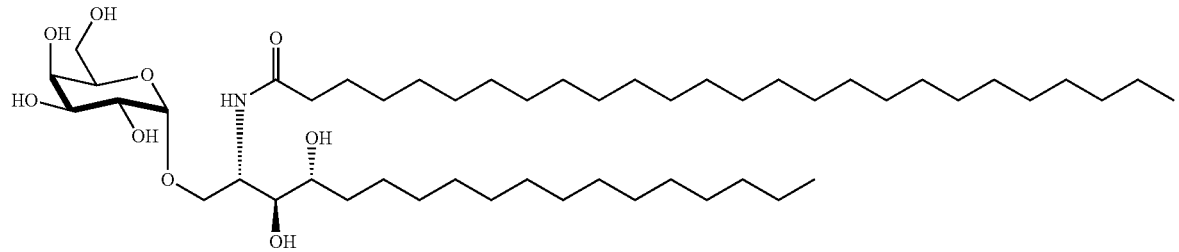

A group of nonglycosidic ceramides that substantially mimic the binding properties of α-GalCer with the human CD1d molecule, but differs significantly in the interaction with T-cell receptors (TCR) compared to α-GalCer is described in U.S. Patent Application Publication No. 2009/0239813 and Silk et al., *J. of Immunol.* 180:6452-6456 (2008), each incorporated herein by reference. These compounds, such as threitolceramide (TC) and glycerolceramide, are able to sensitize murine and human iNKT cells and, like α-GalCer, maintain potent anti-tumor responses in animal models. Some of these nonglycosidic ceramides display poor water solubility, however, which can limit their use clinically. A need exists for the effective delivery of nonglycosidic ceramides for clinical applications.

SUMMARY OF THE INVENTION

The present invention has many facets, including new liposomes; compositions (including pharmaceutical compositions) containing the liposomes, and optionally containing additional agents; methods of making the liposomes and compositions; and methods of using the liposomes and compositions, including therapeutic and prophylactic methods of preventing, ameliorating, treating, and curing diseases.

In one aspect, described herein are liposomes that contain a lipid bilayer membrane surrounding an aqueous core, wherein the lipid bilayer comprises:

(a) a nonglycosidic ceramide present in an amount of about 1 wt. % to about 50 wt. %, based on the total weight of the liposome or the lipid bilayer; and (b) one to five lipids present in an amount of about 50 wt. % to about 99 wt. %, based on the total weight of the liposome or the lipid bilayer.

In some embodiments, the liposomes described herein have a diameter of less than about 100 nm. In some embodiments, the liposomes are about 50 nm to about 150 nm in diameter, or about 75 nm to 125 nm in diameter, or about 75 nm to about 100 nm in diameter. In some embodiments, the liposomes described herein are produced by a method that includes extrusion through an 80 nm filter. In some embodiments, the nonglycosidic ceramide is present in an amount of about 2 wt. % to about 20 wt. %, or about 2 wt. % to about 10 wt. %, based on the total weight of the liposome or the lipid bilayer. In some embodiments, the one to five lipids is present in an amount of about 80 wt. % to about 98 wt. %, based on the total weight of the liposome or the lipid bilayer.

In some embodiments, the nonglycosidic ceramide is a compound of Formula I, or a pharmaceutically acceptable salt thereof:

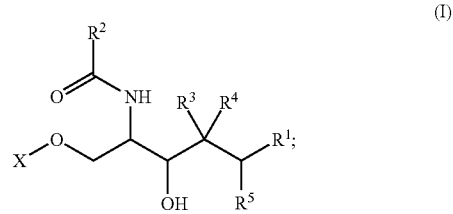

(I)

wherein $R^1$ is a hydrophobic moiety than can occupy the C' channel of human CD1d, and fills at least about 30%, or at least about 35%, of the volume of the C' channel that is occupied by the $(CH_2)_{13}CH_3$ group of α-galactosylceramide (α-GalCer) when the α-GalCer is bound to human CD1d; or $R^1$ is a $C_1$-$C_{25}$ hydrocarbon chain;

$R^2$ is a hydrophobic moiety that can occupy the A' channel of human CD1d, and fills at least about 30%, or at least about 40%, of the volume of the A' channel that is occupied by the $(CH_2)_{24}CH_3$ group of α-GalCer when the α-GalCer is bound to human CD1d; or $R^2$ is a $C_1$-$C_{30}$ hydrocarbon chain;

$R^3$ is H or OH (e.g., H);

$R^4$ and $R^5$ either are both H or together form a single bond, with the proviso that when $R^4$ and $R^5$ together form a single bond, $R^3$ is H;

X is

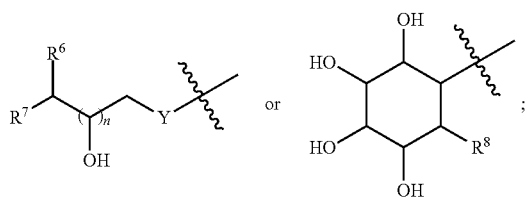

Y is $CH_2$ or

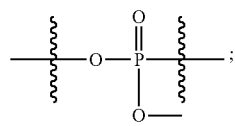 [SMILES: *OP(*)(=O)OC]

$R^6$ and $R^7$ each independently are H, OH, or phenyl, with the proviso that either one of $R^6$ or $R^7$ is H and the other is H, OH, or phenyl, or one of $R^6$ or $R^7$ is OH and the other is phenyl;

$R^8$ is H, OH, or $OSO_3H$; and n is 1, 2, 3, or 4 (e.g., 1, 2, or 3).

In some variations, X is

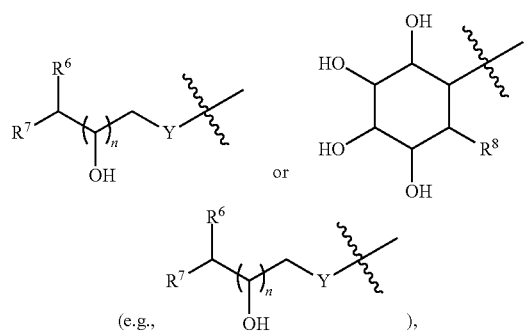

and Y is $CH_2$. In some variations, one of $R^6$ and $R^7$ is H, and the other is either H or OH.

In some variations, $R^1$ is a linear $C_5$-$C_{14}$ hydrocarbon chain, for example, a linear $C_{11}$-$C_{14}$ hydrocarbon chain. In some variations, $R^2$ is a linear $C_8$-$C_{25}$ hydrocarbon chain. In additional or alternative variations, $R^1$, $R^2$, or a combination thereof comprise at least 1 double bond (e.g., 1, 2, or 3 double bonds). Optionally, at least one of the double bonds comprises Z stereochemistry.

In some variations, the nonglycosidic ceramide is selected from the group consisting of arabinitolceramide, glycerolceramide, threitolceramide, threitolceramide C14 acyl, threitol-22-(Z)-ceramide, 4-deoxy-4-phenyl-threitolceramide, 4-deoxy-4-phenyl-threitol-22-(Z)-ceramide, glycerol-phosphate ceramide, inositolceramide, inositolceramide C15 acyl, myoinositolceramide, 4-phenyl threitolceramide, 4-phenyl threitol-22-(Z)-ceramide, threitol-(19Z,22Z)-ceramide, and mixtures thereof. In some exemplary embodiments, the nonglycosidic ceramide is arabinitolceramide, glycerolceramide, threitolceramide, e.g., threitolceramide.

In some embodiments, at least one of the one to five lipids is a phospholipid, such as, for example, a phosphatidylcholine, a phosphatidic acid, a phosphatidylethanolamine, a phosphatidylglycerol, a phosphatidylserine, a phosphatidylinositol, an inositol phosphate, and mixtures thereof.

In some embodiments, the liposomes described herein further comprise at least one antigen (e.g., a viral antigen, a bacterial antigen, a fungal antigen, a tumor antigen, and mixtures thereof). In some embodiments, the at least one antigen comprises a tumor antigen. In some exemplary embodiments, the at least one antigen comprises a full length protein antigen, a long peptide antigen, and a short peptide antigen. In some embodiments, the antigen comprises a hydrophilic antigen.

In some embodiments, the liposome includes at least one antigen in the aqueous core of the liposome. Examples of such antigens include hydrophilic tumor antigens, which include, but are not limited to, NY-ESO-1, tyrosinase, MAGE-3 and Melan-A.

In some embodiments, the liposome includes at least one antigen within the lipid bilayer. Examples of such antigens include hydrophobic tumor antigens.

In some embodiments, the liposome includes at least one antigen that is noncovalently associated with the lipid bilayer. In some embodiments, the liposome includes at least one antigen that is covalently linked to the lipid bilayer, such as, for example, covalently attached to a phospholipid in the lipid bilayer.

In some embodiments, the liposome comprises an antigen with a net negative charge. In some of these embodiments when the liposome comprises an antigen with a net negative charge, the liposome comprises at least two lipids wherein at least one of the lipids is cationic. Nonlimiting examples of the cationic lipid include a trimethyl sphingosine, a trimethyl phytosphingosine, a pyridinium ceramide, a 3β-[N—(N',N'-dimethylaminoethane)-carbamoyl]cholesterol hydrochloride, a 1,2-dioleoyl-3-trimethylammonium-propane, a 1,2-dioleoyl-3-trimethylammonium-propane, a 1,2-dimyristoyl-3-trimethylammonium-propane, a 1,2-dipalmitoyl-3-trimethylammonium-propane, a 1,2-stearoyl-3-trimethylammonium-propane, a 1,2-dioleoyl-3-dimethylammonium-propane, a 1,2-dimyristoyl-3-dimethylammonium-propane, a 1,2-dipalmitoyl-3-dimethylammonium-propane, a 1,2-distearoyl-3-dimethylammonium-propane, a dimethyldioctadecylammonium (Bromide Salt), a 2-dilauroyl-sn-glycero-3-ethylphosphocholine, a 1,2-dimyristoyl-sn-glycero-3-ethylphosphocholine, a 1,2-dimyristoleoyl-sn-glycero-3-ethylphosphocholine, a 1,2-dipalmitoyl-sn-glycero-3-ethylphosphocholine, a 1,2-distearoyl-sn-glycero-3-ethylphosphocholine, a 1,2-dioleoyl-sn-glycero-3-ethylphosphocholine, a 1-palmitoyl-2-oleoyl-sn-glycero-3-ethylphosphocholine, a lysyl phosphatidylglycerol, and mixtures thereof.

In some embodiments, the liposome comprises an antigen with a net positive charge, such as, for example, NY-ESO-1. In some of these embodiments when the liposome comprises an antigen with a net positive charge, the liposome comprises at least two lipids wherein at least one of the lipids is anionic. In some embodiments, the anionic lipid is selected from the group consisting of anionic sphingosine, an anionic phospholipid, a phosphatidylinositol, an inositol phosphate, a cardiolipin, a bis(monoacylglycero)phosphate, an anionic detergent that is not a sphingolipid or a phospholipid, a liponucleotide, a TLR-4 agonist, a diacylglycerol pyrophosphate, and mixtures thereof.

In some embodiments, the tumor antigen comprises a member selected from the group consisting of MUC1, MAGE, BAGE, RAGE, CAGE, SSX-2, NY-ESO-1, PRAME, PSMA, tyrosinase, melan-A, antigenic fragments thereof, and mixtures thereof. In some embodiments, the tumor antigen comprises a member selected from the group consisting of P1A, MUC1, MAGE-A1, MAGE-A2, MAGE-A3, MAGE-A4, MACE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof.

In some embodiments, the liposomes includes at least one zwitterionic lipid. In some embodiments, the liposome comprises at least three lipids.

In some exemplary embodiments, the liposome described herein comprises:

(a) a nonglycosidic ceramide present in an amount of about 1 wt. % to about 20 wt. %, based on the total weight of the liposome or the lipid bilayer;

(b) a first lipid present in an amount of about 15 wt. % to about 55 wt. %, or about 20 wt. % to about 30 wt. %, based on the total weight of the liposome or the lipid bilayer; and, (c) a second lipid present in an amount of about 35 wt. % to about 75 wt. %, or about 65 wt. % to about 75 wt. %, based on the total weight of the liposome or the lipid bilayer, wherein the second lipid is anionic.

In some of these exemplary embodiments, the first lipid and the second lipid have a weight ratio of about 1 to about 3. In some of these embodiments, the nonglycosidic ceramide is present in an amount of about 2 wt. % to about 15 wt. %, or about 3 wt. % to about 12 wt. %, for example, about 5 wt. % or about 10 wt. %, based on the total weight of the liposome or the lipid bilayer.

In some embodiments, the first lipid is a zwitterionic lipid. In some embodiments, the zwitterionic lipid is a phospholipid, for example phosphatidylcholine. In some exemplary embodiments, the phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), egg phosphatidylcholine (EPC), and mixtures thereof. In some embodiments, the zwitterionic lipid is selected from the group consisting of EPC, soy phosphatidylcholine, dioleoylphosphatidylcholine (DOPC) and palmitoyloleoylphosphatidylcholone (POPC).

In some embodiments, the second lipid is an anionic lipid. In some embodiments, the anionic lipid is a phospholipid, for example, phosphatidylglycerol. In some exemplary embodiments, the phosphatidylglycerol is selected from the group consisting of 1,2-dierucoyl phosphatidylglycerol (DEPG), 1,2-dilauroyl phosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2-distearoyl phosphatidylglycerol (DSPG), 1-palmitoyl-2-oleoyl phosphatidylglycerol (POPG), egg phosphatidylglycerol (EPG), salts of any of the foregoing (e.g., sodium, ammonium, or sodium/ammonium), and mixtures thereof, (e.g., egg phosphatidylglycerol). In some embodiments, the liposome comprises a third lipid. In some embodiments, the third lipid is selected from the group consisting of a fatty acid, a glycerolipid, a phospholipid, a sphingolipid, a sterol lipid, a prenol lipid, a saccharolipid, and mixtures thereof. In some exemplary embodiments the third lipid is cholesterol, dimethyldioctadecyl ammonium bromide, and a mixture thereof.

In some of these exemplary embodiments, the liposome further comprises a tumor antigen comprising a net positive charge. In some embodiments, the tumor antigen is NY-ESO-1 and is present in an amount of about 1 µg to about 1 mg per 2 mg of the liposome (e.g., about 400 µg per 2 mg of the liposome).

In some of these exemplary embodiments, the liposome further comprises at least one adjuvant, wherein the at least one adjuvant is in the core of the liposome, in the lipid bilayer, covalently attached to the lipid bilayer, non-covalently associated with the lipid bilayer, or combinations thereof.

In some of these exemplary embodiments, the liposome further comprises at least one therapeutic agent in the core of the liposome. Examples of the therapeutic agent include an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, and combinations thereof.

In some embodiments, the liposome described herein comprises:

(a) a nonglycosidic ceramide present in an amount of about 5 wt. % or about 10 wt. %, based on the total weight of the liposome or the lipid bilayer;

(b) egg phosphatidylcholine in an amount of about 20 wt. % to about 30 wt. %, based on the total weight of the liposome or the lipid bilayer; and, (c) egg phosphatidylglycerol present in an amount of about 65 wt. % to about 75 wt. %, based on the total weight of the liposome or the lipid bilayer.

In another aspect, described herein is a composition comprising the liposome described herein and a pharmaceutically acceptable excipient, carrier, or adjuvant. In some embodiments, the liposome is present in the composition in an amount of about 1 mg/mL to about 20 mg/mL, (e.g., about 13 mg/mL). In some embodiments, the composition further comprises an antigen (e.g., a viral antigen, a bacterial antigen, a tumor antigen, and mixtures thereof) present in an admixture with the liposome. In some embodiments, the antigen comprises a tumor antigen, for example, MUC1, MAGE, BAGE, RAGE, CAGE, SSX-2, NY-ESO-1, PRAME, PSMA, tyrosinase, melan-A, antigenic fragments thereof, and mixtures thereof. In some embodiments, the antigen comprises a tumor antigen selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof. In some exemplary embodiments, the tumor antigen is NY-ESO-1. The NY-ESO-1 can be present in the composition in a concentration of about 0.01 mg/mL to about 5 mg/mL.

In some embodiments, the composition further includes a therapeutic agent present in an admixture with the liposome. In some variations, the therapeutic agent is selected from the group consisting of an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, and mixtures thereof.

The composition described herein can be formulated for parenteral, intrathecal, transdermal, rectal, oral, or nasal administration. Further, the composition described herein can be formulated for administration in a form selected from the group consisting of a tablet, a capsule, a powder, a suppository, a lozenge, a soft gelatin capsule, a transdermal patch, an aerosol, a dragée, a cream, a drop, a liquid suspension, an emulsion, or an ointment.

In another aspect, described herein is a method for stimulating an immune response in a mammalian subject by administering to the subject a liposome or a composition described herein.

In yet another aspect, described herein is a method of treating a viral infection, a microbial infection, a parasitic infection, an autoimmune disease, an allergy, or asthma in a mammalian subject in need thereof comprising administering to the subject the liposome or composition described herein in an amount effective to treat said viral infection, microbial infection, parasitic infection, autoimmune disease, allergy, or asthma.

In some embodiments, the method comprises treating a viral infection caused by a virus is selected from the group consisting of a hepatitis virus, a liver tropic virus, a skin tropic virus, a lung tropic virus, an immune tropic virus, and combinations thereof. In some variations, the virus is hepatitis B virus (HBV), hepatitis C virus (HBC), human papilloma virus (HPV), herpes simplex virus (HSV), influenza virus, respiratory syncytial virus (RSV), human immunodeficiency virus (HIV), Epstein-Barr virus (EBV), cytomegalovirus (CMV), and combinations thereof.

In some embodiments, the method comprises treating a microbial infection selected from the group consisting of a bacterial infection of the lung, a bacterial infection of the gut, a bacterial infection of the skin, or combinations thereof.

In some embodiments where the method is a method of treating an infection caused by an infectious agent selected from a virus, a microbe or bacteria, or a parasite, the method further comprises administering an antigen to the mammalian subject prior to, concurrently with, or after administration of the liposome, wherein the antigen is an antigen that elicits an immune response to the infectious agent.

In some embodiments, the method comprises treating an autoimmune disease selected from the group consisting of psoriasis, Crohn's disease, connective tissue disease, multiple sclerosis, systemic lupus erythematosus, rheumatoid arthritis, autoimmune pulmonary inflammation, Guillain Barre syndrome, autoimmune thyroiditis, insulin dependent diabetes mellitus, myasthenia gravis, graft versus host disease, and autoimmune inflammatory eye disease.

In yet another aspect described herein is a method of treating cancer in a mammalian subject. In this method, the subject is administered a therapeutically effective amount of a liposome or composition described herein. In some variations, at least one further therapeutic or therapy selected from the group consisting of a chemotherapeutic agent, a radiotherapeutic agent, and radiation therapy is administered to the subject. The further therapeutic can be administered concurrently with the liposome or composition described herein or separately.

In some variations of this aspect, the cancer is selected from the group consisting of basal cell carcinoma, breast cancer leukemia, Burkitt's lymphoma, colon cancer, esophageal cancer, bladder cancer, gastric cancer, head and neck cancer, hepatocellular cancer, Hodgkin's lymphoma, hairy cell leukemia, Wilms' tumor, thyroid cancer, thymoma and thymic carcinoma, testicular cancer, T-cell lymphoma, prostate cancer, non-small cell lung cancer, liver cancer, renal cell cancer, melanoma, and combinations thereof.

In some embodiments, described herein is a method of reducing the growth or metastatic spread of a tumor in a mammalian subject. In this method, the subject is administered a therapeutically effective amount of a liposome or composition described herein. In some variations, at least one further therapeutic agent or therapy selected from the group consisting of a chemotherapeutic agent, a radiotherapeutic agent, and radiation therapy is administered to the subject.

In yet another aspect, described herein is a method of making a liposome comprising:

(a) preparing a stock solution of a nonglycosidic ceramide in an organic solvent;

(b) combining an aliquot of the stock solution with a mixture of one to five lipids to form a lipid solution;

(c) diluting the lipid solution with an aqueous solution;

(d) forming multi-lamellar vesicles (MLVs); and, (e) downsizing the MLVs to about 50 nm to about 150 nm at a temperature above the Tc of the lipids by, for example, extrusion.

The following numbered paragraphs each succinctly define one or more exemplary variations of the invention.

1. A liposome comprising:

a lipid bilayer membrane surrounding an aqueous core, wherein the lipid bilayer comprises:

(a) a nonglycosidic ceramide present in an amount of about 1 wt. % to about 50 wt. %, based on the total weight of the liposome or the lipid bilayer; and (b) one to five lipids present in an amount of about 50 wt. % to about 99 wt. %, based on the total weight of the liposome or the lipid bilayer.

2. The liposome of paragraph 1, wherein the diameter of the liposome is less than about 100 nm.

3. The liposome of paragraph 1, wherein the diameter of the liposome is about 50 nm to about 150 nm.

4. The liposome of paragraph 1, wherein the diameter of the liposome is about 75 nm to about 125 nm.

5. The liposome of paragraph 1, wherein the diameter of the liposome is about 75 nm to about 100 nm.

6. The liposome of any one of paragraphs 1 to 5, wherein the liposome is produced by a method that includes extrusion through an 80 nm filter.

7. The liposome of any one of paragraphs 1 to 6, wherein the nonglycosidic ceramide is present in an amount of about 2 wt. % to about 20 wt. %, based on the total weight of the liposome or the lipid bilayer.

8. The liposome of any one of paragraphs 1 to 6, wherein the nonglycosidic ceramide is present in an amount of about 2 wt. % to about 10 wt. %, based on the total weight of the liposome or the lipid bilayer.

9. The liposome of any one of paragraphs 1 to 8, wherein the one to five lipids are present in an amount of about 80 wt. % to about 98 wt. %, based on the total weight of the liposome or the lipid bilayer.

10. The liposome of any one of paragraphs 1-9, wherein the nonglycosidic ceramide is a compound of Formula I, or a pharmaceutically acceptable salt thereof:

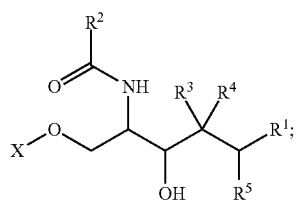

(I)

wherein $R^1$ is a hydrophobic moiety than can occupy the C' channel of human CD1d, and fills at least about 30%, of the volume of the C' channel that is occupied by the $(CH_2)_{13}CH_3$ group of α-galactosylceramide (α-GalCer) when the α-GalCer is bound to human CD1d;

$R^2$ is a hydrophobic moiety that can occupy the A' channel of human CD1d, and fills at least about 30%, of the volume of the A' channel that is occupied by the $(CH_2)_{24}CH_3$ group of α-GalCer when the α-GalCer is bound to human CD1d;

$R^3$ is H or OH;

$R^4$ and $R^5$ either are both H or together form a single bond, with the proviso that when $R^4$ and $R^5$ together form a single bond, $R^3$ is H;

X is

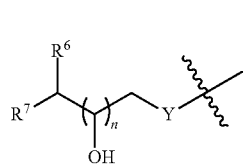 or 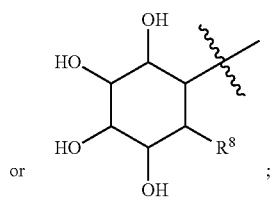 ;

Y is $CH_2$ or

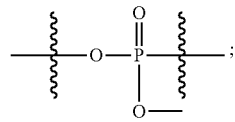 ;

$R^6$ and $R^7$ each independently are H, OH, or phenyl, with the proviso that either one of $R^6$ or $R^7$ is H and the other is H, OH, or phenyl, or one of $R^6$ or $R^7$ is OH and the other is phenyl;

$R^8$ is H, OH, or $OSO_3H$; and n is 1, 2, 3, or 4.

11. The liposome of paragraph 10, wherein $R^1$ fills at least about 35% of the occupied volume of the C' channel, R2 fills at least about 40% of the occupied volume of the A' channel, or a combination thereof.

12. The liposome of paragraph 1, wherein the nonglycosidic ceramide is a compound of Formula I, or a pharmaceutically acceptable salt thereof:

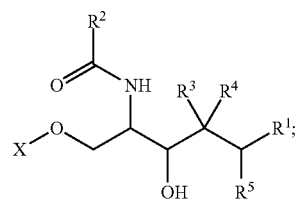

(I)

wherein $R^1$ is a $C_1$-$C_{25}$ hydrocarbon chain;

$R^2$ is a $C_1$-$C_{30}$ hydrocarbon chain;

$R^3$ is H or OH;

$R^4$ and $R^5$ either are both H or together form a single bond, with the proviso that when $R^4$ and $R^5$ together form a single bond, $R^3$ is H;

X is

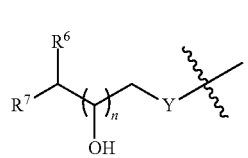 or 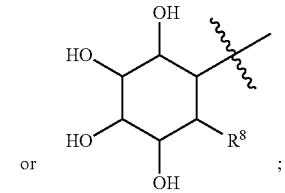 ;

Y is $CH_2$ or

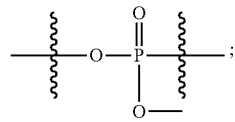 ;

$R^6$ and $R^7$ each independently are H, OH, or phenyl, with the proviso that either one of $R^6$ or $R^7$ is H and the other is H, OH, or phenyl, or one of $R^6$ or $R^7$ is OH and the other is phenyl;

$R^8$ is H, OH, or $OSO_3H$; and n is 1, 2, 3, or 4.

13. The liposome of any one of paragraphs 10 to 12, wherein $R^1$ is a linear $C_5$-$C_{14}$ hydrocarbon chain.

14. The liposome of paragraph 13, wherein $R^1$ is a linear $C_{11}$-$C_{14}$ hydrocarbon chain.

15. The liposome of any one of paragraphs 10 to 14, wherein $R^2$ is a linear $C_8$-$C_{15}$ hydrocarbon chain.

16. The liposome of any one of paragraphs 10 to 15, wherein at least one of $R^1$ and $R^2$ comprises at least 1 double bond.

17. The liposome of paragraph 16, wherein at least one of $R^1$ and $R^2$ comprises 1, 2, or 3 double bonds.

18. The liposome of any one of paragraphs 16-17, wherein the double bond comprises Z stereochemistry.

19. The liposome of any one of paragraphs 10 to 18, wherein X is

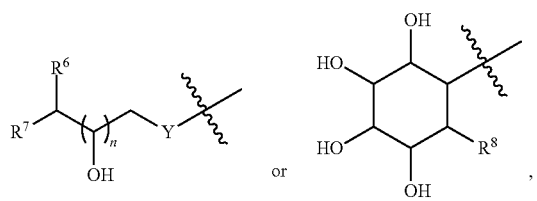

and Y is $CH_2$.

20. The liposome of paragraph 19, wherein X is

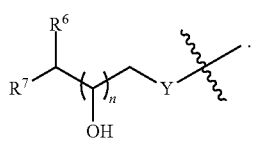

21. The liposome of any one of paragraphs 10 to 20, wherein n is 1, 2, or 3.

22. The liposome of any one of paragraphs 10 to 21, wherein $R^3$ is H.

23. The liposome of any one of paragraphs 10 to 22, wherein $R^6$ and $R^7$ are each H.

25. The liposome of any one of paragraphs 10 to 22, wherein one of $R^6$ or $R^7$ is H and the other is OH.

25. The liposome of any one of paragraphs 1 to 9, wherein the nonglycosidic ceramide is selected from the group consisting of arabinitolceramide, glycerolceramide, threitolceramide, threitolceramide C14 acyl, threitol-22-(Z)-ceramide, 4-deoxy-4-phenyl-threitolceramide, 4-deoxy-4-phenyl-threitol-22-(Z)-ceramide, glycerol-phosphate ceramide, inositolceramide, inositolceramide C15 acyl, myoinositolceramide salt, 4-phenyl threitolceramide, 4-phenyl threitol-22-(Z)-ceramide, threitol-(19Z,22Z)-ceramide, and mixtures thereof.

26. The liposome of paragraph 25, wherein the nonglycosidic ceramide is selected from the group consisting of arabinitolceramide, glycerolceramide, threitolceramide, and mixtures thereof.

27. The liposome of paragraph 25, wherein the nonglycosidic ceramide is threitolceramide.

28. The liposome of any one of paragraphs 1-27, wherein at least one of the one to five lipids is a phospholipid.

29. The liposome of paragraph 28, wherein the phospholipid is selected from the group consisting a phosphatidylcholine, a phosphatidic acid, a phosphatidylethanolamine, a phosphatidylglycerol, a phosphatidylserine, a phosphatidylinositol, an inositol phosphate, and mixtures thereof.

30. The liposome of any one of paragraphs 1-29 further comprising at least one antigen.

31. The liposome according to paragraph 30, wherein the at least one antigen comprises a member selected from the group consisting of a viral antigen, a bacterial antigen, a fungal antigen, a tumor antigen, and mixtures thereof.

32. The liposome of paragraph 30, wherein the at least one antigen comprises at least one tumor antigen.

33. The liposome of according to any one of paragraphs 30 to 32, wherein the at least one antigen comprises a full length protein antigen, a long peptide antigen, and a short peptide antigen.

34. The liposome of any one of paragraphs 30 to 33, wherein the at least one antigen includes a hydrophilic antigen.

35. The liposome according to any one of paragraphs 30 to 34, wherein the liposome includes at least one antigen in the aqueous core of the liposome.

36. The liposome of any one of paragraphs 30 to 35, wherein the liposome includes at least one antigen within the lipid bilayer.

37. The liposome of any one of paragraphs 30 to 36, wherein the liposome includes at least one antigen attached to the outside of the lipid bilayer.

38. The liposome of any one of paragraphs 30 to 37, wherein the liposome includes at least one antigen that is noncovalently associated with the lipid bilayer.

39. The liposome of any one of paragraphs 30 to 38, wherein the liposome includes at least one antigen that is covalently linked to the lipid bilayer.

40. The liposome of paragraph 39, wherein the liposome includes at least one antigen that is covalently attached to a phospholipid in the lipid bilayer.

41. The liposome of any one of paragraphs 30 to 40, wherein the liposome comprises at least one antigen with a net negative charge.

42. The liposome of paragraph 41, wherein the liposome comprises at least two lipids, wherein at least one of the lipids is cationic.

43. The liposome of paragraph 42, wherein the cationic lipid selected from the group consisting of a trimethyl sphingosine, a trimethyl phytosphingosine, a pyridinium ceramide, a 3β-[N—(N',N'-dimethylaminoethane)-carbamoyl]cholesterol hydrochloride, a 1,2-dioleoyl-3-trimethylammonium-propane, a 1,2-dioleoyl-3-trimethylammonium-propane, a 1,2-dimyristoyl-3-trimethylammonium-propane, a 1,2-dipalmitoyl-3-trimethylammonium-propane, a 1,2-stearoyl-3-trimethylammonium-propane, a 1,2-dioleoyl-3-dimethylammonium-propane, a 1,2-dimyristoyl-3-dimethylammonium-propane, a 1,2-dipalmitoyl-3-dimethylammonium-propane, a 1,2-distearoyl-3-dimethylammonium-propane, a dimethyldioctadecylammonium (Bromide Salt), a 2-dilauroyl-sn-glycero-3-ethylphosphocholine, a 1,2-dimyristoyl-sn-glycero-3-ethylphosphocholine, a 1,2-dimyristoleoyl-sn-glycero-3-ethylphosphocholine, a 1,2-dipalmitoyl-sn-glycero-3-ethylphosphocholine, a 1,2-distearoyl-sn-glycero-3-ethylphosphocholine, a 1,2-dioleoyl-sn-glycero-3-ethylphosphocholine, a 1-palmitoyl-2-oleoyl-sn-glycero-3-ethylphosphocholine, a lysyl phosphatidylglycerol, and mixtures thereof.

44. The liposome of any one of paragraphs 30 to 43, wherein the liposome comprises at least one antigen with a net positive charge.

45. The liposome of paragraph 44, wherein the tumor antigen comprises a member selected from the group consisting of MUC1, MAGE, BAGE, RAGE, CAGE, SSX-2, NY-ESO-1, PRAME, PSMA, tyrosinase, melan-A, antigenic fragments thereof, and mixtures thereof.

45.1 The liposome of paragraph 44, wherein the tumor antigen comprises a member selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof.

46. The liposome of paragraph 44 or 45, wherein the liposome comprises at least two lipids, wherein at least one of the lipids is anionic.

47. The liposome of paragraph 46, wherein the anionic lipid is selected from the group consisting of anionic sphingosine, an anionic phospholipid, a phosphatidylinositol, an inositol phosphate, a cardiolipin, a bis(monoacylglycero) phosphate, an anionic detergent that is not a sphingolipid or a phospholipid, a liponucleotide, a TLR-4 agonist, a diacylglycerol pyrophosphate, and mixtures thereof.

48. The liposome of any one of paragraphs 1 to 47, wherein the liposome includes at least one zwitterionic lipid.

49. The liposome of any one of paragraphs 1 to 48 comprising at least three lipids.

50. The liposome of any one of the paragraphs 1-40 comprising:
(a) a nonglycosidic ceramide present in an amount of about 1 wt. % to about 20 wt. %, based on the total weight of the liposome or the lipid bilayer;
(b) a first lipid present in an amount of about 15 wt. % to about 55 wt. %, based on the total weight of the liposome or the lipid bilayer; and,
(c) a second lipid present in an amount of about 35 wt. % to about 75 wt. %, based on the total weight of the liposome or the lipid bilayer, wherein the second lipid is anionic.

51. The liposome of paragraph 50 further comprising a tumor antigen comprising a net positive charge.

52. The liposome of paragraph 50, wherein the nonglycosidic ceramide is present in an amount of about 2 wt. % to about 15 wt. %, based on the total weight of the liposome or the lipid bilayer.

53. The liposome of paragraph 52, wherein the nonglycosidic ceramide is present in an amount of about 3 wt. % to about 12 wt. %, based on the total weight of the liposome or the lipid bilayer.

54. The liposome of paragraph 53, wherein the nonglycosidic ceramide is present in an amount of about 5 wt. %, based on the total weight of the liposome or the lipid bilayer.

55. The liposome of paragraph 53, wherein the nonglycosidic ceramide is present in an amount of about 10 wt. %, based on the total weight of the liposome or the lipid bilayer.

56. The liposome of any one of paragraphs 50-55, wherein the first lipid is a zwitterionic lipid.

57. The liposome of paragraph 56, wherein the zwitterionic lipid is a phosphosolipid.

58. The liposome of paragraph 57, wherein the phospholipid is phosphatidylcholine.

59. The liposome of paragraph 58, wherein the phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), egg phosphatidylcholine (EPC), and mixtures thereof.

60. The liposome of any one of paragraphs 50-59, wherein the first lipid comprises egg phosphatidylcholine.

61. The liposome of any one of paragraphs 50-60, wherein the second lipid comprises a phospholipid.

62. The liposome of paragraph 61, wherein the second lipid comprises phosphatidylglycerol.

63. The liposome of paragraph 62, wherein the phosphatidylglycerol is selected from the group consisting of 1,2-dierucoyl phosphatidylglycerol (DEPG), 1,2-dilauroyl phosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2-distearoyl phosphatidylglycerol (DSPG), 1-palmitoyl-2-oleoyl phosphatidylglycerol (POPG), egg phosphatidylglycerol (EPG), salts of any of the foregoing, and mixtures thereof.

64. The liposome of any one of paragraphs 50-63, wherein the second lipid comprises egg phosphatidylglycerol.

65. The liposome of any one of paragraphs 50-64, wherein the first lipid is present in an amount of about 20 wt. % to about 30 wt. % and the second lipid is present in an amount of about 65 wt. % to about 75 wt. %, based on the total weight of the liposome or the lipid bilayer.

66. The liposome of any one of paragraphs 50-65, wherein the weight ratio of the first lipid to the second lipid is about 1 to about 3.

67. The liposome of any one of paragraphs 50-66, wherein the tumor antigen comprises a member selected from the group consisting of MUC1, MAGE, BAGE, RAGE, CAGE, SSX-2, NY-ESO-1, PRAME, PSMA, tyrosinase, melan-A, antigenic fragments thereof, and mixtures thereof.

67.1. The liposome of any one of paragraphs 50-66, wherein the tumor antigen comprises a member selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof.

68. The liposome of paragraph 67, wherein the tumor antigen is NY-ESO-1 and is present in an amount of about 1 µg to about 1 mg per 2 mg of the liposome.

69. The liposome of paragraph 68, wherein the NY-ESO-1 is present in an amount of about 400 µg per 2 mg of the liposome.

70. The liposome of any one of paragraphs 1-69, further comprising at least one adjuvant, wherein the at least one adjuvant is in the core of the liposome, in the lipid bilayer, covalently attached to the lipid bilayer, non-covalently associated with the lipid bilayer, or combinations thereof.

71. The liposome of any one of paragraphs 1-70 further comprising at least one therapeutic agent in the core of the liposome.

72. The liposome of paragraph 71, wherein the at least one therapeutic agent is selected from the group consisting of an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, and combinations thereof.

73. The liposome of any one of the paragraphs 1-72 comprising:
(a) a nonglycosidic ceramide present in an amount of about 5 wt. % or about 10 wt. %, based on the total weight of the liposome or the lipid bilayer;
(b) egg phosphatidylcholine in an amount of about 20 wt. % to about 30 wt. %, based on the total weight of the liposome or the lipid bilayer; and,
(c) egg phosphatidylglycerol present in an amount of about 65 wt. % to about 75 wt. %, based on the total weight of the liposome or the lipid bilayer;
wherein the diameter of the liposome is less than about 100 nm.

74. A composition comprising the liposome of any one of paragraphs 1-72 and a pharmaceutically acceptable diluent, excipient, carrier, or adjuvant.

75. The composition of paragraph 74, wherein the liposome is present in the composition in an amount of about 1 mg/mL to about 20 mg/mL.

76. The composition of paragraph 75, wherein the liposome is present in an amount of about 13 mg/mL.

77. The composition of any one of paragraphs 74-76 further comprising at least one antigen admixed with the liposome.

78. The composition according to paragraph 77, wherein the at least one antigen is selected from the group consisting of a viral antigen, a bacterial antigen, a tumor antigen, and mixtures thereof.

79. The composition of paragraph 77, wherein the at least one antigen comprises a tumor antigen.

80. The composition of paragraph 79, wherein the tumor antigen comprises a member selected from the group consisting of MUC1, MAGE, BAGE, RAGE, CAGE, SSX-2, NY-ESO-1, PRAME, PSMA, tyrosinase, melan-A, antigenic fragments thereof, and mixtures thereof.

80.1. The composition of paragraph 79, wherein the tuor antigen comprises a member selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof.

81. The composition of paragraph 80, wherein the tumor antigen is NY-ESO-1 and is present in the composition in a concentration of about 0.1 mg/mL to about 5 mg/mL.

82. The composition of any one of paragraphs 74-81, further comprising at least one adjuvant in an admixture with the liposome.

83. The composition of any one of paragraphs 74-82 further comprising at least one therapeutic agent present in an admixture with the liposome.

84. The composition of paragraph 83, wherein the at least one therapeutic agent is selected from the group consisting of an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, and combinations thereof.

85. The composition of any one of paragraphs 74-84, wherein the composition is formulated for parenteral, intrathecal, transdermal, rectal, oral, or nasal administration.

86. The composition of paragraph 85, wherein the composition is formulated for intravenous, intraperitoneal, subcutaneous, or intramuscular administration.

87. A method of stimulating an immune response in a mammalian subject comprising administering to the subject a liposome according to any one of paragraphs 1-73 or a composition according to any one of paragraphs 74-86.

88. The method of paragraph 87, further comprising administering an antigen to the mammalian subject prior to, concurrently with, or after administration of the liposome, wherein the immune response is an immune response to the antigen.

89. A method of treating a viral infection, a microbial infection, a parasitic infection, an autoimmune disease, an allergy, or asthma in a mammalian subject in need thereof comprising administering to the subject the liposome of any one of paragraphs 1-73 or a composition according to any one of paragraphs 74-86 in an amount effective to treat said viral infection, microbial infection, parasitic infection, autoimmune disease, allergy, or asthma.

90. The method of paragraph 89, comprising treating a viral infection caused by a virus selected from the group consisting of a hepatitis virus, a liver tropic virus, a skin tropic virus, a lung tropic virus, an immune tropic virus, and combinations thereof.

91. The method of paragraph 90, wherein the virus is hepatitis B virus (HBV), hepatitis C virus (HBC), human papilloma virus (HPV), herpes simplex virus (HSV), influenza virus, respiratory syncytial virus (RSV), human immunodeficiency virus (HIV), Epstein-Ban virus (EBV), cytomegalovirus (CMV), and combinations thereof.

92. The method of paragraph 89, comprising treating a microbial infection selected from the group consisting of a bacterial infection of the lung, a bacterial infection of the gut, a bacterial infection of the skin, and combinations thereof.

93. The method of any one of paragraphs 89 to 92 that is a method of treating an infection caused by an infectious agent selected from a virus, a microbe or bacteria, or a parasite, wherein the method further comprises administering an antigen to the mammalian subject prior to, concurrently with, or after administration of the liposome, wherein the antigen is an antigen that elicits an immune response to the infectious agent.

94. The method of paragraph 89, comprising treating an autoimmune disease selected from the group consisting of psoriasis, Crohn's disease, connective tissue disease, multiple sclerosis, systemic lupus erythematosus, rheumatoid arthritis, autoimmune pulmonary inflammation, Guillain Bane syndrome, autoimmune thyroiditis, insulin dependent diabetes mellitis, myasthenia gravis, graft versus host disease, and autoimmune inflammatory eye disease.

95. A method of treating a cancer in a mammalian subject comprising administering to said subject a therapeutically effective amount of a liposome according to any one of paragraphs 1-73 or a composition according to any one of paragraphs 74-86.

96. The method of paragraph 95, wherein the cancer is selected from the group consisting of basal cell carcinoma, breast cancer leukemia, Burkitt's lymphoma, colon cancer, esophageal cancer, bladder cancer, gastric cancer, head and neck cancer, hepatocellular cancer, Hodgkin's lymphoma, hairy cell leukemia, Wilms' tumor, thyroid cancer, thymoma and thymic carcinoma, testicular cancer, T-cell lymphoma, prostate cancer, non-small cell lung cancer, liver cancer, renal cell cancer, melanoma, and combinations thereof.

97. The method of paragraph 95 or 96, further comprising the step of administering to the subject at least one further therapeutic or therapy selected from the group consisting of a chemotherapeutic agent, a radiotherapeutic agent, and radiation therapy.

98. The method of paragraph 97, wherein the liposome and the further therapeutic or therapy are administered concurrently.

99. The method of paragraph 97, wherein the liposome and the further therapeutic or therapy are administered separately.

100. The method according to any one of paragraphs 95 to 99, further comprising administering a tumor antigen to the mammalian subject prior to, concurrently with, or after administration of the liposome.

101. A method of reducing the growth or metastatic spread of a tumor in a mammalian subject comprising administering to said subject a therapeutically effective amount of a combination therapy comprising a liposome according to any one of paragraphs 1-73 or a composition according to any one of paragraphs 74-86 and at least one further therapeutic or therapy selected from the group consisting of a chemotherapeutic agent, a radiotherapeutic agent, and radiation therapy.

102. Use of a liposome according to any one of paragraphs 1-73 or a composition according to any one of paragraphs 74-86 for treating cancer in a mammalian subject, or in the manufacture of a medicament for treating cancer in a mammalian subject.

103. Use of a liposome according to any one of paragraphs 1-73 or a composition according to any one of paragraphs 74-86 for treating an autoimmune disease in a mammalian subject, or in the manufacture of a medicament for treating an autoimmune disease in a mammalian subject.

104. Use of a liposome according to any one of paragraphs 1-73 or a composition according to any one of paragraphs 74-86 for treating a disorder selected from the group consisting of a viral infection, a bacterial infection, an allergy, a parasitic infection and asthma in a mammalian subject, or in the manufacture of a medicament for treating a disorder selected from the group consisting of a viral infection, a bacterial infection, an allergy, a parasitic infection and asthma in a mammalian subject.

105. Use of a liposome according to any one of paragraphs 1-73 or a composition according to any one of paragraphs 74-86 for stimulating an immune response in a mammalian subject, or in the manufacture of a medicament for stimulating an immune response in a mammalian subject.

106. The method or use of any one of paragraphs 87-105, wherein the mammalian subject is human.

107. A method of making a liposome of any one of paragraphs 1-73, comprising:
(a) preparing a stock solution of a nonglycosidic ceramide in an organic solvent;
(b) combining an aliquot of the stock solution with a mixture of one to five lipids to form a lipid solution;
(c) diluting the lipid solution with an aqueous solution;
(d) forming multi-lamellar vesicles (MLVs); and,
(e) downsizing the MLVs to about 50 nm to about 150 nm at a temperature above the Tc of the lipids.

108. The method of paragraph 107, wherein the aqueous solution further comprises an antigen.

109. The method of any one of paragraphs 107-108, wherein the MLVs are downsized using extrusion.

110. The method of paragraph 109, wherein the extrusion is through an 80 nm filter.

111. The method of any one of paragraphs 107-110, wherein the MLV's are downsized to liposomes less than 100 nm in size.

112. The method of any one of paragraphs 107-111 further comprising mixing the liposomes with a pharmaceutically acceptable carrier.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Aspects of the invention described as methods of treatment should also be understood to include first or subsequent "medical use" aspects of the invention or "Swiss use" of compositions for the manufacture of a medicament for treatment of the same disease or condition.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

DETAILED DESCRIPTION OF THE INVENTION

Figure 1A:
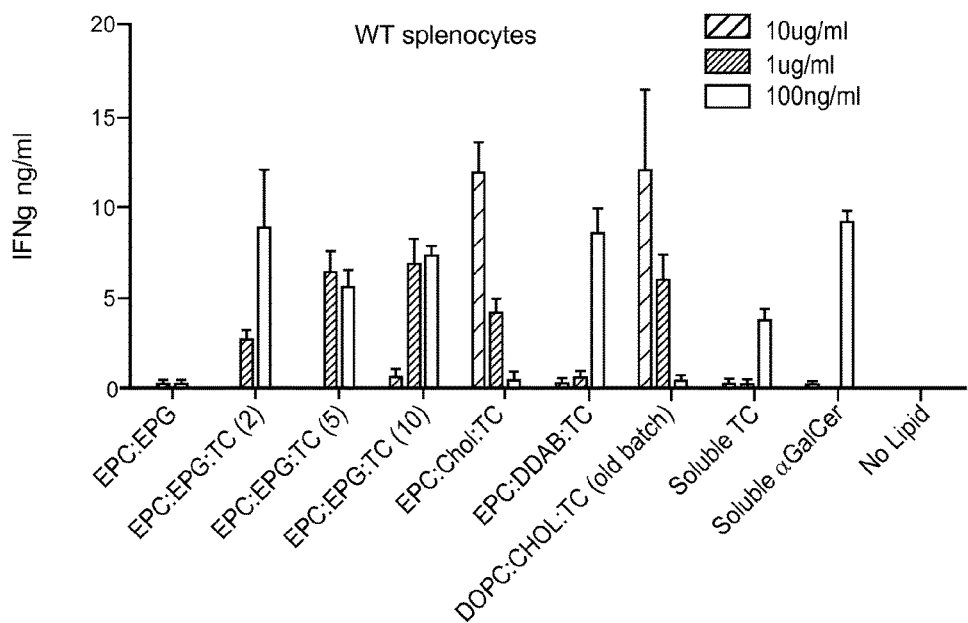
FIG. 1A shows that nonglycosidic ceramide containing liposomes activate iNKT cells in vitro in splenocytes prepared from wild-type mice.

The present application is based on the discovery that nonglycosidic ceramides can be incorporated into liposomes, and that these liposomes perform comparably to their soluble (i.e., free, non-liposomal) nonglycosidic ceramide counterparts. The liposomes described herein were found to activate murine iNKT cells and induce dendritic cell (DC) maturation, both in vitro and in vivo at an efficacy that is at least comparable to their corresponding soluble nonglycosidic ceramides. The liposomes described herein were also found to expand an andogenous T cell repertoire, which recognizes the ovalbulmin (OVA) pepetide SIINFEKL (SEQ ID NO: 1), in an in vivo mouse model.

Liposomes are lipid-containing vesicles that include one or several concentric lipid bilayers enclosing an aqueous core, and can be used to deliver both hydrophilic and hydrophobic bioactive agents to the body. Small, hydrophilic bioactive agents can be encapsulated within the aqueous core (cavity) of a liposome. Both charged, hydrophilic bioactive agents and uncharged, hydrophobic bioactive agents can be associated with the membrane of a liposome through electrostatic or hydrophobic interactions, respectively, or through a covalent bond. Liposomes can deliver bioactive agents to the body by, for example, fusion of the liposome with other bilayers, such as the cell membrane, diffusion of the compound out of the liposome, or digestion of the liposome within macrophages.

As described in U.S. Pat. No. 7,060,291, incorporated herein by reference, liposomes can have a variety of sizes, e.g., an average diameter as low as 25 nm or as high as 10,000 nm or more. Size is affected by a number of factors, such as, for example, lipid composition and method of preparation, and is determined by a number of techniques, such as quasi-elastic light scattering. Various methodologies can be used to prepare liposomes of a smaller size from larger liposomes, such as sonication, homogenization, French Press application, and milling. Extrusion (see, e.g., U.S. Pat. No. 5,008,050, incorporated herein by reference) can be used to produce liposomes having a predetermined mean size by forcing the liposomes, under pressure, through filter pores of a defined, selected size. Tangential flow filtration, as described in PCT Application No. WO 1989/008846, incorporated herein by reference, also can be used to regularize the size of liposomes (i.e., produce a population of liposomes having less size heterogeneity, and a more homogeneous, defined size distribution).

Using liposomes to deliver of bioactive agents is highly advantageous. Unlike micellar delivery vehicles, liposomes are physically stable. The liposomal lipid composition can be tailored to deliver specific bioactive agents to targeted locations, which limits the potential toxicity of the bioactive agents. Further, liposomes allow the delivery of known amounts of bioactive agents because they minimize loss of the bioactive agent from, for example, degradation, removal by non-target organs, and precipitation, as seen with detergents. Liposomes also provide a method for co-delivering adjuvants and antigens in particular ratios that otherwise cannot occur by, for example, coinjection, as described in U.S. Pat. Nos. 7,850,990 and 7,842,676, each incorporated herein by reference.

Schwendener et al., *Methods Mol. Biol.* 605:163-175 (2010), incorporated herein by reference, discloses liposomal vaccine formulations for the entrapment of antigenic peptides and antigen encoding plasmid DNAs. Inoue et al., *Biochemistry* 19(13):2574-2581 (1971), incorporated herein by reference, discloses liposomes (e.g., 1:1 equimolar mixture of lecithin and sphingomyelin) comprising galactrocerbroside or cytolipin K. U.S. Pat. No. 5,543,152, incorporated herein by reference, discloses liposomes composed of sphingomyelin and cholesterol having an acidic intraliposomal pH that can deliver lipophilic drugs (e.g., alkaloid compounds) to mammalian hosts.

U.S. Pat. No. 5,705,385, incorporated herein by reference, discloses charge-neutralized lipid-nucleic acid particles useful for the delivery of nucleic acids. The particles comprise lipids that are both non-cationic and cationic, and can optionally include polyethylene glycol(PEG)-modified ceramide (e.g., 1-15 wt. %, based on the total weight of the particle). The PEG-ceramide prevents particle aggregation, provides a means for increasing circulation lifetime, and provides a means for increasing the delivery of the lipid-nucelic acid particles to the target tissues. Holland et al., *Biochemistry* 35:2618-2624 (1996), incorporated herein by reference, discloses large, unilamellar vesicles (LUVs) comprising equimolar amounts of phosphatidylethanolamine and phosphatidylserine, along with egg ceramide-PEG(2000 Da) conjugates. The ceramide-PEG was found to inhibit LUV fusion. Benoit et al., *Vaccine* 25:7754-7762 (2007), incorporated herein by reference, discloses a liposome-based vaccine comprising dioleoylphosphatidylcholine (DOPC), a recombinant protein consisting of a fragment of thioredoxin fused in frame to a portion of the RSV G protein (Trx-G), and α-galactosylceramide in amounts of 1 mg/mouse, 7.5 µg/mouse, and 4 µg/mouse, respectively. Mui et al., *Journal of Pharmacology and Experimental Therapeutics* 298(3):1185-1192 (2001), incorporated herein by reference, discloses liposome formulations (e.g., 100 nm in diameter) comprising plasmids and CpG that contain pegylated ceramides. Shabbits and Mayer, *Biochem. Biophys. Acta* 1612(1):98-106 (2003) and Shabbits and Mayer, *Anticancer Res.* 23(5A):3663-3669 (2003), each incorporated herein by reference, disclose ceramide-containing liposomes. Tamura et al., *Biochem. Biophys. Res. Commun.* 369(2):485-492 (2008), incorporated herein by reference, disclose α-GalCer-liposomes. Ishii et al., *Front Biosci.* 13:6214-6228 (2008), incorporated herein by reference, discloses α-GalCer-OVA-liposomes. Stover et al., *Clin. Cancer Res.* 11(9):3465-3474 (2005); Stover and Kester, *Journal of Pharmacology and Experimental Therapeutics* 307(2):468-475; Zolnik et al., *Drug Metabolism and Disposition* 36:1709-1715 (2008); Tran et al., *Clin. Cancer Res.* 14(11):3571-3581 (2008); Khazanov et al., *Langmuir* 24(13):6965-6980 (2008); and Tran et al., *Pigment Cell Melanoma Res.* 22(4):388-399 (2009), each incorporated herein by reference, disclose neutral liposomal formulations, either pegylated or non-pegylated, comprising $C_6$-ceramides.

As used herein, the term "nonglycosidic ceramide" refers to ceramide that does not comprise a sugar moiety.

As used herein, the term "soluble," when modifying a nonglycosidic ceramide, refers to a nonglycosidic ceramide that is dissolved or suspended in a composition in a form that is not incorporated into the bilayer of a liposome. In some embodiments, the soluble nonglycosidic ceramide is solubilized or suspended in a surfactant. In some exemplary embodiments, the nonglycosidic ceramide can be dissolved in a chloroform/methanol/water solution (e.g., 10:10:3) at, for example, about 10 mg/mL and then diluted to a final volume of about 200 µg/mL using vehicle solution comprised of, for example, NaCl (about 150 mM) and polyoxyethylene (20) sorbitan monolaurate (i.e., Tween 20, 0.5%).

As used herein the term "pharmaceutically acceptable salt" refers to salts of compounds that retain biological activity of interest of the parent compound, such as therapeutic activity, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein an "effective" amount or a "therapeutically effective amount" refers to a nontoxic amount of an agent that is effective to provide one or more desired effects in vivo, when administered to a subject in need of prophylaxis or therapy. The amount that is "effective" will vary from subject to subject, depending on the age and general condition of the individual, mode of administration, and the like. An "effective" amount in any individual case may be determined using routine experimentation, such as dose-response studies.

As used herein, the term "treating" includes prophylaxis of the specific disorder or condition, or alleviation of the symptoms associated with a specific disorder or condition and/or preventing or eliminating said symptoms, and/or eliminating the condition (cure). "Prophylaxis" refers to a preventative therapy and its effectiveness can be shown by comparison between a population that receives the prophylaxis and a population that only receives a negative control. Effective prophylaxis results in reduced incidence and/or reduced severity compared to the control population. In the context of an infection, treating refers to slowing the spread of the infection and/or stopping the spread of the infection and/or reducing or eliminating the amount of the infective agent in a host. In the context of a cancer, an effective treatment slows the growth of the cancer and/or reduces its harmful effect on a patient and/or increases the life span of a cancer patient and/or increases the span of quality life of the patient; or causes shrinkage of a tumor or reduction in the number of cancer cells, or results in elimination of the cancer. In the context of vaccination, treatment causes the body to produce an immune response that inhibits or prevents future infection by an infective agent, or reduces the infection's severity or duration or negative effects if infection occurs.

Liposomes

In one aspect, described herein is a liposome comprising a lipid bilayer membrane surrounding an aqueous core, wherein the lipid bilayer comprises (a) a nonglycosidic ceramide present in an amount of about 1 wt. % to about 50 wt. %, and (b) one to five lipids (e.g., 1, 2, 3, 4, or 5 lipids) present in an amount of about 50 wt. % to about 99 wt. %, based on the total weight of the liposome or the lipid bilayer.

In some embodiments, the liposome has a diameter of less than about 100 nm. In some embodiments, the liposome has a diameter of about 50 nm to about 150 nm, or about 60 nm to about 140 nm, or about 70 nm to about 130 nm, or about 75 to nm to about 125 nm, or about 75 nm to about 100 nm, for example, about 100 nm. In some embodiments, the liposome has a diameter of 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm.

Stated another way, in some embodiments the liposome has a diameter defined by a size range, with the lower end of the size range being any size selected from about 25 nm, 30 nm, 35 nm, 40 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm; and with the upper end of the size range being any size selected from about 175 nm, 170 nm, 165 nm, 160 nm, 155 nm, 150 nm, 145 nm, 144 nm, 143 nm, 142 nm, 141 nm, 140 nm, 139 nm, 138 nm, 137 nm, 136 nm, 135 nm, 134 nm, 133 nm, 132 nm, 131 nm, 130 nm, 129 nm, 128 nm, 127 nm, 126 nm, 125 nm, 124 nm, 123 nm, 122 nm, 121 nm, 120 nm, 119 nm, 118 nm, 117 nm, 116 nm, 115 nm, 114 nm, 113 nm, 112 nm, 111 nm, 110 nm, 109 nm, 108 nm, 107 nm, 106 nm, 105 nm, 104 nm, 103 nm, 102 nm, 101 nm, 100 nm, 99 nm, 98 nm, 97 nm, 96 nm, 95 nm, 94 nm, 93 nm, 92 nm, 91 nm, or 90 nm.

The nonglycosidic ceramide can be any nonglycosidic ceramide known to one skilled in the art. Nonlimiting examples of nonglycosidic ceramides are described in U.S. Patent Application Publication No. 2009/0239813 and Silk et al., *J. of Immunol.* 180:6452-6456 (2008), the disclosure of which are incorporated herein by reference in their entireties. Liposomes that include two or more nonglycosidic ceramides are specifically contemplated.

In some embodiments, the nonglycosidic ceramide is a compound of Formula I or a pharmaceutically acceptable salt thereof:

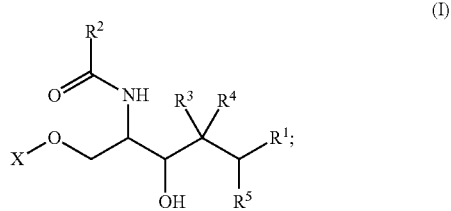

(I)

wherein $R^1$ is a hydrophobic moiety than can occupy the C' channel of human CD1d, and fills at least about 30% of the volume of the C' channel that is occupied by the $(CH_2)_{13}CH_3$ group of α-galactosylceramide (α-GalCer) when the α-GalCer is bound to human CD1d; or $R^1$ is a $C_1$-$C_{25}$ hydrocarbon chain;

$R^2$ is a hydrophobic moiety that can occupy the A' channel of human CD1d, and fills at least about 30% of the volume of the A' channel that is occupied by the $(CH_2)_{24}CH_3$ group of α-GalCer when the α-GalCer is bound to human CD1d; or $R^2$ is a $C_1$-$C_{30}$ hydrocarbon chain;

$R^3$ is H or OH, for example, H;

$R^4$ and $R^5$ either are both H or together form a single bond, with the proviso that when $R^4$ and $R^5$ together form a single bond, $R^3$ is H;

X is

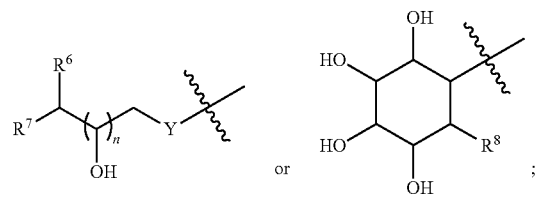

Y is $CH_2$ or

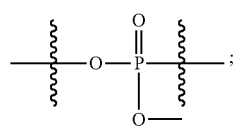

$R^6$ and $R^7$ each independently are H, OH, or phenyl, with the proviso that either one of $R^6$ or $R^7$ is H and the other is H, OH, or phenyl, or one of $R^6$ or $R^7$ is OH and the other is phenyl;

$R^8$ is H, OH, or $OSO_3H$; and n is 1, 2, 3, or 4, for example, 1, 2, or 3.

In some embodiments, $R^1$ fills at least about 35%, at least about 60%, at least about 80%, or at least about 90% of the occupied volume of the C' channel. In some embodiments, $R^2$ fills at least about 40%, at least about 50%, at least about 60%, at least about 70%, or at least about 80% of the occupied volume of the A' channel.

The conditions for a substantially full occupation of both the A' and C' channels of human CD1d, as exhibited by α-GalCer, are described in detail in Koch et al, *Nature Immunology*, 6(8) 819-826 (2005), incorporated herein by reference. In Koch et al., cavities were identified as surfaces that are accessible to water molecules (radius, 1.4 Å), but not to large probes (radius, 6 Å) with the program VOLUMES (R. Esnouf, University of Oxford, Oxford, UK). The open nature of the pockets at the TCR recognition surface required imposition of a self-consistent definition for the outer limit of the pocket, and on this basis the authors calculated the pocket volumes for mouse CD1d, CD1a and CD1b, as well as human CD1d. Although these calculations resulted in some differences in absolute values from those reported before, the same relative trends were noted.

In some embodiments, $R^1$ (i.e., the sphingosine chain) does not exceed 13 carbon-carbon single bonds in length. For example, $R^1$ can be a linear $C_5$-$C_{13}$ hydrocarbon chain, a linear $C_{11}$-$C_{13}$ hydrocarbon chain, or a linear $C_{12}$-$C_{13}$ hydrocarbon chain. In some embodiments, $R^2$ (i.e., the acyl chain) does not exceed 25 carbon-carbon single bonds in length. In some embodiments, $R^2$ comprises at least 1 carbon atom, at least 5 carbon atoms, at least 8 carbon atoms, at least 9 carbon atoms, at least 10 carbon atoms, at least 11 carbon atoms, at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, at least 20 carbon atoms, at least 21 carbon atoms, at least 22 carbon atoms, at least 23 carbon atoms, at least 24 carbon atoms, or at least 25 carbon atoms. For example, $R^2$ can be a linear $C_1$-$C_{25}$ hydrocarbon chain, a linear $C_5$-$C_{25}$ hydrocarbon chain, a linear $C_1$-$C_{16}$ hydrocarbon chain, $C_1$-$C_{18}$ hydrocarbon chain or a linear $C_8$-$C_{25}$ hydrocarbon chain.

In some embodiments, the compounds of Formula I bind to human CD1d with good shape complementarity, (i.e., with a $S_c$ greater than 0.50, greater than 0.55, or greater than 0.60). Shape complementarity analysis was made using the program SC (http://www.ccp4.ac.uk/ccp4i_main.html). Using this analysis, the 26 carbon acyl chain and the 18 carbon sphingosine chain of α-GalCer were found to fit into the A' and C' channels of human CD1d, respectively, with a shape complementarity ($S_c$) of 0.61. The total volume of these cavities (1,400 Å$^3$) in the human CD1d binding groove is essentially filled by the hydrocarbon chains. The 26 carbon acyl chain fits into the A' pocket by adopting a counterclockwise circular curve, as viewed from above the binding groove, filling the pocket. The 18 carbon sphingosine chain adopts a straighter conformation to fit into the C' pocket, and terminates at the end of the binding groove. It is likely that α-GalCer has the maximum lipid chain lengths that are able to fit into the antigen-binding groove of human CD1d.

From x-ray diffraction studies and modeling experiments, it appears that when the $R^2$ group is shorter than the maximum length, the remaining space can be occupied by spacer molecules, which occur naturally in the body and are sufficiently available to occupy vacant spaces in the CD1d molecule. Such spacer molecules include, e.g., lipids. Therefore, compounds of Formula I that include an $R^2$ group that is significantly smaller than what is needed for maximum occupation of the A' channel will still bind well to the CD1d molecule.

Binding studies reported in the literature teach that carbon-carbon double bonds may be substituted for several of the carbon-carbon single bonds on the 26 carbon acyl chain and on the 18 carbon sphingosine chain of α-GalCer, provided that the hydrophobic moieties are still able to occupy the conformations necessary for binding with their respective channels. Some studies have shown, for example, that the channels are able to accept relatively bulky hydrophobic residues, such as phenyl.

In some embodiments, at least one of $R^1$ or $R^2$ comprises at least 1 double bond, or 1, 2 or 3 double bonds. In some embodiments, $R^1$ and/or $R^2$ comprises at least one double bond with Z stereochemistry. For example, $R^2$ can comprise at least 1 double bond that has Z stereochemistry.

In some embodiments, X is

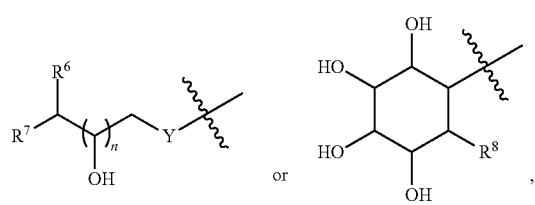

and Y is $CH_2$. In some exemplary embodiments, X is

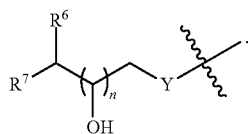

In some embodiments, $R^6$ and $R^7$ are each H. In alternative embodiments, one of $R^6$ or $R^7$ is H and the other is OH.

The compounds of Formula I can exhibit tautomerism. Further, the compounds of Formula I can also contain one or more asymmetric carbon atoms, and can exist as pure stereoisomers or as a mixture of stereoisomers. In some embodiments, the compounds of Formula I exhibit the same stereochemistry as α-GalCer.

Pharmaceutically acceptable salts of the compound of Formula I may be prepared by reacting the compound of Formula I with an appropriate acid or base in the presence of a suitable solvent, as known to one of ordinary skill in the art. Suitable pharmaceutically acceptable salts include salts with suitable bases, such as, alkali metals (e.g., sodium and potassium), and alkaline earth metals, (e.g., calcium and magnesium) salts. The salts of the compound of Formula I can be converted to the free base form using any method known to one skilled in the art.

In some embodiments, the nonglycosidic ceramide is selected from the group consisting of arabinitolceramide, glycerolceramide, threitolceramide, threitolceramide $C_{14}$ acyl, threitol-22-(Z)-ceramide, 4-deoxy-4-phenyl-threitolceramide, 4-deoxy-4-phenyl-threitol-22-(Z)-ceramide, glycerol-phosphateceramide, inositolceramide, inositolceramide $C_{15}$ acyl, myoinositolceramide salt, 4-phenyl threitolceramide, 4-phenyl threitol-22-(Z)-ceramide, threitol-(19Z, 22Z)-ceramide, and mixtures thereof. For example, the nonglycosidic ceramide can include arabinitolceramide, glycerolceramide, threitolceramide, and mixtures thereof (e.g., threitolceramide).

The nonglycosidic ceramide (or combination of ceramides) can be present in the bilayer of the liposome in any amount that provides a liposome having a similar efficacy as a corresponding soluble, nonglycosidic ceramide that is not incorporated within a liposome, or provides a superior efficacy; or provides a therapeutic window (between minimum effective concentration and toxic concentration). In some embodiments, the nonglycosidic ceramide is present in the bilyaer of the liposome in an amount of about 1 wt. % to about 50 wt. %, or about 2 wt. % to about 20 wt. %, or about 2 wt. % to about 10 wt. %, or about 3 wt. % to about 12 wt. %, based on the total weight of the liposome or the lipid bilayer. In some embodiments, the nonglycosidic ceramide is present in an amount of about 1 wt. % to about 30 wt. %, or about 20 wt. % to about 50 wt. %, or about 3 wt. % to about 8 wt. %, or about 4 wt. % to about 13 wt. %, based on the total weight of the liposome or lipid bilayer. For example, the nonglycosidic ceramide can be present in an amount of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, or about 50 wt. %, based on the total weight of the liposome or the lipid bilayer. In some exemplary embodiments, the nonglycosidic ceramide is present is an amount of about 5 wt. % or about 10 wt. %, based on the total weight of the liposome or the lipid bilayer. A weight percentage of nonglycosidic ceramide is chosen to produce an effective immunomodulatory response with minimal toxic side effects. If too little nonglycosidic ceramide is present relative to total lipid, the liposome will not stimulate a desired response. If too much nonglycosidic ceramide is present relative to total lipid, the excess nonglycosidic ceramides will compete for binding sites and may cause the liposomes to block each other from binding. Further, too much nonglycosidic ceramide may result in toxicity issues.

The one to five lipids each can be any lipid that is capable of forming a liposome with the nonglycosidic ceramide described herein, as long as the resulting liposome has at least a similar efficacy as a corresponding soluble nonglycosidic ceramide that is not incorporated within a liposome. The one to five lipids each can independently have a net positive charge (i.e., a cationic lipid), a net negative charge (i.e., an anionic lipid), no charges (i.e, a nonionic lipid), or an equal number of positive and negative charges (i.e., a zwitterionic lipid). The lipids can include those lipids that form a bilayer themselves or with the nonglycosidic ceramide, and those lipids that do not form a bilayer alone, but they can be included as part of a stable bilayer made from one or more other lipids.

A cationic lipid can be included in the liposome if, e.g., the resulting liposome will function as a delivery agent for a negatively-charged bioactive agent, such as for nucleic acids. Other advantages for including a cationic lipid include an increased association with cells due to ionic attraction to the negatively-charged surface of the cell, increased incorporation/association of acidic proteins, and potential for activation of immune cells, thereby enhancing the effect of the nonglycosidic ceramide on the cell.

An anionic lipid can be included in the liposome if, e.g., the resulting liposome will function as a delivery agent for a positively-charged bioactive agent. Other advantages for including an anionic lipid include increased association with the target, increased incorporation/association of basic proteins, and potential for activation of immune cells, thereby enhancing the effect of the nonglycosidic ceramide on the cell.

A nonionic lipid also can be included in the liposome if, e.g., the resulting liposome.

A zwitterionic lipid can be included in the liposome if, e.g., the resulting liposome will function as a delivery agent for a neutral compound. Other advantages for including a zwitterionic lipid include stabilization of the lipid bilayer formation and formation of a permeability barrier allowing for encapsulation of small molecules (e.g., small molecule immunomodulators).

In some embodiments, at least one of the one to five lipids is selected from the group consisting of a sphingolipid; a phospholipid; a sterol; a cationic lipid that is not a sphingolipid, a phospholipid, or a sterol; a neutral lipid that is not a sphingolipid, a phospholipid, or a sterol; a detergent that is not a sphingolipid, a phospholipid, or a sterol; a bioactive lipid that is not a sphingolipid, a phospholipid, or a sterol; coenzyme A, or a derivative of any of the foregoing.

In some embodiments, the sphingolipid is selected from the group consisting of a sphingosine, a ceramide, a sphingomyelin, a ganglioside, a glycosphingolipid, a phosphosphingolipid, a phytosphingosine, a sphingolipid receptor agonist, a sphingolipid receptor antagonist, a sphingolipid metabolism inhibitor, a bioactive ceramide, and derivatives thereof.

In some embodiments, the sphingosine is selected from the group consisting of natural sphingosine, synthetic sphingosine, phosphorylated sphingosine (S1P), and methylated sphingosine.

In some embodiments, the natural sphingosine is D-erythro-sphingosine (e.g., from porcine brain or chicken egg).

In some embodiments, the synthetic sphingosine is selected from the group consisting of sphingosine (d18:1), sphingosine (d17:1), sphingosine (d20:1), L-threo-sphingosine (d18:1), 1-deoxysphingosine, and 1-desoxymethylsphingosine. In some embodiments, the sphinganine is selected from the group consisting of sphinganine (d18:0), sphinganine (d17:0), sphinganine (d20:0), 1-deoxysphinganine, 1-desoxymethylsphinganine, and L-threo-dihydrosphingosine (d18:0) (Safingol). In some embodiments, the phosphorylated sphingosine is selected from the group consisting of sphingosine-1-phosphate (d18:1), sphingosine-1-phosphate (DMA Adduct), sphingosine-1-phosphate (d17:1), sphingosine-1-phosphate (d20:1), sphinganine-1-phosphate (d18:0), sphinganine-1-phosphate (d17:0), and sphinganine-1-phosphate (d20:0). In some embodiments, the methylated sphingosine is selected from the group consisting of monomethyl sphingosine (d18:1), dimethyl sphingosine (d18:1), dimethyl sphingosine (d17:1), trimethyl sphingosine (d18:1), trimethyl sphingosine (d17:1), dimethyl sphinganine (d18:0), trimethyl sphinganine (d18:0), dimethyl sphingosine-1-phosphate (d18:1), and dimethyl sphinganine-1-phosphate (d18:0).

In some embodiments, the ceramide is selected from the group consisting of natural ceramide, synthetic ceramide, a ceramide phosphate, a 1-O-acyl-ceramide, a dihydroceramide, a dihydroceramide phosphate, and a 2-hydroxy ceramide.

In some embodiments, the natural ceramide is ceramide from, for example, porcine brain or egg.

In some embodiments the synthetic ceramide is selected from the group consisting of N-octadecanoyl-D-erythro-sphingosine (C18), N-hexadecanoyl-D-erythro-sphingosine (C16) N-acetoyl-D-erythro-sphingosine (C2 Ceramide, d18:1/2:0), N-butyroyl-D-erythro-sphingosine (C4 Ceramide, d18:1/4:0), N-hexanoyl-D-erythro-sphingosine (C6 Ceramide, d18:1/6:0), N-octanoyl-D-erythro-sphingosine (C8 Ceramide, d18:1/8:0), N-decanoyl-D-erythro-sphingosine (C10 Ceramide, d18:1/10:0), N-lauroyl-D-erythro-sphingosine (C12 Ceramide, d18:1/12:0), N-myristoyl-D-erythro-sphingosine (C14 Ceramide, d18:1/14:0), N-palmitoyl-D-erythro-sphingosine (C16 Ceramide, d18:1/16:0), N-heptadecanoyl-D-erythro-sphingosine (C17 Ceramide, d18:1/17:0), N-stearoyl-D-erythro-sphingosine (C18 Ceramide, d18:1/18:0), N-oleoyl-D-erythro-sphingosine (C18:1 Ceramide, d18:1/18:1(9Z)), N-arachidoyl-D-erythro-sphingosine (C20 Ceramide, d18:1/20:0), N-behenoyl-D-erythro-sphingosine (C22 Ceramide, d18:1/22:0), N-lignoceroyl-D-erythro-sphingosine (C24 Ceramide, d18:1/24:0), N-nervonoyl-D-erythro-sphingosine (C24:1 Ceramide, d18:1/24:1(15Z)), N-acetoyl-D-erythro-sphingosine (C17 base) (C2 Ceramide, d17:1/2:0), N-octanoyl-D-erythro-sphingosine (C17 base) (C8 Ceramide, d17:1/8:0), N-stearoyl-D-erythro-sphingosine (C17 base) (C18 Ceramide, d17:1/18:0), N-oleoyl-D-erythro-sphingosine (C17 base) (C18:1 Ceramide, d17:1/18:1(9Z)), N-arachidoyl-D-erythro-sphingosine (C17 base) (C20 Ceramide, d17:1/20:0), N-lignoceroyl-D-erythro-sphingosine (C17 base) (C24 Ceramide, d17:1/24:0), and N-nervonoyl-D-erythro-sphingosine (C17 base) (C24:1 Ceramide, d17:1/24:1(15Z)).

In some embodiments, the ceramide phosphate is selected from the group consisting of N-acetoyl-ceramide-1-phosphate (ammonium salt) (C2 Ceramide-1-Phosphate, d18:1/2:0), N-octanoyl-ceramide-1-phosphate (ammonium salt) (C8 Ceramide-1-Phosphate, d18:1/8:0), N-lauroyl-ceramide-1-phosphate (ammonium salt) (C12 Ceramide-1-Phosphate, d18:1/12:0), N-palmitoyl-ceramide-1-phosphate (ammonium salt) (C16 Ceramide-1-Phosphate, d18:1/16:0), N-oleoyl-ceramide-1-phosphate (ammonium salt) (C18:1 Ceramide-1-Phosphate, d18:1/18:1(9Z)), N-lignoceroyl-ceramide-1-phosphate (ammonium salt) (C24 Ceramide-1-Phosphate, 18:1/24:0), N-acetoyl-ceramide-1-phosphate (C17 base) (ammonium salt) (C2 Ceramide-1-Phosphate, d17:1/2:0), and N-octanoyl-ceramide-1-phosphate (C17 base) (ammonium salt) (C8 Ceramide-1-Phosphate, d17:1/8:0).

In some embodiments, the 1-O-acyl-ceramide is 1-oleoyl-N-heptadecanoyl-D-erythro-sphingosine N-acetoyl-D-erythro-sphinganine (C2 Dihydroceramide, d18:0/2:0).

In some embodiments, the dihydroceramide is selected from the group consisting of N-hexanoyl-D-erythro-sphinganine (C6 Dihydroceramide, d18:0/6:0), N-octanoyl-D-erythro-sphinganine (C8 Dihydroceramide, d18:0/8:0), N-palmitoyl-D-erythro-sphinganine (C16 Dihydroceramide, d18:0/16:0), N-stearoyl-D-erythro-sphinganine (C18 Dihydroceramide, d18:0/18:0), N-oleoyl-D-erythro-sphinganine (C18:1 Dihydroceramide, d18:0/18:1(9Z)), N-lignoceroyl-D-erythro-sphinganine (C24 Dihydroceramide, d18:0/24:0), and N-nervonoyl-D-erythro-sphinganine-D-erythro-sphinganine (C24:1 Dihydroceramide, d18:0/24:1(15Z)).

In some embodiments, the dihydroceramide phosphate is N-palmitoyl-D-erythro-dihydroceramide-1-phosphate (ammonium salt) (C16 Dihydroceramide-1-Phosphate, d18:0/16:0) or N-lignoceroyl-D-erythro-dihydroceramide-1-phosphate (ammonium salt) (C24 Dihydroceramide-1-Phosphate, d18:0/24:0).

In some embodiments, the 2-hydroxy ceramide is selected from the group consisting of N-(2'-(R)-hydroxylauroyl)-D-erythro-sphingosine (12:0(2R—OH) Ceramide), N-(2'-(S)-hydroxylauroyl)-D-erythro-sphingosine (12:0(2S—OH) Ceramide), N-(2'-(R)-hydroxypalmitoyl)-D-erythro-sphingosine (16:0(2R—OH) Ceramide), N-(2'-(S)-hydroxypalmitoyl)-D-erythro-sphingosine (16:0(2S—OH) Ceramide), N-(2'-(R)-hydroxyheptadecanoyl)-D-erythro-sphingosine (17:0(2R—OH) Ceramide), N-(2'-(S)-hydroxyheptadecanoyl)-D-erythro-sphingosine (17:0(2S—OH) Ceramide), N-(2'-(R)-hydroxystearoyl)-D-erythro-sphingosine (18:0(2R—OH) Ceramide), N-(2'-(S)-hydroxystearoyl)-D-erythro-sphingosine (18:0(2S—OH) Ceramide), N-(2'-(R)-hydroxyoleoyl)-D-erythro-sphingosine (18:1(2R—OH) Ceramide), N-(2'-(S)-hydroxyoleoyl)-D-erythro-sphingosine (18:1(2S—OH) Ceramide), N-(2'-(R)-hydroxyarachidoyl)-D-erythro-sphingosine (20:0(2R—OH) Ceramide), N-(2'-(S)-hydroxylarachidoyl)-D-erythro-sphingosine (20:0(2S—OH) Ceramide), N-(2'-(R)-hydroxybehenoyl)-D-erythro-sphingosine (22:0(2R—OH) Ceramide), N-(2'-(S)-hydroxylbehenoyl)-D-erythro-sphingosine (22:0(2S—OH) Ceramide), N-(2'-(R)-hydroxylignoceroyl)-D-erythro-sphingosine (24:0(2R—OH) Ceramide), N-(2'-(S)-hydroxyllignoceroyl)-D-erythro-sphingosine (24:0(2S—OH) Ceramide), N-(2'-(R)-hydroxynervonoyl)-D-erythro-sphingosine (24:1(2R—OH) Ceramide), and N-(2'-(S)-hydroxylnervonoyl)-D-erythro-sphingosine (24:1(2S—OH) Ceramide).

In some embodiments, the sphingomyelin is selected from the group consisting of a natural sphingomyelin (e.g., from porcine brain, chicken egg, or bovine milk), N-acetyl-D-erythro-sphingosylphosphorylcholine (02:0 SM, d18:1/2:0), N-hexanoyl-D-erythro-sphingosylphosphorylcholine (06:0 SM, d18:1/6:0), N-lauroyl-D-erythro-sphingosylphosphorylcholine (12:0 SM, d18:1/12:0), N-lauroyl-D-erythro-sphinganylphosphorylcholine (12:0 Dihydro SM, d18:0/12:0), N-palmitoyl-D-erythro-sphingosylphosphorylcholine (16:0 SM, d18:1/16:0), N-heptadecanoyl-D-erythro-sphingosylphosphorylcholine (17:0 SM, d18:1/17:0), N-stearoyl-D-erythro-sphingosylphosphorylcholine (18:0 SM, d18:1/18:0), N-oleoyl-D-erythro-sphingosylphosphorylcholine (18:1 SM, d18:1/18:1(9Z)), N-lignoceroyl-D-erythro-sphingosylphosphorylcholine (24:0 SM), N-nervonoyl-D-erythro-sphingosylphosphorylcholine (24:1 SM), sphingosylphosphorylcholine (Lyso SM, d18:1), sphingosylphosphorylcholine (C17 base) (Lyso SM, d17:1), and sphinganine phosphorylcholine (Lyso SM (dihydro), d18:0).

In some embodiments, the ganglioside is selected from the group consisting of GM1 ganglioside ammonium salt (e.g., from ovine brain), GM3 ganglioside ammonium salt (e.g., from bovine milk), GD3 ganglioside ammonium salt (e.g., from bovine milk), and total ganglioside extract ammonium salt (e.g., from porcine brain).

In some embodiments, the glycosphingolipid is selected from the group consisting of a natural glycosphingolipid, a glycosyl sphingolipid, a galactosyl sphingolipid, a lactosyl sphingolipid, a sulfatide, and α-galactosyl ceramide (αGalCer).

In some embodiments, the natural glycosphingolipid is selected from the group consisting of a cerebroside (e.g., from porcine brain), a glucocerebroside (e.g., from soy), a sulfatide (ammonium salt) (e.g., from porcine brain), a GM1 ganglioside (ammonium salt) (e.g., from ovine brain), a ganglioside GM1 (e.g., from ovine brain), and a total ganglioside extract (ammonium salt) (e.g., from porcine brain).

In some embodiments, the glycosyl sphingolipid is selected from the group consisting of D-glucosyl-β1-1'-D-erythro-sphingosine (Glucosyl(β) Sphingosine, d18:1), D-glucosyl-β-1,1' N-octanoyl-D-erythro-sphingosine (C8 Glucosyl(β) Ceramide, d18:1/8:0), D-glucosyl-β-1,1' N-lauroyl-D-erythro-sphingosine (C12 Glucosyl(β) Ceramide, d18:1/12:0), D-glucosyl-β-1,1' N-palmitoyl-D-erythro-sphingosine (C16 Glucosyl(β) Ceramide, d18:1/16:0), D-glucosyl-β-1,1' N-stearoyl-D-erythro-sphingosine (C18 Glucosyl(β) Ceramide, d18:1/18:0), D-glucosyl-β-1,1' N-oleoyl-D-erythro-sphingosine (C18:1 Glucosyl(β) Ceramide, d18:1/18:1(9Z)), and D-glucosyl-β1-1'-N-nervonoyl-D-erythro-sphingosine (C24:1 Glucosyl(β) Ceramide, dl 8:1/24:1(15Z)).

In some embodiments, the galactosyl sphingolipid is selected from the group consisting of D-galactosyl-β1-1'-D-erythro-sphingosine (Galactosyl(β) Sphingosine, d18:1), N,N-dimethyl-D-galactosyl-β1-1'-D-erythro-sphingosine (Galactosyl(β) Dimethyl Sphingosine, d18:1), D-galactosyl-β-1,1' N-octanoyl-D-erythro-sphingosine (C8 Galactosyl(β) Ceramide, d18:1/8:0), D-galactosyl-β-1,1' N-lauroyl-D-erythro-sphingosine (C12 Galactosyl(β) Ceramide, d18:1/12:0), D-galactosyl-β-1,1' N-palmitoyl-D-erythro-sphingosine (C16 Galactosyl(β) Ceramide, d18:1/16:0), and D-galactosyl-β-1,1' N-nervonoyl-D-erythro-sphingosine (C24:1 Galactosyl(β) Ceramide, d18:1/24:1(15Z)).

In some embodiments, the lactosyl sphingolipid is selected from the group consisting of D-lactosyl-β1-1'-D-erythro-sphingosine (Lactosyl(β) Sphingosine, d18:1), D-lactosyl-β-1,1' N-octanoyl-D-erythro-sphingosine (C8 Lactosyl(β) Ceramide, d18:1/8:0), D-lactosyl-β1-1'-N-octanoyl-L-threo-sphingosine (C8 L-threo-Lactosyl(β) Ceramide, d18:1/8:0), D-lactosyl-β-1,1' N-lauroyl-D-erythro-sphingosine (C12 Lactosyl(β) Ceramide, d18:1/12:0), D-lactosyl-β-1,1' N-palmitoyl-D-erythro-sphingosine (C16 Lactosyl(β) Ceramide, d18:1/16:0), D-lactosyl-β-1,1' N-lignoceroyl-D-erythro-sphingosine (C24 Lactosyl(β) Ceramide, d18:1/24:0), and D-lactosyl-β1-1'-N-nervonoyl-D-erythro-sphingosine (C24:1 Lactosyl(β) Ceramide, d18:1/24:1).

In some embodiments, the sulfatide is selected from the group consisting of 3-O-sulfo-D-galactosyl-β1-1'-N-lignoceroyl-D-erythro-sphingosine (ammonium salt) (e.g., from porcine brain), 3-O-sulfo-D-galactosyl-β1-1'-N-lauroyl-D-erythro-sphingosine (ammonium salt) (C12 Mono-Sulfo Galactosyl(β) Ceramide, d18:1/12:0), 3-O-sulfo-D-galactosyl-β1-1'-N-heptadecanoyl-D-erythro-sphingosine (ammonium salt) (C17 Mono-Sulfo Galactosyl(β) Ceramide, d18:1/17:0), 3-O-sulfo-D-galactosyl-β1-1'-N-lignoceroyl-D-erythro-sphingosine (ammonium salt) (C24 Mono-Sulfo Galactosyl(β) Ceramide (d18:1/24:0), 3-O-sulfo-D-galactosyl-β1-1'-N-nervonoyl-D-erythro-sphingosine (ammonium salt) (C24:1 Mono-Sulfo Galactosyl(β) Ceramide, d18:1/24:1), and 3,6-di-O-sulfo-D-galactosyl-β1-1'-N-lauroyl-D-erythro-sphingosine (ammonium salt) (C12 Di-Sulfo Galactosyl(β) Ceramide, d18:1/12:0).

In some embodiments, the phosphospingolipid is selected from the group consisting of D-erythro-sphingosyl phosphoethanolamine (Sphingosyl PE, d18:1), N-lauroyl-D-erythro-sphingosyl phosphoethanolamine (C17 base) (C12 Sphingosyl PE, d17:1/12:0), and D-erythro-sphingosyl phosphoinositol (Sphingosyl PI).

In some embodiments, the phytosphingosine is selected from the group consisting of 4-hydroxysphinganine (*Saccharomyces Cerevisiae*) (D-ribo-Phytosphingosine), 4-hydroxysphinganine (C17 base) (D-ribo-phytosphingosine, C17 base), 4-hydroxysphinganine-N,N-dimethyl (*Saccharo-*

*myces Cerevisiae*) (Phytosphingosine-N,N-Dimethyl), 4-hydroxysphinganine-N,N,N-trimethyl (methyl sulfate salt) (*Saccharomyces cerevisiae*) (Phytosphingosine-N,N,N-Trimethyl), 4-hydroxysphinganine-1-phosphate (*Saccharomyces Cerevisiae*) (D-ribo-Phytosphingosine-1-Phosphate), 4-hydroxysphinganine-N,N-dimethyl-1-phosphate (ammonium salt) (*Saccharomyces Cerevisiae*) (Phytosphingosine-N,N-Dimethyl-1-Phosphate), N-acetoyl 4-hydroxysphinganine (*Saccharomyces Cerevisiae*) (N-02:0 Phytosphingosine), N-octanoyl 4-hydroxysphinganine (*Saccharomyces Cerevisiae*) (N-08:0 Phytosphingosine), N-stearoyl 4-hydroxysphinganine (*Saccharomyces Cerevisiae*) (N-18:0 Phytosphingosine), and 4-hydroxysphinganine-1-phosphocholine (*Saccharomyces Cerevisiae*) (Phytosphingosine Phosphocholine).

In some embodiments, the sphingolipid receptor agonist or antagonist is selected from the group consisting of (S)-phosphoric acid mono-[2-amino-3-(4-octyl-phenylamino)-propyl] ester (VPC 24191), (R)-phosphoric acid mono-[2-amino-2-(6-octyl-1H-benzoimiazol-2-yl)-ethyl] ester (VPC 23153), (R)-phosphoric acid mono-[2-amino-2-(3-octyl-phenylcarbamoyl)-ethyl] ester (VPC 23019), R)-3-Amino-(3-hexylphenylamino)-4-oxobutylphosphonic acid (TFA salt) (W146), and (S)-3-amino-4-(3-hexylphenylamino)-4-oxobutylphosphonic acid (TFA salt) (W140).

In some embodiments, the sphingolipid metabolism inhibitor is selected from the group consisting of 1-deoxysphingosine (m18:1), 1-desoxymethylsphingosine (m17:1), 1-deoxysphinganine (m18:0), 1-deoxymethylsphinganine (m17:0), N-[(1R,2S)-2-hydroxy-1-hydroxymethyl-2-(2-tridecyl-1-cyclopropenyl)ethyl]octanamide (GT-11), 1R,2R-(+)-1-phenyl-2-palmitoylamino-3-N-morpholine-1-propanol (D-threo-PPMP), L-threo-dihydrosphingosine (d18:0) (Safingol), N-lauroyl-1-deoxysphingosine (m18:1/12:0) (N—C12-deoxysphingosine), N-palmitoyl-1-deoxysphingosine (m18:1/16:0) (N—C16-deoxysphingosine), N-nervonoyl-1-deoxysphingosine (m18:1/24:1) (N—C24:1-deoxysphingosine), N-lauroyl-1-deoxysphinganine (m18:0/12:0) (N—C12-deoxysphinganine), N-palmitoyl-1-deoxysphinganine (m18:0/16:0) (N—C16-deoxysphinganine), N-nervonoyl-1-deoxysphinganine (m18:0/24:1) (N—C24:1-deoxysphinganine), N-lauroyl-1-desoxymethylsphingosine (m17:1/12:0) (N—C12-desoxymethylsphingosine), N-palmitoyl-1-desoxymethylsphingosine (m17:1/16:0) (N—C16-desoxymethylsphingosine), N-nervonoyl-1-desoxymethylsphingosine (m17:1/24:1) (N—C24:1-desoxymethylsphingosine), N-lauroyl-1-desoxymethylsphinganine (m17:0/12:0) (N—C12-desoxymethylsphinganine), N-palmitoyl-1-desoxymethylsphinganine (m17:0/16:0) (N—C16-desoxymethylsphinganine), and N-nervonoyl-1-desoxymethylsphinganine (m17:0/24:1) (N—C24:1-desoxymethylsphinganine).

In some embodiments, the bioactive ceramide is selected from the group consisting of D-erythro-2-N-[6'-(1"-pyridinium)-hexanoyl]-sphingosine bromide (C6-Pyridinium-Ceramide), D-erythro-N-[2-(1,3-dihydroxy-4E-octadecene)]-N'-hexadecane-urea (C16-Urea-Ceramide), and D-erythro-N-[2-(1,3-dihydroxy-4E-octadecene)]-N'-hexane-urea-sphingosine (C6-Urea-Ceramide).

In some embodiments, the phospholipid is selected from the group consisting of a phosphatidylcholine, a phosphatidic acid, a phosphatidylethanolamine, a phosphatidylglycerol, a phosphatidylserine, a phosphatidylinositol, an inositol phosphate, a platelet activing factor (PAF), a cardiolipin, an ether phospholipid, a plasmalogen, an oxidized phospholipid, a bis(monoacylglycero)phosphate (BMP), a phospholipid for supported monolayers, and a sterol modified phospholipid.

In some embodiments, the phosphatidylcholine is selected from the group consisting of a natural phosphatidylcholine, a saturated synthetic phosphatidylcholine, an unsaturated synthetic phosphatidylcholine, a mixed acyl phosphatidylcholine, a lyso phosphatidylcholine, and an alkylphosphocholine.

In some embodiments, the natural phosphatidylcholine is L-α-phosphatidylcholine (e.g., from chicken egg, soy, hydrogenated soy, bovine heart, porcine brain, or bovine liver).

In some embodiments, the saturated, synthetic phosphatidylcholine is selected from the group consisting of 1,2-dipropionyl-sn-glycero-3-phosphocholine (03:0 PC), 1,2-dibutyryl-sn-glycero-3-phosphocholine (04:0 PC), 1,2-dipentanoyl-sn-glycero-3-phosphocholine (05:0 PC), 1,2-dihexanoyl-sn-glycero-3-phosphocholine (06:0 PC, DHPC), 1,2-diheptanoyl-sn-glycero-3-phosphocholine (07:0 PC, DHPC), 1,2-dioctanoyl-sn-glycero-3-phosphocholine (08:0 PC), 1,2-dinonanoyl-sn-glycero-3-phosphocholine (09:0 PC), 1,2-didecanoyl-sn-glycero-3-phosphocholine (10:0 PC), 1,2-diundecanoyl-sn-glycero-3-phosphocholine (11:0 PC), 1,2-dilauroyl-sn-glycero-3-phosphocholine (12:0 PC, DLPC), 1,2-ditridecanoyl-sn-glycero-3-phosphocholine (13:0 PC), 1,2-dimyristoyl-sn-glycero-3-phosphocholine (14:0 PC, DMPC), 1,2-dipentadecanoyl-sn-glycero-3-phosphocholine (15:0 PC), 1,2-dipalmitoyl-sn-glycero-3-phosphocholine (16:0 PC, DPPC), 1,2-diphytanoyl-sn-glycero-3-phosphocholine (4ME 16:0 PC), 1,2-diheptadecanoyl-sn-glycero-3-phosphocholine (17:0 PC), 1,2-distearoyl-sn-glycero-3-phosphocholine (18:0 PC, DSPC), 1,2-dinonadecanoyl-sn-glycero-3-phosphocholine (19:0 PC), 1,2-diarachidoyl-sn-glycero-3-phosphocholine (20:0 PC), 1,2-dihenarachidoyl-sn-glycero-3-phosphocholine (21:0 PC), 1,2-dibehenoyl-sn-glycero-3-phosphocholine (22:0 PC), 1,2-ditricosanoyl-sn-glycero-3-phosphocholine (23:0 PC), and 1,2-dilignoceroyl-sn-glycero-3-phosphocholine (24:0 PC).

In some embodiments, the unsaturated, synthetic phosphatidylcholine is selected from the group consisting of 1,2-dimyristoleoyl-sn-glycero-3-phosphocholine (14:1 (Δ9-Cis) PC), 1,2-dimyristelaidoyl-sn-glycero-3-phosphocholine (14:1 (Δ9-Trans) PC), 1,2-dipalmitoleoyl-sn-glycero-3-phosphocholine (16:1 (Δ9-Cis) PC), 1,2-dipalmitelaidoyl-sn-glycero-3-phosphocholine (16:1 (Δ9-Trans) PC), 1,2-dipetroselenoyl-sn-glycero-3-phosphocholine (18:1 (46-Cis) PC), 1,2-dioleoyl-sn-glycero-3-phosphocholine (18:1 (Δ9-Cis) PC, DOPC), 1,2-dielaidoyl-sn-glycero-3-phosphocholine (18:1 (Δ9-Trans) PC), 1,2-dilinoleoyl-sn-glycero-3-phosphocholine (18:2 (Cis) PC, DLPC), 1,2-dilinolenoyl-sn-glycero-3-phosphocholine (18:3 (Cis) PC), 1,2-dieicosenoyl-sn-glycero-3-phosphocholine (20:1 (Cis) PC), 1,2-diarachidonoyl-sn-glycero-3-phosphocholine (20:4 (Cis) PC), 1,2-dierucoyl-sn-glycero-3-phosphocholine (22:1 (Cis) PC), 1,2-didocosahexaenoyl-sn-glycero-3-phosphocholine (22:6 (Cis) PC), and 1,2-dinervonoyl-sn-glycero-3-phosphocholine (24:1 (Cis) PC).

In some embodiments, the mixed acyl phosphatidylcholine is selected from the group consisting of 1-myristoyl-2-palmitoyl-sn-glycero-3-phosphocholine (14:0-16:0 PC), 1-myristoyl-2-stearoyl-sn-glycero-3-phosphocholine (14:0-18:0 PC), 1-palmitoyl-2-acetyl-sn-glycero-3-phosphocholine (16:0-02:0 PC), 1-palmitoyl-2-myristoyl-sn-glycero-3-phosphocholine (16:0-14:0 PC), 1-palmitoyl-2-stearoyl-sn-glycero-3-phosphocholine (16:0-18:0 PC), 1-palmitoyl-2- oleoyl-sn-glycero-3-phosphocholine (16:0-18:1 PC), 1-palmitoyl-2-linoleoyl-sn-glycero-3-phosphocholine (16:0-18:2 PC), 1-palmitoyl-2-arachidonoyl-sn-glycero-3-phosphocholine (16:0-20:4 PC), 1-palmitoyl-2-docosahexaenoyl-sn-glycero-3-phosphocholine (16:0-22:6 PC), 1-stearoyl-2-myristoyl-sn-glycero-3-phosphocholine (18:0-14:0 PC), 1-stearoyl-2-palmitoyl-sn-glycero-3-phosphocholine (18:0-16:0 PC), 1-stearoyl-2-oleoyl-sn-glycero-3-phosphocholine (18:0-18:1 PC), 1-stearoyl-2-linoleoyl-sn-glycero-3-phosphocholine (18:0-18:2 PC), 1-stearoyl-2-arachidonoyl-sn-glycero-3-phosphocholine (18:0-20:4 PC), 1-stearoyl-2-docosahexaenoyl-sn-glycero-3-phosphocholine (18:0-22:6 PC), 1-oleoyl-2-myristoyl-sn-glycero-3-phosphocholine (18:1-14:0 PC), 1-oleoyl-2-palmitoyl-sn-glycero-3-phosphocholine (18:1-16:0 PC), and 1-oleoyl-2-stearoyl-sn-glycero-3-phosphocholine (18:1-18:0 PC).

In some embodiments, the lyso phosphatidylcholine is selected from the group consisting of L-α-lysophosphatidylcholine from chicken egg (Egg Lyso PC), L-α-lysophosphatidylcholine from soy (Soy Lyso PC), 1-alkyl-2-hydroxy-sn-glycero-3-phosphocholine (Lyso PAF, from Heart PC), 1-hexanoyl-2-hydroxy-sn-glycero-3-phosphocholine (06:0 Lyso PC), 1-heptanoyl-2-hydroxy-sn-glycero-3-phosphocholine (07:0 Lyso PC), 1-octanoyl-2-hydroxy-sn-glycero-3-phosphocholine (08:0 Lyso PC), 1-nonanoyl-2-hydroxy-sn-glycero-3-phosphocholine (09:0 Lyso PC), 1-decanoyl-2-hydroxy-sn-glycero-3-phosphocholine (10:0 Lyso PC), 1-undecanoyl-2-hydroxy-sn-glycero-3-phosphocholine (11:0 Lyso PC), 1-lauryl-2-hydroxy-sn-glycero-3-phosphocholine (12:0 Lyso PC), 1-tridecanoyl-2-hydroxy-sn-glycero-3-phosphocholine (13:0 Lyso PC), 1-myristoyl-2-hydroxy-sn-glycero-3-phosphocholine (14:0 Lyso PC), 1-petadecanoyl-2-hydroxy-sn-glycero-3-phosphocholine (15:0 Lyso PC), palmitoyl-2-hydroxy-sn-glycero-3-phosphocholine (16:0 Lyso PC), 1-heptadecanoyl-2-hydroxy-sn-glycero-3-phosphocholine (17:0 Lyso PC), 1-stearoyl-2-hydroxy-sn-glycero-3-phosphocholine (18:0 Lyso PC), 1-oleoyl-2-hydroxy-sn-glycero-3-phosphocholine (18:1 Lyso PC), 1-nonadecanoyl-2-hydroxy-sn-glycero-3-phosphocholine (19:0 Lyso PC), 1-arachidoyl-2-hydroxy-sn-glycero-3-phosphocholine (20:0 Lyso PC), 1-behenoyl-2-hydroxy-sn-glycero-3-phosphocholine (22:0 Lyso PC), 1-lignoceroyl-2-hydroxy-sn-glycero-3-phosphocholine (24:0 Lyso PC), and 1-hexacosanoyl-2-hydroxy-sn-glycero-3-phosphocholine (26:0 Lyso PC).

In some embodiments, the alkylphosphatidylcholine is selected from the group consisting of dodecylphosphocholine (DPC), tetradecylphosphocholine, and hexadecylphosphocholine.

In some embodiments, the phosphatidic acid is selected from the group consisting of a natural phosphatidic acid, a saturated synthetic phosphatic acid, an unsaturated synthetic phosphatidic acid, a lyso phosphatidic acid, a cyclic phosphatidic acid, a lysophosphatidic acid receptor agonist, and a lysophosphatidic acid antagonist.

In some embodiments, the natural phosphatidic acid is L-α-phosphatidic acid (sodium salt) (e.g., from chicken egg or soy).

In some embodiments, the saturated, synthetic phosphatidic acid is selected from the group consisting of 1,2-dihexanoyl-sn-glycero-3-phosphate (sodium salt) (06:0 PA), 1,2-dioctanoyl-sn-glycero-3-phosphate (sodium salt) (08:0 PA), 1,2-didecanoyl-sn-glycero-3-phosphate (sodium salt) (10:0 PA), 1,2-dilauroyl-sn-glycero-3-phosphate (sodium salt) (12:0 PA), 1,2-dimyristoyl-sn-glycero-3-phosphate (sodium salt) (14:0 PA), 1,2-dipalmitoyl-sn-glycero-3-phosphate (sodium salt) (16:0 PA), 1,2-diphytanoyl-sn-glycero-3-phosphate (sodium salt) (4ME 16:0 PA), 1,2-diheptadecanoyl-sn-glycero-3-phosphate (sodium salt) (17:0 PA), and 1,2-distearoyl-sn-glycero-3-phosphate (sodium salt) (18:0 PA).

In some embodiments, the unsaturated, synthetic phosphatidic acid is selected from the group consisting of 1,2-dioleoyl-sn-glycero-3-phosphate (sodium salt (18:1 PA), 1,2-dilinoleoyl-sn-glycero-3-phosphate (sodium salt) (18:2 PA), 1,2-diarachidonoyl-sn-glycero-3-phosphate (sodium salt) (20:4 PA), and 1,2-didocosahexaenoyl-sn-glycero-3-phosphate (sodium salt) (22:6 PA).

In some embodiments, the lyso phosphatidic acid is selected from the group consisting of 1-hexanoyl-2-hydroxy-sn-glycero-3-phosphate (ammonium salt) (06:0 Lyso PA), 1-myristoyl-2-hydroxy-sn-glycero-3-phosphate (ammonium salt) (14:0 Lyso), 1-palmitoyl-2-hydroxy-sn-glycero-3-phosphate (ammonium salt) (16:0 Lyso PA), 1-heptadecanoyl-2-hydroxy-sn-glycero-3-phosphate (ammonium salt) (17:0 Lyso PA), 1-stearoyl-2-hydroxy-sn-glycero-3-phosphate (ammonium salt) (18:0 Lyso PA), 1-oleoyl-2-hydroxy-sn-glycero-3-phosphate (ammonium salt) (18:1 Lyso PA), 1-arachidonoyl-2-hydroxy-sn-glycero-3-phosphate (ammonium salt) (20:4 Lyso PA), 1-O-hexadecyl-2-hydroxy-sn-glycero-3-phosphate (ammonium salt) (C16 LPA), 1-O-octadecyl-2-hydroxy-sn-glycero-3-phosphate (ammonium salt) (C18 LPA), and 1-(9Z-octadecenyl)-2-hydroxy-sn-glycero-3-phosphate (ammonium salt) (C18:1 LPA).

In some embodiments, the cyclic phosphatidic acid is selected from the group consisting of 1-palmitoyl-sn-glycero-2,3-cyclic-phosphate (ammonium salt) (16:0 Cyclic LPA), 1-heptadecanoyl-glycero-2,3-cyclic-phosphate (ammonium salt) (17:0 Cyclic LPA), 1-oleoyl-sn-glycero-2,3-cyclic-phosphate (ammonium salt) (18:1 Cyclic LPA), 1-O-hexadecyl-sn-glycero-2,3-cyclic-phosphate (ammonium salt) (C16 Cyclic LPA), and 1-O-(9Z-octadecenyl)-sn-glycero-2,3-cyclic-phosphate (ammonium salt) (C18:1 Cyclic LPA).

In some embodiments, the lysophosphatidic acid agonist or antagonist is selected from the group consisting of 1-oleoyl-2-methyl-sn-glycero-3-phosphothionate (ammonium salt) (S-OMPT), N-{(1R)-2-hydroxy-1-[(phosphonooxy)methyl]ethyl} (9Z)octadec-9-enamide (ammonium salt) (VPC 31143 (R)), N-{(1S)-2-hydroxy-1-[(phosphonooxy)methyl]ethyl}(9Z)octadec-9-enamide (ammonium salt) (VPC 31144 (S)), (S)-phosphoric acid mono-{2-octadec-9-enoylamino-3-[4-(pyridin-2-ylmethoxy)-phenyl]-propyl} ester (ammonium salt) (VPC 32183 (S)), (S)-phosphoric acid mono-[3-(4-benzyloxy-phenyl)-2-octadec-9-enoylamino-propyl] ester (ammonium salt) (VPC 12249 (S)), (R)-phosphoric acid mono-{2-octadec-9-enoylamino-3-[4-(pyridin-2-ylmethoxy)-phenyl]-propyl} ester (ammonium salt) (VPC 32179 (R)), N-palmitoyl-serine phosphoric acid (ammonium salt) (N—P Serine PA), and N-palmitoyl-tyrosine phosphoric acid (ammonium salt) (N—P Tyrosine PA).

In some embodiments, the phosphatidylethanolamie is selected from the group consisting of a natural phosphatidylethanolamine, a saturated synthethic phosphatidylethanolamine, an unsaturated synthetic phosphatidylethanolamine, a mixed acyl phosphatidylethanolamine, and a lyso phosphatidylethanolamine.

In some embodiments, the natural phosphatidylethanolamine is L-α-phosphatidylethanolamine (e.g., from chicken egg, bovine heart, porcine brain, bovine liver, soy, or *E. coli*) or transphosphatidylated L-α-phosphatidylethanolamine (e.g., from chicken egg) (Egg Trans PE).

In some embodiments, the saturated, synthetic phosphatidylethanolamine is selected from the group consisting of 1,2-dihexanoyl-sn-glycero-3-phosphoethanolamine (06:0 PE), 1,2-dioctanoyl-sn-glycero-3-phosphoethanolamine (08:0 PE), 1,2-didecanoyl-sn-glycero-3-phosphoethanolamine (10:0 PE), 1,2-dilauroyl-sn-glycero-3-phosphoethanolamine (12:0 PE), 1,2-dimyristoyl-sn-glycero-3-phosphoethanolamine (14:0 PE), 1,2-dipentadecanoyl-sn-glycero-3-phosphoethanolamine (15:0 PE), 1,2-dipalmitoyl-sn-glycero-3-phosphoethanolamine (16:0 PE), 1,2-diphytanoyl-sn-glycero-3-phosphoethanolamine (4ME 16:0 PE), 1,2-diheptadecanoyl-sn-glycero-3-phosphoethanolamine (17:0 PE), and 1,2-distearoyl-sn-glycero-3-phosphoethanolamine (18:0 PE).

In some embodiments, the unsaturated, synthetic phosphatidylethanolamine is selected from the group consisting of 1,2-dipalmitoleoyl-sn-glycero-3-phosphoethanolamine (16:1 PE), 1,2-dioleoyl-sn-glycero-3-phosphoethanolamine (18:1 (Δ9-Cis) PE, DOPE), 1,2-dielaidoyl-sn-glycero-3-phosphoethanolamine (18:1 (Δ9-Trans) PE), 1,2-dilinoleoyl-sn-glycero-3-phosphoethanolamine (18:2 PE), 1,2-dilinolenoyl-sn-glycero-3-phosphoethanolamine (18:3 PE), 1,2-diarachidonoyl-sn-glycero-3-phosphoethanolamine (20:4 PE), and 1,2-didocosahexaenoyl-sn-glycero-3-phosphoethanolamine (22:6 PE).

In some embodiments, the mixed acyl phosphatidylethanolamine is selected from the group consisting of 1-palmitoyl-2-oleoyl-sn-glycero-3-phosphoethanolamine (16:0-18:1PE), 1-palmitoyl-2-linoleoyl-sn-glycero-3-phosphoethanolamine (16:0-18:2 PE), 1-palmitoyl-2-arachidonoyl-sn-glycero-3-phosphoethanolamine (16:0-20:4 PE), 1-palmitoyl-2-docosahexaenoyl-sn-glycero-3-phosphoethanolamine (16:0-22:6 PE), 1-stearoyl-2-oleoyl-sn-glycero-3-phosphoethanolamine (18:0-18:1 PE), 1-stearoyl-2-linoleoyl-sn-glycero-3-phosphoethanolamine (18:0-18:2 PE), 1-stearoyl-2-arachidonoyl-sn-glycero-3-phosphoethanolamine (18:0-20:4 PE), and 1-stearoyl-2-docosahexaenoyl-sn-glycero-3-phosphoethanolamine (18:0-22:6 PE).

In some embodiments, the lyso phosphatidylethanolamine is selected from the group consisting of L-α-lysophosphatidylethanolamine (e.g., from chicken egg or porcine brain), 1-myristoyl-2-hydroxy-sn-glycero-3-phosphoethanolamine (14:0 Lyso PE), 1-palmitoyl-2-hydroxy-sn-glycero-3-phosphoethanolamine (16:0 Lyso PE), 1-stearoyl-2-hydroxy-sn-glycero-3-phosphoethanolamine (18:0 Lyso PE), and 1-oleoyl-2-hydroxy-sn-glycero-3-phosphoethanolamine (18:1 Lyso PE).

In some embodiments, the phosphatidylglycerol is selected from the group consisting of a natural phosphatidylglycerol, a saturated synthethic phosphatidylglycerol, an unsaturated synthetic phosphatidylglycerol, a mixed acyl phosphatidylglycerol, a lyso phosphatidylglycerol, and a phosphatidylglycerol platelet activing factor.

In some embodiments, the natural phosphatidylglycerol is L-α-phosphatidylglycerol (sodium salt) (e.g., from *E. coli*, chicken egg, or soy).

In some embodiments, the saturated, synthetic phosphatidylglycerol is selected from the group consisting of 1,2-dihexanoyl-sn-glycero-3-phospho-(1'-rac-glycerol) (sodium salt) (06:0 PG), 1,2-dioctanoyl-sn-glycero-3-phospho-(1'-rac-glycerol) (sodium salt) (08:0 PG), 1,2-didecanoyl-sn-glycero-3-phospho-(1'-rac-glycerol) (10:0 PG), 1,2-dilauroyl-sn-glycero-3-phospho-(1'-rac-glycerol) (12:0 PG), 1,2-dimyristoyl-sn-glycero-3-phospho-(1'-rac-glycerol) (14:0 PG), 1,2-dipentadecanoyl-sn-3-phospho-(1'-rac-glycerol) (15:0 PG), 1,2-dipalmitoyl-sn-glycero-3-phospho-(1'-rac-glycerol) (16:0 PG), 1,2-diphytanoyl-sn-glycero-3-phospho-(1'-rac-glycerol) (4ME 16:0 PG), 1,2-diheptadecanoyl-sn-glycero-3-phospho-(1'-rac-glycerol) (17:0 PG), and 1,2-distearoyl-sn-glycero-3-phospho-(1'-rac-glycerol) (18:0 PG).

In some embodiments, the unsaturated, synthetic phosphatidylglycerol is selected from the group consisting of 1,2-dioleoyl-sn-glycero-3-phospho-(1'-rac-glycerol) (18:1 (Δ9-Cis) PG), 1,2-dielaidoyl-sn-glycero-3-phospho-(1'-rac-glycerol) (18:1 (Δ9-Trans) PG), 1,2-dilinoleoyl-sn-glycero-3-phospho-(1'-rac-glycerol) (18:2 PG), 1,2-dilinolenoyl-sn-glycero-3-phospho-(1'-rac-glycerol) (18:3 PG), 1,2-diarachidonoyl-sn-glycero-3-phospho-(1'-rac-glycerol) (20:4 PG), and 1,2-didocosahexaenoyl-sn-glycero-3-phospho-(1'-rac-glycerol) (22:6 PG).

In some embodiments, the mixed acyl phosphatidylglycerol is selected from the group consisting of, 1-palmitoyl-2-oleoyl-sn-glycero-3-phospho-(1'-rac-glycerol) (16:0-18:1 PG), 1-palmitoyl-2-linoleoyl-sn-glycero-3-phospho-(1'-rac-glycerol) (16:0-18:2 PG), 1-palmitoyl-2-arachidonoyl-sn-glycero-3-phospho-(1'-rac-glycerol) (16:0-20:4 PG), 1-palmitoyl-2-docosahexaenoyl-sn-glycero-3-phospho-(1'-rac-glycerol) (16:0-22:6 PG), 1-stearoyl-2-oleoyl-sn-glycero-3-phospho-(1'-rac-glycerol) (18:0-18:1 PG), 1-stearoyl-2-linoleoyl-sn-glycero-3-phospho-(1'-rac-glycerol) (18:0-18:2 PG), 1-stearoyl-2-arachidonoyl-sn-glycero-3-phospho-(1'-rac-glycerol) (18:0-20:4 PG), and 1-stearoyl-2-docosahexaenoyl-sn-glycero-3-phospho-(1'-rac-glycerol) (18:0-22:6 PG).

In some embodiments, the lyso phosphatidylglycerol is selected from the group consisting of 1-myristoyl-2-hydroxy-sn-glycero-3-phospho-(1'-rac-glycerol) (sodium salt) (14:0 Lyso PG), 1-palmitoyl-2-hydroxy-sn-glycero-3-phospho-(1'-rac-glycerol) (sodium salt) (16:0 Lyso PG), 1-stearoyl-2-hydroxy-sn-glycero-3-phospho-(1'-rac-glycerol) (sodium salt) (18:0 Lyso PG), and 1-oleoyl-2-hydroxy-sn-glycero-3-phospho-(1'-rac-glycerol) (sodium salt) (18:1 Lyso PG).

In some embodiments, the phosphatidylglycerol platelet activing factor is 1-O-hexadecyl-2-acetyl-sn-glycerol (HAG) (C16-02:0 DG).

In some embodiments, the phosphatidylserine is selected from the group consisting of a natural phosphatidylserine, a saturated synthethic phosphatidylserine, an unsaturated synthetic phosphatidylserine, a mixed acyl phosphatidylserine, and a lyso phosphatidylserine.

In some embodiments, the natural phosphatidylserine is L-α-phosphatidylserine (sodium salt) (e.g., from porcine brain or soy).

In some embodiments, the saturated, synthetic phosphatidylserine is selected from the group consisting of 1,2-dihexanoyl-sn-glycero-3-phospho-L-serine (sodium salt) (06:0 PS), 1,2-dioctanoyl-sn-glycero-3-phospho-L-serine (sodium salt) (08:0 PS), 1,2-didecanoyl-sn-glycero-3-phospho-L-serine (sodium salt) (10:0 PS), 1,2-dilauroyl-sn-glycero-3-phospho-L-serine (sodium salt) (12:0 PS), 1,2-dimyristoyl-sn-glycero-3-phospho-L-serine (sodium salt) (14:0 PS), 1,2-dipalmitoyl-sn-glycero-3-phospho-L-serine (sodium salt) (16:0 PS), 1,2-diphytanoyl-sn-glycero-3-phospho-L-serine (sodium salt) (4ME 16:0 PS), 1,2-diheptadecanoyl-sn-glycero-3-phospho-L-serine (sodium salt) (17:0 PS), and 1,2-distearoyl-sn-glycero-3-phospho-L-serine (sodium salt) (18:0 PS).

In some embodiments, the unsaturated, synthetic phosphatidylserine is selected from the group consisting of, 1,2-dioleoyl-sn-glycero-3-phospho-L-serine (sodium salt) (18:1 PS, DOPS), 1,2-dilinoleoyl-sn-glycero-3-phospho-L- serine (sodium salt) (18:2 PS), 1,2-diarachidonoyl-sn-glycero-3-phospho-L-serine (sodium salt) (20:4 PS), and 1,2-didocosahexaenoyl-sn-glycero-3-phospho-L-serine (sodium salt) (22:6 PS).

In some embodiments, the mixed acyl phosphatidylserine is selected from the group consisting of 1-palmitoyl-2-oleoyl-sn-glycero-3-phospho-L-serine (sodium salt) (16:0-18:1 PS, POPS), 1-palmitoyl-2-linoleoyl-sn-glycero-3-phospho-L-serine (sodium salt) (16:0-18:2 PS), 1-palmitoyl-2-arachidonoyl-sn-glycero-3-phospho-L-serine (sodium salt) (16:0-20:4 PS), 1-palmitoyl-2-docosahexaenoyl-sn-glycero-3-phospho-L-serine (sodium salt) (16:0-22:6 PS), 1-stearoyl-2-oleoyl-sn-glycero-3-phospho-L-serine (sodium salt) (18:0-18:1 PS), 1-stearoyl-2-linoleoyl-sn-glycero-3-phospho-L-serine (sodium salt) (18:0-18:2 PS), 1-stearoyl-2-arachidonoyl-sn-glycero-3-phospho-L-serine (sodium salt) (18:0-20:4 PS), and 1-stearoyl-2-docosahexaenoyl-sn-glycero-3-phospho-L-serine (sodium salt) (18:0-22:6 PS).

In some embodiments, the lyso phosphatidylserine is selected from the group consisting of L-α-lysophosphatidylserine (sodium salt) (e.g., from porcine brain), 1-palmitoyl-2-hydroxy-sn-glycero-3-phospho-L-serine (sodium salt) (16:0 Lyso PS), 1-stearoyl-2-hydroxy-sn-glycero-3-phospho-L-serine (sodium salt) (18:0 Lyso PS), and 1-oleoyl-2-hydroxy-sn-glycero-3-phospho-L-serine (sodium salt) (18:1 Lyso PS).

In some embodiments, the phosphatidylinositol is selected from the group consisting of natural phosphatidylinositol, a saturated synthethic phosphatidylinositol, an unsaturated synthetic phosphatidylinositol, a mixed acyl phosphatidylinositol, and a lyso phosphatidylserine.

In some embodiments, the natural phosphatidylinositol is L-α-phosphatidylinositol (sodium salt) (e.g., from bovine liver or soy), L-α-phosphatidylinositol-4-phosphate (ammonium salt) (e.g., from porcine brain) (Brain PI(4)P), or L-α-phosphatidylinositol-4,5-bisphosphate (ammonium salt) (e.g., from porcine brain) (Brain PI(4,5)P2).

In some embodiments, the saturated, synthetic phosphatidylinositol is selected from the group consisting of 1,2-dipalmitoyl-sn-glycero-3-phospho-(1'-myo-inositol) (ammonium salt) (16:0 PI), 1,2-dioleoyl-sn-glycero-3-phospho-(1'-myo-inositol) (ammonium salt) (18:1 PI), 1,2-dioleoyl-sn-glycero-3-phospho-(1'-myo-inositol-3'-phosphate) (ammonium salt) (18:1 PI(3)P, 1,2-dioctanoyl-sn-glycero-3-phospho-(1'-myo-inositol-4'-phosphate) (ammonium salt) (8:0 PI(4)P), 1,2-dioleoyl-sn-glycero-3-phospho-(1'-myo-inositol-5'-phosphate) (ammonium salt) (18:1 PI(5)P), 1,2-dihexanoyl-sn-glycero-3-phospho-(1'-myo-inositol-3',5'-bisphosphate) (ammonium salt) (06:0 PI(3,5)P2), 1,2-dioctanoyl-sn-glycero-3-phospho-(1'-myo-inositol-3',4'-bisphosphate) (ammonium salt) (08:0 PI(3,4)P2), 1,2-dioctanoyl-sn-glycero-3-phospho-(1'-myo-inositol-3',5'-bisphosphate) (ammonium salt) (08:0 PI(3,5)P2), and 1,2-dioctanoyl-sn-glycero-3-phospho-(1'-myo-inositol-4',5'-bisphosphate) (ammonium salt) (08:0 PI(4,5)P2).

In some embodiments, the unsaturated, synthetic phosphatidylinositol 1,2-dioleoyl-sn-glycero-3-phospho-(1'-myo-inositol-3',4'-bisphosphate) (ammonium salt) (18:1 PI(3,4)P2), 1,2-dioleoyl-sn-glycero-3-phospho-(1'-myo-inositol-3',5'-bisphosphate) (ammonium salt) (18:1 PI(3,5) P2), 1,2-dioleoyl-sn-glycero-3-phospho-(1'-myo-inositol-4',5'-bisphosphate) (ammonium salt) (18:1 PI(4,5)P2), 1,2-dihexanoyl-sn-glycero-3-phospho-(1'-myo-inositol-3',4',5'-trisphosphate) (ammonium salt) (06:0 PI(3,4,5)P3), 1,2-dioctanoyl-sn-glycero-3-phospho-(1'-myo-inositol-3',4',5'-trisphosphate) (ammonium salt) (08:0 PI(3,4,5)P3), 1,2-dioleoyl-sn-glycero-3-phospho-(1'-myo-inositol-3',4',5'-trisphosphate) (ammonium salt) (18:1 PI(3,4,5)P3), 1-stearoyl-2-arachidonoyl-sn-glycero-3-phospho-(1'-myo-inositol-3',5'-bisphosphate) (ammonium salt) (18:0-20:4 PI(3,5)P2), 1-stearoyl-2-arachidonoyl-sn-glycero-3-phospho-(1'-myo-inositol-4',5'-bisphosphate) (ammonium salt) (18:0-20:4 PI(4,5)P2), and 1-stearoyl-2-arachidonoyl-sn-glycero-3-phospho-(1'-myo-inositol-3',4',5'-trisphosphate) (ammonium salt) (18:0-20:4 PI(3,4,5)P3).

In some embodiments, the lyso phosphatidylinositol is selected from the group consisting of L-α-lysophosphatidylinositol (sodium salt) (e.g., from bovine liver or soy), and 1-oleoyl-2-hydroxy-sn-glycero-3-phospho-(1'-myo-inositol) (ammonium salt) (18:1 Lyso PI).

In some embodiments, the inositol phosphate is selected from the group consisting of D-myo-inositol-1,3,4-trisphosphate (ammonium salt) (IP3(1,3,4)), D-myo-inositol-1,3,5-triphosphate (ammonium salt) (IP3(1,3,5)), and D-myo-inositol-1,4,5-triphosphate (ammonium salt) (IP3(1,4,5)), and D-myo-inositol-1,3,4,5-tetraphosphate (ammonium salt) (IP4(1,3,4,5)).

In some embodiments, the platelet activating factor or analog thereof is selected from the group consisting of 1-alkyl-2-acetyl-sn-glycero-3-phosphocholine (PAF) (e.g., from heart PC), 1-alkyl-2-hydroxy-sn-glycero-3-phosphocholine (Lyso PAF), (e.g., from heart PC), 1-O-hexadecyl-2-acetyl-sn-glycero-3-phosphocholine (C16-02:0 PC), 1-O-octadecyl-2-acetyl-sn-glycero-3-phosphocholine (C18-02:0 PC), 1-O-hexadecyl-2-hydroxy-sn-glycero-3-phosphocholine (C16 Lyso PAF), 1-O-heptadecyl-2-hydroxy-sn-glycero-3-phosphocholine (C17 Lyso PAF), 1-O-octadecyl-2-hydroxy-sn-glycero-3-phosphocholine (C18 Lyso PAF), 1-O-(9Z)octadecenyl-2-hydroxy-sn-glycero-3-phosphocholine (C18:1 Lyso PAF), 1-O-hexadecyl-2-butyryl-sn-glycero-3-phosphocholine (C16-04:0 PC), 1-O-octadecyl-2-butyryl-sn-glycero-3-phosphocholine (C18-04:0 PC), 1-O-hexadecyl-2-oleoyl-sn-glycero-3-phosphocholine (C16-18:1 PC), 1-O-hexadecyl-2-(8Z,11Z,14Z-eicosatrienoyl)-sn-glycero-3-phosphocholine (C16-20:3 PC), 1-O-hexadecyl-2-arachidonoyl-sn-glycero-3-phosphocholine (C16-20:4 PC), 1-O-hexadecyl-2-docosahexaenoyl-sn-glycero-3-phosphocholine (C16-20:5 PC), 3-O-hexadecyl-2-acetyl-sn-glycero-1-phosphocholine (C16-22:6 PC), 3-O-hexadecyl-2-acetyl-sn-glycero-1-phosphocholine (C16-02:0 PC), 1-palmitoyl-2-acetyl-sn-glycero-3-phosphocholine (16:0-02:0 PC), and 1-myristoyl-2-(4-nitrophenylsuccinyl)-sn-glycero-3-phosphocholine (14:0 NPS PC).

In some embodiments, the cariolipin is selected from the group consisting of natural cardiolipin, a saturated synthethic cardiolipin, an unsaturated synthetic cardiolipin, and a lyso cardiolipin. In some embodiments, the natural cardiolipin is cardiolipin (sodium salt) (e.g., from bovine heart or E. coli). In some embodiments, the saturated, synthetic cardiolipin is 1',3'-bis[1,2-dimyristoyl-sn-glycero-3-phospho]-sn-glycerol (ammonium salt) (14:0 CA, (ammonium salt) or 1',3'-bis[1,2-dimyristoyl-sn-glycero-3-phospho]-sn-glycerol (sodium salt) (14:0 CA, sodium salt). In some embodiments, the unsaturated, synthetic cardiolipin is 1',3'-bis[1,2-dioleoyl-sn-glycero-3-phospho]-sn-glycerol (sodium salt) (18:1 CA). In some embodiments, the lyso cardiolipin is monolysocardiolipin (sodium salt) (e.g., from bovine heart) (Monolyso Heart CA) or dilysocardiolipin (sodium salt) (e.g., from bovine heart) (Dilyso Heart CA).

In some embodiments, the ether phospholipid is selected from the group consisting of 1,2-di-O-hexyl-sn-glycero-3-phosphocholine (06:0 Diether PC), 1,2-di-O-dodecyl-sn-glycero-3-phosphocholine (12:0 Diether PC), 1,2-di-O-tridecyl-sn-glycero-3-phosphocholine (13:0 Diether PC), 1,2- di-O-tetradecyl-sn-glycero-3-phosphocholine (14:0 Diether PC), 1,2-di-O-hexadecyl-sn-glycero-3-phosphocholine (16:0 Diether PC), 1,2-di-O-octadecyl-sn-glycero-3-phosphocholine (18:0 Diether PC), 1,2-di-O-(9Z-octadecenyl)-sn-glycero-3-phosphocholine (18:1 Diether PC), 1-O-octadecyl-2-methyl-sn-glycero-3-phosphocholine (18:0-1:0 Diether PC), 1,2-di-O-phytanyl-sn-glycero-3-phosphocholine (4ME 16:0 Diether PC), 1,2-di-O-phytanyl-sn-glycero-3-phosphoethanolamine (4ME 16:0 Diether PE), 1,2-di-O-phytanyl-sn-glycerol (4ME 16:0 Diether DG), 1,2-di-O-tetradecyl-sn-glycero-3-phospho-(1'-rac-glycerol) (sodium salt) (14:0 Diether PG), 1-O-hexadecyl-sn-glycerol (HG) (1-C16 Ether MG), and 1-O-hexadecyl-2-O-methyl-sn-glycerol (PMG) (1-C16-2-C1 DG).

In some embodiments, the plasmalogen is selected from the group consisting of 1-(1Z-octadecenyl)-2-oleoyl-sn-glycero-3-phosphocholine (C18(Plasm)-18:1 PC), 1-(1Z-octadecenyl)-2-arachidonoyl-sn-glycero-3-phosphocholine (C18(Plasm)-20:4 PC), 1-(1Z-octadecenyl)-2-docosahexaenoyl-sn-glycero-3-phosphocholine (C18(Plasm)-22:6 PC), 1-O-1'-(Z)-octadecenyl-2-hydroxy-sn-glycero-3-phosphocholine (C18(Plasm) LPC), 1-(1Z-octadecenyl)-2-oleoyl-sn-glycero-3-phosphoethanolamine (C18(Plasm)-18:1 PE), 1-(1Z-octadecenyl)-2-arachidonoyl-sn-glycero-3-phosphoethanolamine (C18(Plasm)-20:4 PE), 1-(1Z-octadecenyl)-2-docosahexaenoyl-sn-glycero-3-phosphoethanolamine (C18 (Plasm)-22:6 PE), 1-O-1'-(Z)-octadecenyl-2-hydroxy-sn-glycero-3-phosphoethanolamine (C18(Plasm) LPE), In some embodiments, the oxidized phospholipid is selected from the group consisting of 1-palmitoyl-2-(5'-oxovaleroyl)-sn-glycero-3-phosphocholine (POVPC), 1-palmitoyl-2-(9'-oxo-nonanoyl)-sn-glycero-3-phosphocholine (16:0-09:0 (ALDO) PC), 1-palmitoyl-2-glutaryl-sn-glycero-3-phosphocholine (PGPC), 1-palmitoyl-2-azelaoyl-sn-glycero-3-phosphocholine (PAzPC), 1-hexadecyl-2-azelaoyl-sn-glycero-3-phosphocholine (C16-09:0 (COOH) PC), and (E)-4R-hydroxynonenal-dimethylacetal (4-HNE-dimethylacetal).

In some embodiments, the bis(monoacylglycero)phosphate is selected from the group consisting of bis(monomyristoylglycero)phosphate (S,R Isomer) (ammonium salt) (14:0 BMP (S,R)), bis(monooleoylglycero)phosphate (S,R Isomer) (ammonium salt) (18:1 BMP (S,R)), sn-(3-oleoyl-2-hydroxy)-glycerol-1-phospho-sn-1'-(3'-oleoyl-2'-hydroxy)-glycerol (ammonium salt) (18:1 BMP (S,S)), sn-(1-oleoyl-2-hydroxy)-glycerol-3-phospho-sn-3'-(1'-oleoyl-2'-hydroxy)-glycerol (ammonium salt) (18:1 BMP (R,R)), sn-[2,3-dioleoyl]-glycerol-1-phospho-sn-1'-[2',3'-dioleoyl]-glycerol (ammonium salt) (18:1 BDP (S,S)), sn-(3-myristoyl-2-hydroxy)-glycerol-1-phospho-sn-3'-(1',2'-dimyristoyl)-glycerol (ammonium salt) (14:0 Hemi BMP (S,R)), and sn-(3-oleoyl-2-hydroxy)-glycerol-1-phospho-sn-3'-(1',2'-dioleoyl)-glycerol (ammonium salt) (18:1 Hemi BMP (S,R)).

In some embodiments, the phospholipid for supported monolayers is 1-palmitoyl-2-[16-(acryloyloxy)palmitoyl]-sn-glycero-3-phosphorylcholine (16:0-16:0 (acrylate) PC) or 1-myristoyl-2-(14-carboxymyristoyl)-sn-glycero-3-phosphocholine (14:0-14:0(COOH) PC).

In some embodiments, the sterol modified phospholipid is selected from the group consisting of 1-palmitoyl-2-cholesterylhemisuccinoyl-sn-glycero-3-phosphocholine (PChemsPC), 1-oleoyl-2-cholesterylhemisuccinoyl-sn-glycero-3-phosphocholine (OChemsPC), and 1-palmitoyl-2-cholesterylcarbonoyl-sn-glycero-3-phosphocholine (PChcPC), 1,2-dicholesterylhemisuccinoyl-sn-glycero-3-phosphocholine (DChemsPC).

In some embodiments, the sterol is selected from the group consisting of a natural sterol, a substituted oxysterol, a derivative of a substituted oxysterol, and a vitamin (e.g., 25-OH Vitamin D2 or 25-OH Vitamin D3). In some embodiments, the natural sterol is selected from the group consisting of cholesterol, desmosterol, zymosterol, stigmasterol, lathosterol, lanosterol, lanostenol, 14-demethyl-lanosterol, and cholesterol sulfate.

In some embodiments, the oxysterol or derivative of an oxysterol is A-ring substituted, B-ring substituted, D-ring substituted, side chain substituted, double substituted, cholestanoic acid, cholestenoic acid, deuterated, fluorinated, sulfonated, or fluorescent. In some embodiments, the A-ring substituted oxysterol is selected from the group consisting of 4β-hydroxycholesterol, a cholestanol (e.g., trihydroxycholestanoic acid), and cholestenone. In some embodiments, the B-ring substituted oxysterol is selected from the group consisting of 7-ketocholesterol, 5α,6α-epoxycholestanol, 5β,6β-epoxycholestanol, 7α-hydroxycholesterol, 7β-hydroxycholesterol, 6α-hydroxy-5α-cholestanol, and 7-dehydrocholesterol. In some embodiments, the D-ring substituted oxysterol is selected from the group consisting of 15-ketocholestene, 15-ketocholestane, 15α-hydroxycholestene, 15β-hydroxycholestene, 15α-hydroxycholestane, and 15β-hydroxycholestane. In some embodiments, the side chain substituted sterol is selected from the group consisting of 22(R)-hydroxycholesterol, 22(S)-hydroxycholesterol, 24(R)-hydroxycholesterol, 24(S)-hydroxycholesterol, 24(S),25-epoxycholesterol, 24(R/S),25-epoxycholesterol, 25-hydroxycholesterol, and 27-hydroxycholesterol. In some embodiments, the double substituted oxysterol is selected from the group consisting of 3β,27-dihydroxy-5-cholesten-7-one, 7α,27-dihydroxy-4-cholesten-3-one, 7α,27-dihydroxycholesterol, and 7β,27-dihydroxycholesterol. In some embodiments, the cholestenone is selected from the group consisting of 3β-hydroxy-7-oxo-5-cholestenoic acid, 7α-hydroxy-3-oxo-4-cholestenoic acid, 3β,7α-dihydroxy-5-cholestenoic acid, and 3β,7β-dihydroxy-5-cholestenoic acid.

In some embodiments, at least one lipid of the one to five lipids is a cationic lipid that is not a sphingolipid, a phospholipid, or a sterol. In some embodiments, the cationic lipid is selected from the group consisting of 3β-[N—(N',N'-dimethylaminoethane)-carbamoyl]cholesterol hydrochloride (DC-Cholesterol.HCl), 1,2-dioleoyl-3-trimethylammonium-propane (chloride salt) (18:1 TAP, DOTAP), 1,2-dioleoyl-3-trimethylammonium-propane (methyl sulfate salt) (18:1 TAP, DOTAP, MS Salt), 1,2-dimyristoyl-3-trimethylammonium-propane (chloride salt) (14:0 TAP), 1,2-dipalmitoyl-3-trimethylammonium-propane (chloride salt) (16:0 TAP), 1,2-stearoyl-3-trimethylammonium-propane (chloride salt) (18:0 TAP), Transfection Reagent I (i.e., contains DOTAP:DOPE in 1:1 w/w ratio), 1,2-dioleoyl-3-dimethylammonium-propane (DODAP) (18:1 DAP), 1,2-dimyristoyl-3-dimethylammonium-propane (14:0 DAP), 1,2-dipalmitoyl-3-dimethylammonium-propane (16:0 DAP), 1,2-distearoyl-3-dimethylammonium-propane (18:0 DAP), dimethyldioctadecylammonium (Bromide Salt) (18:0 DDAB), 1,2-dilauroyl-sn-glycero-3-ethylphosphocholine (chloride salt) (12:0 EPC, Cl Salt), 1,2-dimyristoyl-sn-glycero-3-ethylphosphocholine (chloride salt) (14:0 EPC, Cl Salt), 1,2-dimyristoleoyl-sn-glycero-3-ethylphosphocholine (Tf salt) (14:1 EPC, Tf Salt), 1,2-dipalmitoyl-sn-glycero-3-ethylphosphocholine (chloride salt) (16:0 EPC, Cl Salt), 1,2-distearoyl-sn-glycero-3-ethylphosphocholine (chloride salt) (18:0 EPC, Cl Salt), 1,2-dioleoyl-sn-glycero-3-ethylphosphocholine (chloride salt) (18:1 EPC, Cl Salt), and 1-palmitoyl-2-oleoyl-sn-glycero-3-ethylphosphocholine (chloride salt) (16:0-18:1 EPC, Cl Salt).

In some embodiments, at least one lipid of the one to five lipids is a neutral lipid that is not a sphingolipid, a phospholipid, or a sterol. In some embodiments, the neutral lipid is a diacyl glycerol or an analog of a diacyl glycerol, a lysosomal PLA2 substrate, a glycosylated diacyl glycerol, a prostaglandin, a prenol, or a N-acylglycine (NAGly).

In some embodiments, the diacyl glycerol or an analog of a diacyl glycerol is selected from the group consisting of 1,2-dioctanoyl-sn-glycerol (08:0 DG), 1,2-didecanoyl-sn-glycerol (10:0 DG), 1,2-dilauroyl-sn-glycerol (12:0 DG), 1,2-dimyristoyl-sn-glycerol (14:0 DG), 1,2-dipalmitoyl-sn-glycerol (16:0 DG), 1-2-dioleoyl-sn-glycerol (18:1 DG), 1-palmitoyl-2-oleoyl-sn-glycerol (16:0-18:1 DG), 1-stearoyl-2-linoleoyl-sn-glycerol (18:0-18:2 DG), 1-stearoyl-2-arachidonoyl-sn-glycerol (18:0-20:4 DG), 1-stearoyl-2-docosahexaenoyl-sn-glycerol (18:0-22:6 DG), 1-oleoyl-2-acetyl-sn-glycerol (18:1-2:0 DG), 1,2-di-O-phytanyl-sn-glycerol (4ME 16:0 Diether DG), 1,2-dipalmitoyl ethylene glycol (16:0 Ethylene Glycol), and 1-2-dioleoyl ethylene glycol (18:1 Ethylene Glycol).

In some embodiments, the lysosomal PLA2 substrate is selected from the group consisting of 1-O-hexadecyl-sn-glycerol (HG) (1-C16 Ether MG), 1-O-hexadecyl-2-acetyl-sn-glycerol (HAG) (C16-02:0 DG), and 1-O-hexadecyl-2-O-methyl-sn-glycerol (PMG) (1-C16-2-C1 DG).

In some embodiments, the glycosylated diacyl glycerol is 1,2-diacyl-3-O-(α-D-glucopyranosyl)-sn-glycerol (*E. coli*) (MGlc-DAG).

In some embodiments, the prostaglandin is selected from the group consisting of prostaglandin $E_1$ (PGE1), prostaglandin $F_{1\alpha}$(PGF1α), prostaglandin $F_{1\beta}$ (PGF1β), prostaglandin $A_1$ (PGA1), and prostaglandin $B_1$ (PGB1).

In some embodiments, the prenol is selected from the group consisting of Coenzyme Q6 (*S. cerevisiae*) (CoQ6), a dolichol mixture (13~21), and a polyprenol mixture (13~21).

In some embodiments, the N-acylglycine is selected from the group consisting of lauroyl L-carnitine (C12 Carnitine), palmitoyl L-carnitine (C16 Carnitine), oleoyl L-carnitine (C18:1(Δ9-cis)), N-palmitoylglycine, N-oleoylglycine, and N-arachidonoylglycine.

In some embodiments, at least one lipid of the one to five lipids is a detergent that is not a sphingolipid, a phospholipid, or a sterol. In some embodiments, the detergents is a nonionic detergent, a zwitterionic detergent, or an anionic detergent. In some embodiments, the nonionic detergent is selected from the group consisting of 3α-hydroxy-7α,12α-di-((O-β-D-maltosyl)-2-hydroxyethoxy)-cholane, n-dodecyl-β-D-maltoside, n-octyl-β-D-glucoside, and n-nonyl-β-D-glucoside. In some embodiments, the zwitterionic detergent is 3-[(3-Cholamidopropyl)dimethylammonio]-1-propanesulfonate (CHAPS) or 3-[(3-Cholamidopropyl)dimethylammonio]-2-hydroxy-1-propanesulfonate (CHAPSO). In some embodiments, the anionic detergent is cholesteryl hemisuccinate (CHEMS).

In some embodiments, at least one lipid of the one to five lipids is a bioactive lipid that is not a sphingolipid, a phospholipid, or a sterol. In some embodiments, the bioactive lipid is an adjuvant, a liponucleotide, a TLR-4 agonist (e.g., di[3-deoxy-D-manno-octulosonyl]-lipid A (ammonium salt) (Kdo2-Lipid A)), an endocannabinoid/anadamide, a lysyl phosphatidylglycerol, a diacylglycerol pyrophosphate, or an inhibitor of phospholipase D.

In some embodiments, the adjuvant is selected from the group consisting of Lipid A Detoxified (*Salmonella Minnesota* R595), phosphorylated hexaacyl disaccharide (MPLA, PHAD™), D-(+)-trehalose 6,6'-dibehenate (22:0 Trehalose), and dimethyldioctadecylammonium (Bromide Salt) (18:0 DDAB).

In some embodiments, the liponucelotide is 1,2-dipalmitoyl-sn-glycero-3-(cytidine diphosphate) (ammonium salt) (16:0 CDP DG) or 1,2-dioleoyl-sn-glycero-3-(cytidine diphosphate) (ammonium salt) (18:1 CDP DG).

In some embodiments, the endocannabinoid/anadamide is selected from the group consisting of 2-arachidonoyl glycerol (2-AG), 2-oleoyl glycerol (2-OG), 2-O-arachidonyl glyceryl ether (2-AG Ether), 2-O-oleyl glyceryl ether (2-OG Ether), N-palmitoyl L-serine methyl ester (N-16:0 L-Serine), N-palmitoyl L-serine (N-16:0 L-Serine), N-oleoyl L-serine methyl ester (N-18:1 L-Serine MeEster), N-oleoyl L-serine (N-18:1 L-Serine), N-arachidonoyl L-serine methyl ester (N-20:4 L-Serine MeEster), N-arachidonoyl L-serine (N-20:4 L-Serine), 10Z-heptadecenoylethanolamide (C17:1 anandamide), 9Z-octadecenoylethanolamide (C18:1 anandamide), 5Z,8Z,11Z,14Z-eicosatetraenoylethanolamide (C20:4 anandamide), and 1,2-dioleoyl-sn-glycero-3-phosphoethanolamine-N-arachidonoyl (ammonium salt) (18:1 PE-N-20:4).

In some embodiments, the lysyl phosphatidylglycerol is 1,2-dipalmitoyl-sn-glycero-3-[phospho-rac-(3-lysyl(1-glycerol))] (chloride salt) (16:0 Lysyl PG) or 1,2-dioleoyl-sn-glycero-3-[phospho-rac-(3-lysyl(1-glycerol))] (chloride salt) (18:1 Lysyl PG).

In some embodiments, the diacylglycerol pyrophosphate is dioctanoylglycerol pyrophosphate (ammonium salt) (08:0 DGPP) or dioleoylglycerol pyrophosphate (ammonium salt) (18:1 DGPP).

In some embodiments, the inhibitor of phospholipase D is selected from the group consisting of N-(2-{4-[2-oxo-2,3-dihydro-1H-benzo(d)imidazol-1-yl]piperidin-1-yl}ethyl)-2-naphthamide (VU0155056), N-{2-[4-oxo-1-phenyl-1,3,8-triazaspiro(4.5)decan-8-yl]ethyl}quinoline-3-carboxamide (VU0285655-1), and (1R,2R)—N—([S]-1-{4-[5-bromo-2-oxo-2,3-dihydro-1H-benzo(d)imidazol-1-yl]piperidin-1-yl}propan-2-yl)-2-phenylcyclopropanecarboxamide (VU0359595).

In some embodiments at least one lipid of the one to five lipids is a coenzyme A, a saturated acyl coenzyme A, an unsaturated acyl coenzyme A, or a derivative of a coenzyme A. In some embodiments, the saturated acyl coenzyme A is selected from the group consisting of 03:0 Coenzyme A, 04:0 Coenzyme A, 06:0 Coenzyme A, 08:0 Coenzyme A, 10:0 Coenzyme A, 12:0 Coenzyme A, 13:0 Coenzyme A, 14:0 Coenzyme A, 14:0 Ether Coenzyme A, 15:0 Coenzyme A, 16:0 Coenzyme A, 16:0 Ether Coenzyme A, 4ME 16:0 Coenzyme A, 17:0 Coenzyme A, 18:0 Coenzyme A, 18:0 (α-OH) Coenzyme A, 19:0 Coenzyme A, 20:0 Coenzyme A, 21:0 Coenzyme A, 22:0 Coenzyme A, 23:0 Coenzyme A, 24:0 Coenzyme A, 25:0 Coenzyme A, and 26:0 Coenzyme A.

In some the unsaturated acyl coenzyme A is selected from the group consisting of 16:1 (n7) Coenzyme A, 17:1 (n7) Coenzyme A, 18:1 ether Coenzyme A, 18:1(n7) Coenzyme A, 18:1 (n9) Coenzyme A, 18:1 (n12) Coenzyme A, 18:2 (n6) Coenzyme A, 18:3 (n3) Coenzyme A, 18:3 (n6) Coenzyme A, 20:4 Coenzyme A, 20:5 Coenzyme A, 22:6 Coenzyme A, and 24:1 Coenzyme A.

In some embodiments, the derivative of coenzyme A is selected from the group consisting of 12:0 Biotinyl Coenzyme A, 16-NBD-16:0 Coenzyme A, 12:0 Biotinyl Coenzyme A, 16-NBD-16:0 Coenzyme A, 04:0 Pyrene Coenzyme A, and 04:0 Pyrene Coenzyme A.

In some embodiments, the fatty acid portion of any lipid described herein is modified by, for example, halogenation (e.g., bromination or fluorination), biotinylation, oxidation, acetylation, methylation, or a mixture thereof.

In some embodiments, the headgroup of any lipid described herein is modified with, for example, a succinyl group, a glutaryl group, a dodecanoyl group, an amino group (e.g., caproylamine, dodecanoylamine), a thiol (e.g., thioethyl), a maleimido group, a pyridyldithio group, a biotinyl group, a N-cyanide group, a polyalkylene glycol moiety (e.g., methoxypolyethylene glycol, 300-5000 MW), a galloyl group, a dinitrophenyl group, a homocysteine group, a glycosyl group (e.g., lactosyl), a chelator (e.g., N-diethylenetriaminepentaacetic acid (DTPA) or N-(5-amino-1-carboxylpentyl)miniodiacectic acid)succinic acid), or an alkyl phosphate (e.g., phosphatidylmethanol, phosphatidylethanol, phosphatidylpropanol, phosphatidylbutanol, phosphoethanolamine-N-methyl, and phosphoethanolamine-N,N-dimethyl).

In some embodiments, at least one lipid of the one to five lipids is a zwitterionic lipid. A zwitterionic lipid can be included in a liposome if, e.g., the resulting liposome will function as a delivery agent for a neutral compound. A zwitterionic lipid also provides stabilization to the lipid bilayer and forms a permeability barrier that allows for encapsulation of small molecules (e.g., small molecule immunomodulators). The zwitterionic lipid can be any zwitterionic lipid that is capable of forming a liposome with the nonglycosidic ceramide described herein, as long as the resulting liposome has at least a similar efficacy as a corresponding soluble nonglycosidic ceramide that is not incorporated within a liposome. In some embodiments, the zwitterionic lipid is saturated. In some embodiments, the zwitterionic lipid is unsaturated.

In some embodiments, the zwitterionic lipid is selected from the group consisting of a zwitterionic sphingolipid (e.g., a phosphorylated sphingosine, a sphingomyelin, a phosphosphingolipid, a sphingolipid receptor agonist, and a sphingolipid receptor antagonist), a zwitterionic phospholipid (e.g., a phosphatidylcholine, a phosphatidylethanolamine, a phosphatidylserin, a platelet activing factor phospholipid, an ether phospholipid, a plasmalogen, an oxidized phospholipid, a phospholipid for supported monolayers, and a sterol modified phospholipid), and a zwitterionic detergent that is not a sphingolipid or a phospholipid.

In some embodiments, the zwitterionic lipid is a phospholipid. Examples of zwitterionic phospholipids include any of the herein described zwitterionic phosphatidylcholines (e.g., natural; saturated, synthetic; unsaturated, synthetic; mixed acyl; lyso; alkylphosphocholine), zwitterionic phosphatidylethanolamines (e.g., natural; saturated, synthetic; unsaturated, synthetic; mixed acyl; lyso), zwitterionic phosphatidylserines (e.g., natural; saturated, synthetic; unsaturated, synthetic; mixed acyl; lyso), zwitterionic platelet activing factor phospholipids, zwitterionic ether phospholipids, zwitterionic plasmalogens, zwitterionic oxidized phospholipids, zwitterionic phospholipids for supported monolayers, and zwitterionic aterol modified phospholipids. In some embodiments, the zwitterionic phospholipid is a zwitterionic phosphatidylcholine (e.g., natural; saturated, synthetic; unsaturated, synthetic; mixed acyl; lyso; alkylphosphocholine), a zwitterionic phosphatidylethanolamine (e.g., natural; saturated, synthetic; unsaturated, synthetic; mixed acyl; lyso), or a zwitterionic phosphatidylserine (e.g., natural; saturated, synthetic; unsaturated, synthetic; mixed acyl; lyso).

In some embodiments, at least one lipid of the one to five lipids is a zwitterionic phosphatidylcholine, such as, for example, any of the phosphatidylcholine lipids previously described herein. In some exemplary embodiments, the zwitterionic phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), egg phosphatidylcholine (EPC), and mixtures thereof, for example, egg phosphatidylcholine (EPC).

In some embodiments, at least one lipid of the one to five lipids is anionic. An anionic lipid can be included in a liposome if, e.g., the resulting liposome will function as a delivery agent for a positively-charged compound. An anionic lipid also provides increased association with the target, increased incorporation/association of basic proteins, and potential for activation of immune cells, thereby enhancing the effect of the nonglycosidic ceramide on the cell. The anionic lipid can be any anionic lipid that is capable of forming a liposome with the nonglycosidic ceramide described herein, as long as the resulting liposome has a similar efficacy as a corresponding soluble nonglycosidic ceramide that is not incorporated within a liposome. In some embodiments, the anionic lipid is saturated. In some embodiments, the anionic lipid is unsaturated.

In some embodiments, the anionic lipid is selected from the group consisting of an anionic sphingosine (e.g., a dimethyl sphingosine-1-phosphate, a ceramide phosphate, a dihydroceramide phosphate, a ganglioside, and a sulfatide), an anionic phospholipid (e.g., a phosphatidic acid, a phosphatidylglycerol, a phosphatidylinositol, an inositol phosphate, a cardiolipin, a bis(monoacylglycero)phosphate, an anionic detergent that is not a sphingolipid or a phospholipid, and an anionic bioactive lipid, such as, for example, an adjuvant, a liponucleotide, a TLR-4 agonist, and a diacylglycerol pyrophosphate.

In some embodiments, the anionic lipid is a phospholipid. Examples of anionic phospholipids include any of the herein described anionic phosphatidic acids (e.g., natural; saturated, synthetic; unsaturated, synthetic; lyso; cyclic, lysophosphatidic acid receptor agonist; lysophosphatidic acid receptor antagonist), anionic phosphatidylglycercols (e.g, natural; saturated, synthetic; unsaturated, synthetic; mixed acyl; lyso; platelet activing factor phospholipids), and anionic phosphatidylinositols (e.g., natural; saturated, synthetic; unsaturated, synthetic; lyso; inositol phosphates). In some embodiments, the anionic lipid is phosphatidylglycerol. In some exemplary embodiments, the anionic phosphatidylglycerol is selected from the group consisting of 1,2-dierucoyl phosphatidylglycerol (DEPG), 1,2-dilauroyl phosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2-distearoyl phosphatidylglycerol (DSPG), 1-palmitoyl-2- oleoyl phosphatidylglycerol (POPG), egg phosphatidylglycerol (EPG), salts of any of the foregoing (e.g., sodium, ammonium, or sodium/ammonium), and mixtures thereof (e.g., egg phosphatidylglycerol).

The amount of lipid that can be present in the liposome, excluding any nonglycosidic ceramide, is about 50 wt. % to about 99 wt. %, or about 80 wt. % to about 98 wt. %, based on the total weight of the liposome or the lipid bilayer. In some embodiments, the lipid is present in an amount of about 50 wt. % to about 75 wt. %, or about 75 wt. % to about 99 wt. %, or about 60 wt. % to about 80 wt. %, or about 90 wt. % to about 98 wt. %, based on the total weight of the liposome or the lipid bilayer. For example, the lipid can be present in an amount of about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, about 95 wt. %, about 96 wt. %, about 97 wt. %, about 98 wt. %, or about 99 wt. %, based on the total weight of the liposome or the lipid bilayer.

Antigen-Carrying Liposomes

In some embodiments, the liposomes described herein comprise at least one antigen, such as, for example, a viral antigen, a bacterial antigen, a fungal antigen, a tumor antigen, or mixtures thereof. The exact amount of the antigen with respect to the liposome depends on the composition and purpose of the antigen, and can be determined by one skilled in the art. In these embodiments, the liposomes described herein can be used as immunostimulants or adjuvants to produce a protective immune response, such as a B-cell response, an IgG antibody response, a T-cell response, or a CTL response to the administered antigen.

The antigen can be any antigenic material that is suitable for treatment of a particular disease. In exemplary embodiments, the liposome described herein comprises an antigen and is used to treat cancer. The antigen can be a full length protein antigen, a long peptide antigen (i.e, a peptide that comprises at least 25 amino acids, such as 27-75, 25-50, 25-40, or 25-30 amino acids), or a short peptide antigen (i.e., a peptide that comprises 6-25 amino acids, such as 6-25, 8-25, 10-25, or 15-20 amino acids). In these embodiments, the antigen can be a tumor associated peptide or protein that induces or enhances immune response and is derived from tumor associated genes and encoded proteins including, for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomeras, GnTV, Herv-K-mel, Lage-1, Mage-C2, NA-88, /Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, .alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, and TPS. For example, antigenic peptides characteristic of tumors include those listed in International Patent Application Publication No. WO 20000/020581 and U.S. Patent Application Publication No. 2010/0284965, which are each incorporated herein by reference. In some exemplary embodiments, the antigen is a tumor antigen selected from the group consisting of MUC1, MAGE, BAGE, RAGE, CAGE, SSX-2, NY-ESO-1, PRAME, PSMA, tyrosinase, melan-A, and mixtures thereof. In some embodiments, the tumor antigen is selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE and mixtures thereof. In some variations, the tumor antigen is a mammalian protein. In some variations, the tumor antigen is a human protein. In some variations, the full length protein is employed as the antigen. In some variations, peptides comprising an antigenic fragment of these proteins is used as the tumor antigen.

Small, hydrophilic antigens can be encapsulated within the core of the liposome. Small or large hydrophobic antigens can be noncovalently associated (e.g., through hydrophobic interactions) with the nonpolar portion of the lipid bilayer, small or large charged antigens can be attached (e.g., through electrostatic interactions) to a charged portion on the outside of the lipid bilayer, and small or large hydrophobic or hydrophilic antigens also can be covalently linked to any portion of the liposomal membrane.

In embodiments when the liposome described herein is carrying an antigen, the lipid used to form the liposome is dictated by the size and charge of the antigen (e.g., small, hydrophilic, hydrophobic, positively-charged, or negatively-charged antigens).

In embodiments when a positively-charged antigen is noncovalently associated with the liposomal membrane, at least one lipid of the one to five lipids preferably has a net negative charge and is selected from the group consisting of an anionic sphingosine (e.g., a dimethyl sphingosine-1-phosphate, a ceramide phosphate, a dihydroceramide phosphate, a ganglioside, and a sulfatide), an anionic phospholipid (e.g., a phosphatidic acid, a phosphatidylglycerol, a phosphatidylinositol, an inositol phosphate, a cardiolipin, a bis(monoacylglycero)phosphate, an anionic detergent that is not a sphingolipid or a phospholipid, and an anionic bioactive lipid, such as, for example, an adjuvant, a liponucleotide, a TLR-4 agonist, and a diacylglycerol pyrophosphate.

In embodiments when a negatively-charged antigen is noncovalently associated with the liposomal membrane, at least one lipid of the one to five lipids preferably has a net positive charge. In these embodiments, the cation lipid can be cationic sphingosine (e.g., a trimethyl sphingosine, a trimethyl phytosphingosine, and a pyridinium ceramide), a cationic lipid that is not a sphingosine (e.g., 3β-[N—(N',N'-dimethylaminoethane)-carbamoyl]cholesterol hydrochloride (DC-Cholesterol.HCl), 1,2-dioleoyl-3-trimethylammonium-propane (chloride salt) (18:1 TAP, DOTAP), 1,2-dioleoyl-3-trimethylammonium-propane (methyl sulfate salt) (18:1 TAP, DOTAP, MS Salt), 1,2-dimyristoyl-3-trimethylammonium-propane (chloride salt) (14:0 TAP), 1,2-dipalmitoyl-3-trimethylammonium-propane (chloride salt) (16:0 TAP), 1,2-stearoyl-3-trimethylammonium-propane (chloride salt) (18:0 TAP), Transfection Reagent I (i.e., contains DOTAP:DOPE in 1:1 w/w ratio), 1,2-dioleoyl-3-dimethylammonium-propane (DODAP) (18:1 DAP), 1,2-dimyristoyl-3-dimethylammonium-propane (14:0 DAP), 1,2-dipalmitoyl-3-dimethylammonium-propane (16:0 DAP), 1,2-distearoyl-3-dimethylammonium-propane (18:0 DAP), dimethyldioctadecylammonium (Bromide Salt) (18:0 DDAB), 1,2-dilauroyl-sn-glycero-3-ethylphosphocholine (chloride salt) (12:0 EPC, Cl Salt), 1,2-dimyristoyl-sn-glycero-3-ethylphosphocholine (chloride salt) (14:0 EPC, Cl Salt), 1,2-dimyristoleoyl-sn-glycero-3-ethylphosphocholine (Tf salt) (14:1 EPC, Tf Salt), 1,2-dipalmitoyl-sn-glycero-3-ethylphosphocholine (chloride salt) (16:0 EPC, Cl Salt), 1,2-distearoyl-sn-glycero-3-ethylphosphocholine (chloride salt) (18:0 EPC, Cl Salt), 1,2-dioleoyl-sn-glycero-3-ethylphosphocholine (chloride salt) (18:1 EPC, Cl Salt), and 1-palmitoyl-2-oleoyl-sn-glycero-3-ethylphosphocholine (chloride salt) (16:0-18:1 EPC, Cl Salt), and a cationic bioactive lipid (e.g., dimethyldioctadecylammonium (Bromide Salt) (18:0 DDAB), a lysyl phosphatidylglycerol).

Exemplary lipids that can be used to produce a liposome having a bilayer that can non-covalently associate with a hydrophobic antigen include, but are not limited to, phosphatodylglycerol (PG), phosphatidylinositol (PI), phosphatidylserine (PS), cardiolipin and phosphatidic acid (PA).

Adjuvants

In some embodiments, the liposomes described herein further comprise at least one adjuvant, wherein the at least one adjuvant is in the core of the liposome, in the lipid bilayer, covalently attached to the lipid bilayer, non-covalently associated with the lipid bilayer, or combinations thereof. The term "adjuvant" as used herein refers to a substance that enhances the pharmacological effect of a drug or increases the immune response to an antigen. Adjuvants may enhance the immunological response by providing a reservoir of antigen (extracellularly or within macrophages), activating macrophages and stimulating specific sets of lymphocytes. Adjuvants of many kinds are well known in the art. Exemplary adjuvants known in the art include, but are not limited to, mineral salts, e.g., aluminium hydroxide and aluminum or calcium phosphate gels; oil emulsions and surfactant based formulations, e.g., MF59 (microfluidised detergent stabilized oil-in-water emulsion), saponins, including but not limited to, QS21 (purified saponin), QA-21 (a pure saponin purified from *Quillja saponaria* extract), DQS21, described in PCT Publication No. WO 96/33739, QS-7, QS-17, QS-18 and QS-LI (So et al., MOl. Cells, 7:178-186, 1997); AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects and endogenous human immunomodulators, e.g., hGM-CSF or hIL-12 (cytokines that can be administered either as protein or plasmid encoded), Immudaptin (C3d tandem array); inert vehicles, such as gold particles; a congener obtained after purification and acid hydrolysis of *Salmonella* ninnesota Re 595 lipopolysaccharide; ISCOMATRIX adjuvant (a cage-like structure composed of saponin, phosphilipid, and cholesterol, see e.g., Marakovsky et al., Clin. Cancer Res., 10:2879-2890, 2004); incomplete Freund's adjuvant; complete Freund's adjuvant; CpG oligonucleotides (see e.g., Kreig et al., Nature 374: 546-549, 1995) and other immunostimulatory oligonucleotides including poly-IC and poly-ICLC (Hiltonol®); and various water-in-oil emulsions prepared from biodegradeable oils such as squalene and/or tocopherol In some embodiments, the liposomes described herein further comprise a TLR agonist, such as, for example, poly I:C (TLR3), MPL (TLR4), imiquimod (TLR7), R848 (TLR8) or CpG (TLR9) to produce an enhanced immune stimulation and resulting protection from conditions in which it is desirable for the immune system to respond effectively such as infectious disease or cancer.

Lipid Bilayer-Coated Particles

In another aspect, the invention relates to lipid bilayer-coated particles comprising a nonglycosidic ceramide. Poly (D,L-lactide-co-glycolide) (PLGA) encapsulated perfluorocarbon particles coated with DEAE-dextran, poly-L-lysine, and mouse anti-human antibodies against DC-SIGN are described in Srinivas et al., *Biomaterials* 31:7070-7077 (2010), incorporated herein by reference. Lipid bilayer-coated particles that comprise a glycosidic ceramide in the lipid bilayer (e.g., α-GalCer) are described in Banal et al., *Nature Immunology* 11(4):303-314 (2010) and Barral et al., *PNAS* 105(24):8345-8350 (2008), each incorporated herein by reference.

The lipid bilayer coating is comprised of the at least one to five lipids previously described herein and a nonglycosidic ceramide, as previously described herein. The weight percentages and ratios of the one to five lipids and the nonglycosidic ceramide are as previously described herein. The particle can be any particle that can be coated with a lipid bilayer. Nonlimiting examples of the particle include inorganic particles (e.g., silica particles) and organic particles (e.g., acrylic polymer bead, poly-glutamic acid particles, PLGA particles).

In some embodiments, the particle has a diameter of about 20 nm to about 500 nm, 25 nm to about 300 nm, about 50 nm to about 250 nm, about 60 nm to about 200 nm, about 70 nm to about 150 nm, about 75 to nm to about 125 nm, about 75 nm to about 100 nm, for example, about 100 nm. In some embodiments, the liposome has a diameter of about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm, about 260 nm, about 265 nm, about 270 nm, about 275 nm, about 280 nm, about 285 nm, about 290 nm, about 295 nm, or about 300 nm.

Stated another way, in some embodiments the particle has a diameter defined by a size range, with the lower end of the size range being any size selected from about 25 nm, 30 nm, 35 nm, 40 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm; and with the upper end of the size range being any size selected from about 300 nm, 295 nm, 290 nm, 285 nm, 280 nm, 275 nm, 270 nm, 265 nm, 260 nm, 255 nm 250 nm, 245 nm, 240 nm, 235 nm, 230 nm, 225 nm, 220 nm, 215 nm, 210 nm, 205 nm, 200 nm, 195 nm, 190 nm, 185 nm, 180 nm, 175 nm, 170 nm, 165 nm, 160 nm, 155 nm, 150 nm, 145 nm, 144 nm, 143 nm, 142 nm, 141 nm, 140 nm, 139 nm, 138 nm, 137 nm, 136 nm, 135 nm, 134 nm, 133 nm, 132 nm, 131 nm, 130 nm, 129 nm, 128 nm, 127 nm, 126 nm, 125 nm, 124 nm, 123 nm, 122 nm, 121 nm, 120 nm, 119 nm, 118 nm, 117 nm, 116 nm, 115 nm, 114 nm, 113 nm, 112 nm, 111 nm, 110 nm, 109 nm, 108 nm, 107 nm, 106 nm, 105 nm, 104 nm, 103 nm, 102 nm, 101 nm, 100 nm, 99 nm, 98 nm, 97 nm, 96 nm, 95 nm, 94 nm, 93 nm, 92 nm, 91 nm, or 90 nm.

The lipid bilayer of the lipid bilayer-coated particles can further comprise an antigen, adjuvant, or a mixture thereof, as previously described herein.

Methods of Preparing Liposomes

The liposomes described herein can be produced using any method known to one skilled in the art (e.g., solvent dilution method), as long as the method results in the production of liposomes having a diameter and having the other desired properties described herein.

As described by AVANTI® Polar Lipids, Inc, (worldwide web at avantilipids.com), liposomes are formed when thin lipid films or lipid cakes are hydrated and stacks of liquid crystalline bilayers become fluid and swell. The hydrated lipid sheets detach during agitation and self-close to form large, multilamellar vesicles (LMV) which prevents interaction of water with the hydrocarbon core of the bilayer at the edges. After particle formation occurs, their size is reduced through the introduction of energy, such sonic energy (e.g., through sonication) or mechanical energy (e.g., through extrusion). Although the properties of lipid formulations can vary depending on the composition (cationic, anionic, neutral lipid species), the same preparation method can be used for all lipid vesicles regardless of composition. The general elements of the procedure involve preparation of the lipid for hydration, hydration with agitation, and sizing to a homogeneous distribution of vesicles.

Lipids are added to a stock solution of the nonglycosidic ceramide and they are mixed in an organic solvent to assure a homogeneous mixture of lipids and to obtain a clear lipid solution. This process is typically accomplished using chloroform or chloroform:methanol mixtures. Alternatively, the lipid(s) can be dissolved in tert-butanol or cyclohexane. The lipid solutions are typically prepared using a concentration of about 10 mg to about 20 mg of lipid per mL of organic solvent, although higher concentrations may be used if the lipid solubility and mixing are acceptable. After the lipids are thoroughly mixed in the organic solvent, the solvent is removed to yield a lipid film. If the volume of the organic solvent in the lipid solution is small (<1 mL), the solvent may be evaporated using a dry nitrogen or argon stream in a fume hood. If the volume of the organic solvent in the lipid solution is large, the organic solvent can be removed by rotary evaporation, which yields a thin lipid film on the sides of a round bottom flask. The lipid film is thoroughly dried to remove residual organic solvent by placing the vial or flask on a vacuum pump overnight. The lipid solution is transferred to containers that can withstand sudden temperature changes without cracking, and then frozen either by placing the containers on a block of dry ice or by swirling the container in a dry ice-acetone or alcohol (e.g., ethanol or methanol) bath. After freezing completely, the frozen lipid cake is placed on a vacuum pump and lyophilized until dry (e.g., about 1 to about 3 days, depending on volume). The thickness of the lipid cake should be no more than the diameter of the container being used for lyophilization. Dry lipid films or cakes can be removed from the vacuum pump, the container tightly closed and taped, and then stored frozen until ready to hydrate.

Hydration of the dry lipid film/cake is accomplished by adding an aqueous medium to the container of dry lipid and then agitating the container. The temperature of the hydrating medium should be above the gel-liquid crystal transition temperature (Tc or Tm) of the lipid with the highest Tc before adding it to the dry lipid. After addition of the hydrating medium, the lipid suspension should be maintained above the Tc for the duration of the hydration period. For high transition lipids, agitation of the suspension, while maintaining the suspension above the Tc, can occur by transferring the lipid suspension to a round bottom flask, placing the flask on a rotory evaporation system without a vacuum, and spinning the round bottom flask in a warm water bath that is at a temperature above the Tc of the lipid suspension. Use of a rotary evaporation apparatus allows the lipid to hydrate in its fluid phase with adequate agitation. Although, hydration time may slightly differ among lipid species and structure, a hydration time of about 1 hour with vigorous shaking, mixing, or stirring is typically recommended. Optionally, the vesicle suspension is allowed to stand overnight (i.e., aging) prior to downsizing the vesicles, which makes the sizing process easier and improves the homogeneity of the size distribution. Aging is not recommended for high transition lipids because lipid hydrolysis increases with elevated temperatures. The hydration medium is generally determined by the application of the lipid vesicles. Suitable hydration media include distilled water, buffer solutions, saline, and nonelectrolytes such as sugar solutions. In embodiments where the resulting liposomes comprise antigens encapsulated within their aqueous cores, the hydration media includes one or more antigens. The concentration of the one or more antigens in the hydration media depends on the antigens used and can be determined by one skilled in the art. Methods of encapsulating antigens in liposomes are known to one skilled in the art and described in, for example, Gregoriadis, "Liposome Technology: Interactions of Liposomes with the Biological Mili," $3^{rd}$ ed., Informa Healthcare USA, Inc., New York, N.Y. (2007), incorporated herein by reference.

Physiological osmolality (290 mOsm/kg) can be used for in vivo applications (e.g., 0.9% saline, 5% dextrose, and 10% sucrose). During hydration some lipids form complexes unique to their structure. For example, highly charged lipids can form a viscous gel when hydrated with low ionic strength solutions. This problem can be alleviated by addition of salt or by downsizing the lipid suspension. Poorly hydrating lipids, such as phosphatidylethanolamine, have a tendency to self aggregate upon hydration. Lipid vesicles containing more than about 60 mol % phosphatidylethanolamine form particles having a small hydration layer surrounding the vesicle. The small hydration layer is insufficient to allow the particles to repel each other when they are in close proximity, and the two membranes fall into an energy well where they adhere and form aggregates. The aggregates settle out of solution as large flocculates. These flocculates will disperse on agitation but reform upon sitting.

The product of hydration is a large, multilamellar vesicle (LMV) analogous in structure to an onion, with each lipid bilayer separated by a water layer. The spacing between lipid layers is dictated by composition with poly-hydrating layers being closer together than highly charged layers, which separate based on electrostatic repulsion. Once a stable, hydrated LMV suspension has been produced, the particles can be downsized by a variety of techniques, One method of downsizing LMVs is by using sonic energy, for example, by sonication. Disruption of LMV suspensions by sonication typically produces small, unilamellar vesicles (SUV) with diameters in the range of about 15 to about 50 nm. The most common instrumentation for the preparation of sonicated particles are bath and probe tip sonicators, although cup-horn sonicators can be used as well. Probe tip sonicators can have the disadvantages of causing overheating of the lipid suspension, which results in degradation. Sonication tips also can release titanium particles into the lipid suspension that must be removed by centrifugation prior to use. Use of bath sonicators avoids these problems. Bath sonication of an LMV dispersion is accomplished by placing a test tube containing the suspension in a bath sonicator (or placing the tip of the sonicator in the test tube) and sonicating for 5-10 minutes above the Tc of the lipid. The lipid suspension should begin to clarify to yield a slightly hazy transparent solution. The haze is due to light scattering induced by residual large particles remaining in the suspension. These particles can be removed by centrifugation to yield a clear suspension of SUV. Mean size and distribution of the SUV is influenced by composition and concentration, temperature, sonication time and power, volume, and sonicator tuning. Due to the high degree of curvature of these membranes, SUV are inherently unstable and will spontaneously fuse to form larger vesicles when stored below their phase transition temperature.

Another method of downsizing LMVs is through extrusion. Lipid extrusion is a technique in which a lipid suspension is forced through a polycarbonate filter with a defined pore size to yield particles having a diameter near the pore size of the filter used. Prior to extrusion through the final pore size, LMV suspensions are disrupted either by several freeze-thaw cycles or by prefiltering the suspension through a larger pore size (typically about 0.2 μm to about 1.0 μm). Disruption of the LMV suspensions before extruding them through a final pore size helps prevent the membranes from fouling and improves the homogeneity of the size distribution of the final suspension. As with all procedures for downsizing LMV dispersions, the extrusion should be done at a temperature above the Tc of the lipid. Attempts to extrude below the Tc are typically unsuccessful because the membrane has a tendency to foul with rigid membranes, which cannot pass through the pores. Extrusion through filters with 100 nm pores typically yields large, unilamellar vesicles (LUV) with a mean diameter of 120-140 nm. Mean particle size also depends on lipid composition and is reproducible from batch to batch.

Section 5.3 of Gad, Pharmaceutical Manufacturing Handbook: Production and Processes, John Wiley & Sons, Inc., Hoboken, N.J. (2008), incorporated herein by reference, also provides examples of liposome preparation methods (e.g., sonication, homogenization, dehydrated-rehydrated vesicle (DRV), reverse-phase evaporation (REV), and extrusion). Colas et al., Micron 38:841-847 (2007), incorporated herein by reference, describes liposome preparation using the Mozafari method. Other methods for producing liposomes are described in Riaz, Pakisant Journal of Pharmaceutical Sciences 19(1):65-77 (1996), incorporated herein by reference.

In some exemplary embodiments, an extruder (e.g., LIPEX™ by Northern Lipids) is used to form homogeneous populations of the liposomes described herein. In this process, an aqueous suspension of lipids is forced at about 100 to about 700 psi through a polycarbonate filter with a defined pore size at a controlled temperature.

The size of the liposomes described herein can be determined using, for example, dynamic light scattering.

Exemplary Liposome Embodiments

In some embodiments, provided herein is a liposome comprising (a) a nonglycosidic ceramide present in an amount of about 1 wt. % to about 20 wt. %, (b) a first lipid present in an amount of about 15 wt. % to about 55 wt. %, and (c) a second lipid present in an amount of about 35 wt. % to about 75 wt. %, based on the total weight of the liposome or the lipid bilayer. In some embodiments, the liposome has a diameter less than about 100 nm, as previously described herein. In some embodiments, the liposome has a diameter of about 50 nm to about 150 nm, as previously described herein.

The nonglycosidic ceramide can be any nonglycosidic ceramide known to one skilled in the art, as previously described herein. In some embodiments, the nonglycosidic ceramide is a compound of Formula I or a pharmaceutically acceptable salt thereof, as previously described herein. In some embodiments, the nonglycosidic ceramide is selected from the group consisting of arabinitolceramide, glycerolceramide, threitolceramide, threitolceramide $C_{14}$ acyl, threitol-22-(Z)-ceramide, 4-deoxy-4-phenyl-threitolceramide, 4-deoxy-4-phenyl-threitol-22-(Z)-ceramide, glycerol-phosphateceramide, inositolceramide, inositolceramide $C_{15}$ acyl, myoinositolceramide salt, 4-phenyl threitolceramide, 4-phenyl threitol-22-(Z)-ceramide, threitol-(19Z,22Z)-ceramide, and mixtures thereof. For example, the nonglycosidic ceramide can include arabinitolceramide, glycerolceramide, threitolceramide, and mixtures thereof (e.g., threitolceramide).

In some embodiments, the nonglycosidic ceramide is present in the bilayer of the liposome in an amount of about 1 wt. % to about 50 wt. %, based on the total weight of the liposome or the lipid bilayer, as previously described herein. In some embodiments, the nonglycosidic ceramide is present in an amount of about 2 wt. % to about 20 wt. %, or about 3 wt. % to about 12 wt. %, based on the total weight of the liposome or the lipid bilayer. In some embodiments, the nonglycosidic ceramide is present in an amount of about 1 wt. % to about 30 wt. %, or about 20 wt. % to about 50 wt. %, or about 3 wt. % to about 8 wt. %, or about 4 wt. % to about 13 wt. %, based on the total weight of the liposome or the lipid bilayer. For example, the nonglycosidic ceramide can be present in an amount of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, or about 50 wt. %, based on the total weight of the liposome or the lipid bilayer. In some exemplary embodiments, the nonglycosidic ceramide is present is an amount of about 5 wt. % or about 10 wt. %, based on the total weight of the liposome or the lipid bilayer.

The first lipid and the second lipid each can independently be a cationic lipid, an anionic lipid, a nonionic lipid, or a zwitterionic lipid, as previously described herein. In some embodiments, the first lipid is a zwitterionic lipid. The first lipid can be any zwitterionic lipid described herein, such as, for example a zwitterionic phospholipid. In some embodiments, the first lipid is a zwitterionic phosphatidylcholine. In some exemplary embodiments, the zwitterionic phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), egg phosphatidylcholine (EPC), and mixtures thereof, for example, egg phosphatidylcholine (EPC).

The first lipid can be present in an amount of about 5 wt. % to about 75 wt. %, or about 15 wt. % to about 55 wt. %, for example, about 20 wt. % to about 30 wt. %, based on the total weight of the liposome or the lipid bilayer. In some embodiments, the first lipid is present in an amount of about 5 wt. % to about 25 wt. %, or about 10 wt. % to about 35 wt. %, or about 25 wt. % to about 45 wt. %, or about 50 wt. % to about 65 wt. %, or about 55 wt. % to about 75 wt. %, based on the total weight of the liposome or the lipid bilayer. For example, the first lipid can be present in an amount of about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, or about 75 wt. %, based on the total weight of the liposome or the lipid bilayer. In some exemplary embodiments, the first lipid is present in an amount of about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, or about 30 wt. %, based on the total weight of the liposome or the lipid bilayer.

In some embodiments, the second lipid is an anionic lipid. The second lipid can be any anionic lipid described herein, such as, for example, an anionic phospholipid. In some embodiments, the second lipid is an anionic phosphatidylglycerol. In some exemplary embodiments, the second lipid is selected from the group consisting of 1,2-dierucoyl phosphatidylglycerol (DEPG), 1,2-dilauroylphosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2-distearoyl phosphatidylglycerol (DSPG), 1-palmitoyl-2-oleoyl phosphatidylglycerol (POPG), egg phosphatidylglycerol (EPG), salts of any of the foregoing (e.g., sodium, ammonium, or sodium/ammonium), and mixtures thereof (e.g., egg phosphatidylglycerol).

The second lipid can be present in an amount of about 20 wt. % to about 90 wt. %, or about 35 wt. % to about 75 wt. %, such as, for example, about 65 wt. % to about 75 wt. %, based on the total weight of the liposome or the lipid bilayer. In some embodiments, the second lipid is present in an amount of about 25 wt. % to about 45 wt. %, or about 30 wt. % to about 65 wt. %, or about 45 wt. % to about 75 wt. %, or about 50 wt. % to about 85 wt. %, based on the total weight of the liposome or the lipid bilayer. For example, the second lipid can be present in an amount of about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, or about 90 wt. %, based on the total weight of the liposome or the lipid bilayer.

In some embodiments, the liposome comprises at least three, at least four, or five lipids, as previously described herein.

It has surprisingly been found that liposomes containing egg phosphatidylcholine (EPC) and egg phosphatidylglycerol (EPG) in a weight ratio of about 0.4 to about 3.5, for example, about 0.5:2.0, or about 1:2.5, or about 0.5:4, or about 1:3, and a nonglycosidic ceramide, e.g., threitolceramide, in a weight ratio to total lipid of about 1:99 to about 30:70, for example about 2:98, 3:97, 4:96, 5:95, 6:94, 7:93, 8:92, 9:91, 10:90, 11:89, 12:88, 13:87, 14:86. 15:85, 16:84, 17:83, 18:82, 19:81, 20:80, 21:79, 22:78, 23:77, 24:76, 25:75, 26:74, 27:73, 28:72, 29:71, or 30:70 provide superior results with respect to sensitization of murine and human iNKT cells and potent anti-tumor responses in animal models. In some exemplary embodiments, the liposomes described herein comprise an EPC:EPG weight ratio of about 1:3 and a weight ratio of nonglycosidic ceramide to total lipid of about 5:95 or about 10:90.

The EPC:EPG:threitolceramide (TC) liposomes described herein provide superior ability to activate murine invariant natural killer cells (iNKT) and human cells, as measured by IFNγ release, when compared to liposomes comprising either dimethyldioctadecyl ammonium bromide (DDAP) or cholesterol (CHOL) in place of EPG. For example, EPC:EPG:TC and EPC:DDAB:TC liposomal formulations were both able to activate iNKT cells to the same extent as soluble threitolceramide, while a EPC:CHOL:TC liposomal formulation was not (FIG. 1A). The EPC:DDAB:TC formulations had the disadvantage of appearing to aggregate on cultured cells.

Figure 2:
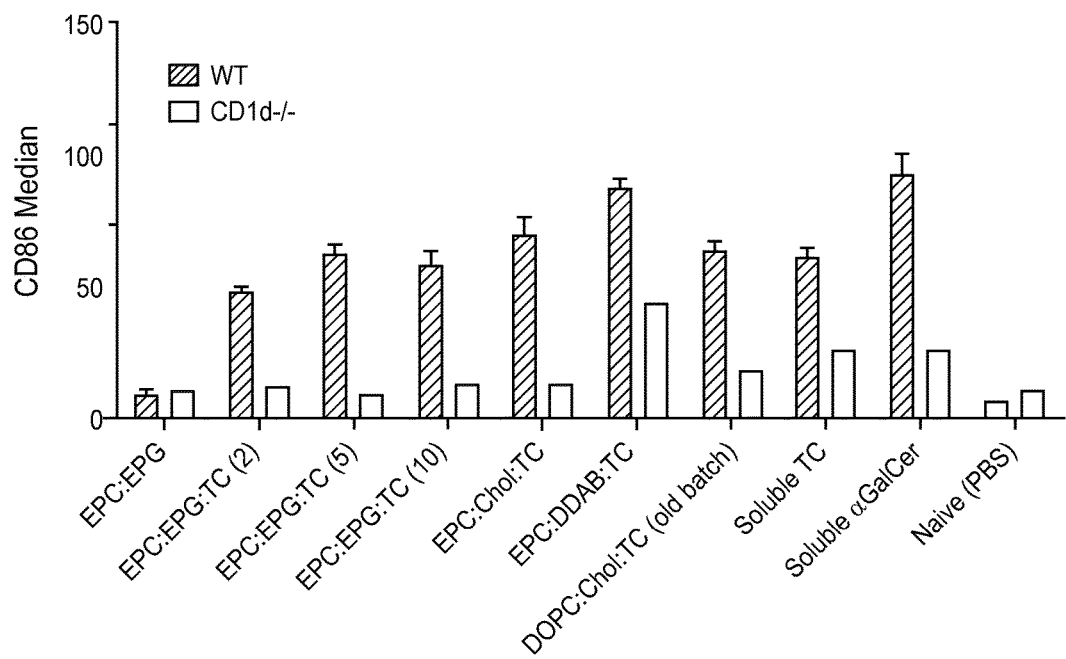
FIG. 2 shows a graph indicating that the non-glycosidic ceramide-containing liposomes induced dendritic cell maturation in vivo, as measured by CD86 expression, with much greater CD86 expression observed in wild-type mice than CD1d$^{-/-}$ (NKT-deficient) mice.

The liposomes described herein also provide superior dendritic cell (DC) maturation, as measured by CD86 and CD40 release, and iNKT cell activation, as measured by IL-4 and IFNγ release when administered in vivo. Although all of the tested threitolceramide-containing liposomal formulations were able to induce DC maturation to the same extent as soluble threitolceramide, the EPC:DDAB:TC liposomal formulation also induced DC maturation in CD1d–/– mice (FIG. 2).

The liposomes described herein were also able to provide superior dendritic cell maturation when administered in vitro (see FIGS. 5-9). Results provided in FIG. 4 indicate that the EPC:EPG:TC formulation, particularly at 10% threitolceramide, was superior to all tested formulations (and easier to handle than EPC:DDAB:TC, data not shown).

Figure 10:
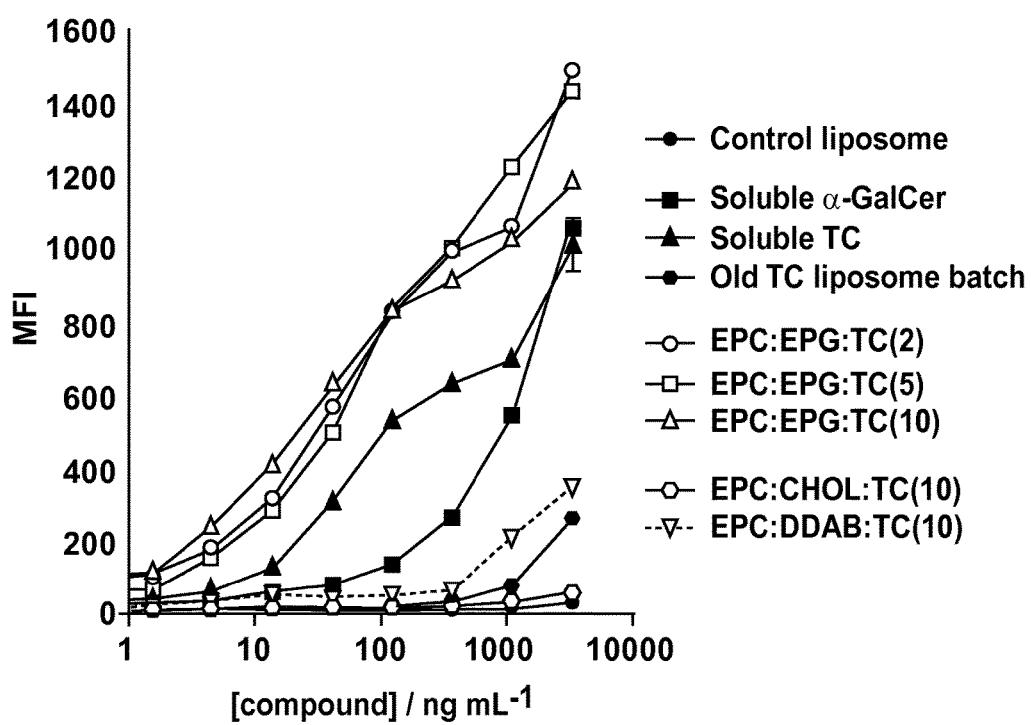
FIG. 10 is a graph showing the superior binding of EPC:EPG:TC formulation to iNKT TCR tetramer as determined by a human C1R.CD1d binding assay.

When the liposomes described herein were tested for their effect on iNKT T-Cell Receptor (TCR) priming in vitro, the EPC:EPG:TC liposomal formulation was found to bind with the greatest efficiency to the iTCR, and better than soluble threitolceramide. In contrast, the EPC:EPG:CHOL and EPC:EPG:DDAB liposomal formulations bound weakly to the iTCR in comparison to the EPC:EP:TC formulation and soluble threitolceramide (FIG. 10).

In some embodiments, the liposome in this embodiment further comprises a positively-charged antigen, as previously described herein. The antigen can be a full length protein antigen, a long peptide antigen, or a short peptide antigen, as previously described herein. In exemplary embodiments, the liposome comprises a positively-charged antigen and is used to treat cancer. In these embodiments, the positively-charged antigen can be a positively-charged tumor associated peptide or protein that induces or enhances an immune response and is derived from tumor associated genes and encoded proteins. In some embodiments, the tumor antigen is selected from the group consisting of MUC1, MAGE, BAGE, RAGE, CAGE, SSX-2, NY-ESO-1, PRAME, PSMA, tyrosinase, melan-A, and mixtures thereof. In some embodiments, the tumor antigen is selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof.

In some exemplary embodiments, the positively-charged antigen is NY-ESO-1. The NY-ESO-1 can be the full length protein, a long peptide, or a short peptide. In some embodiments, NY-ESO-1 is SLLMWITQC (SEQ ID NO: 2), or a variant thereof, as disclosed in U.S. Patent Application Publication No. 2006/0094661, incorporated herein by reference. A variant of NY-ESO-1 can include, for example, a peptide comprising 1 or more amino acid substitutions of SEQ ID NO: 2. One, two, or three substitutions are specific embodiments contemplated. The substituted NY-ESO-1 preferably still generates an immune response to tumors that express the relevant naturally occurring tumor antigen. Amino acid substitutions in variant NY-ESO-1 may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

The substitution can include a standard amino acid substitution, a non-standard amino acid substitution, or both. A non-standard amino acid substitution can include, for example, Tyr, Val, Leu, Ala, Ile, Met, Nle, Nva, Trp, Phe, Asp, Asn, Ser, Abu, and D-stereoisomer of a standard amino acid. In some embodiments, the substitution can include a modified terminal amino acid. For example, the terminal amino acid can be an amidated C-terminal amino acid or the addition of an amino acid to the C-terminus of the peptide. Examples of variants of NY-ESO-1 can be found in U.S. Patent Application Publication No. 2006/0094661, the disclosure which is incorporated by reference.

In these embodiments, the NY-ESO-1 can be present in an amount of about 1 µg to about 1 mg, e.g., about 1 µg, about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 420 µg, about 430 µg, about 440 µg, about 450 µg, about 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, about 600 µg, about 610 µg, about 620 µg, about 630 µg, about 640 µg, about 650 µg, about 660 µg, about 670 µg, about 680 µg, about 690 µg, about 700 µg, about 710 µg, about 720 µg, about 730 µg, about 740 µg, about 750 µg, about 760 µg, about 770 µg, about 780 µg, about 790 µg, about 800 µg, about 810 µg, about 480 µg, about 830 µg, about 840 µg, about 850 µg, about 860 µg, about 870 µg, about 880 µg, about 890 µg, about 900 µg, about 910 µg, about 920 µg, about 930 µg, about 940 µg, about 590 µg, about 960 µg, about 970 µg, about 980 µg, about 990 µg, or about 1000 µg per 2 mg of the liposome. In some embodiments, the NY-ESO-1 is present in an amount of about 1 µg to about 200 µg, or about 300 µg to about 600 µg, or about 700 µg to about 800 µg, or about 100 µg to about 500 µg, or about 500 µg to about 800 µg, about 10 µg to about 100 µg per 2 mg of liposome. In some exemplary embodiments, the NY-ESO-1 is present in an amount of about 400 µg per 2 mg of liposome.

Pharmaceutical Compositions and Routes of Administration

In some embodiments, described herein is a composition comprising a liposome described herein and pharmaceutically acceptable diluent, carrier, excipient, or mixtures thereof. Remington's Pharmaceutical Sciences, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the composition is sterile and has a purity level of, for example, at least about 90%, at least about 91%, at least about 92%, at least about 93%, at least about 94%, at least about 95%, at least about 96%, at least about 97%, at least about 98% or at least about 99%.

In some embodiments, the composition comprises a liposome described herein present in the composition in a concentration of about 0.5 mg/mL to about 30 mg/mL (e.g., about 1 mg/mL to about 20 mg/mL (e.g., about 1 mg/mL, about 2 mg/mL, about 3 mg/mL, about 4 mg/mL, about 5 mg/mL, about 6 mg/mL, about 7 mg/mL, about 8 mg/mL, about 8 mg/mL, about 10 mg/mL, about 11 mg/mL, about 12 mg/mL, about 13 mg/mL, about 14 mg/mL about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL about 25 mg/mL, about 26 mg/mL, about 27 mg/mL, about 28 mg/mL, about 29 mg/mL, or about 30 mg/mL) In some exemplary embodiments, the concentration of the liposome is about 13 mg/mL. In some embodiments, the liposome is present in the composition in an amount of about 1 mg/mL to about 10 mg/mL, or about 5 mg/mL to about 15 mg/mL, or about 10 mg/mL to about 20 mg/mL, or about 15 mg/mL to about 30 mg/mL.

In some embodiments, the composition comprises a liposome described herein wherein the concentration of the nonglycosidic ceramide in the liposome is about 0.05 mg/mL to about 1 mg/mL (e.g., about 0.1 mg/mL to about 0.9 mg/mL, or about 0.2 mg/mL to about 0.8 mg/mL). In some embodiments, the concentration of the nonglycosidic ceramide in the liposome is about 0.05 mg/mL, about 0.10 mg/mL, about 0.15 mg/mL, about 0.20 mg/mL, about 0.25 mg/mL, about 0.30 mg/mL, about 0.35 mg/mL, about 0.40 mg/mL, about 0.45 mg/mL, about 0.50 mg/mL, about 0.55 mg/mL, about 0.60 mg/mL, about 0.65 mg/mL, about 0.70 mg/mL, about 0.75 mg/mL, about 0.80 mg/mL about 0.85 mg/mL, about 0.90 mg/mL, about 0.95 mg/mL, or about 1 mg/mL In some embodiments, the composition comprising a liposome described herein further comprises an antigen (e.g., a viral antigen, a bacterial antigen, a tumor antigen, and mixtures thereof) present in an admixture with the liposome. The antigen can be a tumor antigen, as previously described herein. In some embodiments, the antigen is selected from the group consisting of P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments thereof, and mixtures thereof, as previously described herein. In some exemplary embodiments, the antigen is NY-ESO-1, which can be present in a concentration of about 0.01 mg/mL to about 5 mg/mL, or about 0.1 to about 1 mg/mL, for example about 0.3 mg/mL to about 0.6 mg/mL (e.g., about 0.01 mg/mL to about 1 mg/mL, or about 1 mg/mL to about 3 mg/mL, or about 0.1 mg/mL to about 2 mg/mL, or about 2 mg/mL to about 5 mg/mL. For example, NY-ESO-1 can be present in the composition in an admixture with the liposome in an amount of about 0.01 mg/mL, about 0.05 mg/mL, about 0.1 mg/mL, about 0.15 mg/mL, about 0.2 mg/mL, about 0.25 mg/mL, about 0.3 mg/mL, about 0.35 mg/mL, about 0.4 mg/mL about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL about 0.95 mg/mL, about 1 mg/mL, about 1.5 mg/mL about 2 mg/mL, about 2.5 mg/mL about 3 mg/mL, about 3.5 mg/mL, about 4 mg/mL, about 4.5 mg/mL, or about 5 mg/mL.

In some embodiments, the composition comprising the liposome described herein further comprises a therapeutic agent present in an admixture with the liposome or within the aqueous core of the liposome. In some embodiments, the therapeutic agent is selected from the group consisting of an immune modulator (e.g., an anti-CD40 antibody, an anti-CD40L antibody, an anti-CTLA4 blocking antibody, or soluble LAG-3 based immune modulators), a Toll-like receptor agonist (e.g., MPL, CpG, single-stranded RNA, nucleotides, nucleotide analogs like CL087, or loxoribine, polyinosine-polycytidylic acid (poly I:C), flagellin, resiquimod, imiquimod, and gardiquimod), a Nod ligand (e.g., muramyl dipeptide, murabutide, peptidoglycan), an antiviral agent (e.g., oseltamivir phosphate), an antifungal agent (e.g., amphotericin B), an antibiotic, an antiviral antibody (e.g., palivizumab), a cancer immune therapeutic (e.g., herceptin, alemtuzumab, gemtuzumab, rituximab, ibritumomab tiuxetan, and other monoclonal antibody based cancer treatments), a chemotherapy agent, a kinase inhibitor (e.g., imatinib and erlotinib), a cytotoxic agent (e.g., cyclophosphamide), an anti-asthmatic agent, an antihistamine agent, an anti-inflammatory agent, a vaccine adjuvant (e.g., virus-like particles), a second liposome, an artificial antigen presenting cell, a cytokine or chemokine blocking antibody (e.g., infliximab, adalimumab, basiliximab), and mixtures thereof.

In some embodiments, the composition comprising the liposome further comprises at least one adjuvant present in an admixture with the liposome.

The composition comprising the liposomes described herein can be formulated for a standard route of administration, including parenteral, such as intravenous, intraperitoneal, subcutaneous or intramuscular, intrathecal, transdermal, rectal, oral, nasal or by inhalation. Parenteral injection or extended infusion, e.g. over a period of 1, 2, 3, 4, 5, 6, 7, 8, 12 or 24 hours is possible.

Compositions described herein can be formulated for administration in a form selected from the group consisting of a tablet, a capsule, a powder, a suppository, a lozenge, a soft gelatin capsule, a transdermal patch, an aerosol (e.g., pressurized or non-pressurized powder), a dragée, a cream (e.g., an oil-in-water emulsion or a water-in-oil emulsion), a drop, a liquid suspension, an emulsion, and an ointment.

The dose of the liposomes that is administered will vary with the exact composition of the liposome. In general the liposomes are administered to result in a daily dosage of the nonglycosidic ceramide of about 0.5 µg to about 30 mg, or about 1 µg to about 20 mg per kg of animal body weight, e.g., about 0.5 µg, about 1 µg, about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 420 µg, about 430 µg, about 440 µg, about 450 µg, about 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, about 600 µg, about 610 µg, about 620 µg, about 630 µg, about 640 µg, about 650 µg, about 660 µg, about 670 µg, about 680 µg, about 690 µg, about 700 µg, about 710 µg, about 720 µg, about 730 µg, about 740 µg, about 750 µg, about 760 µg, about 770 µg, about 780 µg, about 790 µg, about 800 µg, about 810 µg, about 480 µg, about 830 µg, about 840 µg, about 850 µg, about 860 µg, about 870 µg, about 880 µg, about 890 µg, about 900 µg, about 910 µg, about 920 µg, about 930 µg, about 940 µg, about 590 µg, about 960 µg, about 970 µg, about 980 µg, about 990 µg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, or about 30 mg. In some embodiments, the liposomes are administered to result in a daily dosage of the nonglycosidic ceramide in an amount of about 1 µg to about 200 µg, or about 1 mg to about 10 mg, or about 700 µg to about 2 mg, or about 800 µg to about 28 mg, or about 10 µg to about 30 mg, about 10 µg to about 5 mg. In some embodiments, the liposomes are administered in divided doses 1 to 4 times daily or in a sustained release form.

In some embodiments, the composition described herein comprises a lipid-bilayer coated particle, as previously described herein, in place of, or in addition to, a liposome.

Therapeutic and Prophylactic Uses

In yet another aspect, described herein is a method of treating a viral or microbial infection, a parasitic infection, an autoimmune disease, an allergy, or asthma in a mammalian subject in need thereof comprising administering to the subject the liposome described herein or the composition described herein in an amount effective to treat said infection autoimmune disease, allergy, or asthma. In a preferred embodiment, the mammalian subject is a human subject. Practice of methods described herein in other mammalian subjects, especially mammals that are conventionally used as models for demonstrating therapeutic efficacy in humans (e.g., primate, porcine, canine, or rabbit animals), is also contemplated. Routes of administration are described in the preceding section. Repeated administration is contemplated to maintain a sustained response for long term management of the disease or condition, or until a cure is achieved. Standard dose-response studies are used to optimize dose and dosing schedule.

In some embodiments, the liposomes described herein or compositions described herein can be used to treat a disorder caused by a virus. Exemplary viruses include, but are not limited to, a hepatitis virus, a liver tropic virus, a skin tropic virus, a lung tropic virus, an immune tropic virus, and combinations thereof. For example, the liposomes described herein or composition described herein can be used to treat disorders associated with a virus selected from the group consisting of hepatitis B virus (HBV), hepatitis C virus (HBC), human papilloma virus (HPV), herpes simplex virus (HSV), influenza virus, respiratory syncytial virus (RSV), human immunodeficiency virus (HIV), Epstein-Barr virus (EBV), cytomegalovirus (CMV), and combinations thereof.

In some embodiments, the liposomes described herein or compositions described herein are used to treat a microbial infection, such as a bacterial infection of the lung with e.g., *Haeemophilius influenza* or mycobacteria, e.g., *Mycobacterium tuberculosis*, a bacterial infection of the gut with e.g., *Helicobacter pylori*, a bacterial infection of the skin with e.g., *Staphylococcus aureus*, and combinations thereof.

In some embodiments, the liposomes described herein or compositions described herein can be used to treat an autoimmune disease. Autoimmune disorders which may be treated using a liposome disclosed herein include, but are not limited to, psoriasis, Crohn's disease, connective tissue disease, multiple sclerosis, systemic lupus erythematosus, rheumatoid arthritis, autoimmune pulmonary inflammation, Guillain Barre syndrome, autoimmune thyroiditis, insulin dependent diabetes mellitis, myasthenia gravis, graft versus host disease and autoimmune inflammatory eye disease.

In one aspect, the liposomes described herein or compositions described herein are used to treat cancer. In such embodiments, the liposome described herein or composition described herein is administered in a mammalian subject in need thereof, in amount effective to treat cancer. The term "cancer" generally refers to tumors, including both primary and metastasized tumors. In some embodiments, the tumor is a solid tumor.

The disclosed methods are useful for, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "cancer resistance" refers to an improved capacity of a subject to resist cancer growth, in particular growth of a cancer already had. In other words, the term "cancer resistance" refers to a decreased propensity for cancer growth in a subject.

In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Hiirthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand minor-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plamsa cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestimal cancers that may be targeted include extrahepatic bile duct cancer, colon cancer, colon and rectum cancer, colorectal cancer, gallbladder cancer, gastric (stomach) cancer, gastrointestinal carcinoid tumor, gastronintestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer à deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenstrom's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

In some embodiments, the liposomes described herein can be used to treat an allergic or asthmatic condition. Exemplary allergic or asthmatic conditions include, but are not limited to, anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems.

In another aspect, described herein is a method of stimulating an immune response in a mammalian subject comprising administering to the subject a liposome or composition described herein. In some embodiments, the liposome (or composition comprising the liposome) is administered directly to the subject in the same manner as a vaccine. In some embodiments, the liposomes described herein are useful for the induction of an immune response to a tumor antigen, one or more pathogenic organisms, or other antigen as described herein. The liposomes can be administered alone or in combination with therapeutic agent or prophylactic treatment. It is contemplated that administration of the liposome in combination with a therapeutic agent or prophylactic treatment will enhance the therapeutic or protective effect. In certain embodiments the vaccine will be a booster or at least the second exposure of a subject to such a vaccine and can comprise the same or different antigenic determinant relative to an initial administration.

In another variation of the invention, any of the methods described herein with respect to a liposome can be modified such that a lipid bilayer-coated particle is used in place of, or in addition to, a liposome.

Combination Therapy

In some embodiments, a standard of care treatment is administered with a liposome or lipid bilayer-coated particle described herein. In the context of methods of described herein, "standard of care treatment" refers to a treatment that is generally accepted by clinicians for a certain type of patient diagnosed with a type of illness. For all varieties of cancers and neoplastic disorders described herein, for example, an aspect of the disclosure is to improve standard of care therapy with co-therapy with the liposomes or lipid bilayer-coated particles described herein.

In some embodiments, the standard of care treatment is selected from the group consisting of a cytokine, a chemotherapeutic agent, a radiotherapeutic agent, and radiation therapy.

Cytokines that are effective in inhibiting tumor growth/metastasis are contemplated for use in the combination therapy. Such cytokines, lymphokines, or other hematopoietic factors include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin.

Any chemotherapeutic or radiotherapeutic agent may be suitable for use in combination with a liposome or lipid bilayer-coated particle described herein. Examples of suitable chemotherapeutic and radiotherapeutic agents include, but are not limited to: an anti-metabolite; a DNA-damaging agent; a cytokine useful as a chemotherapeutic agent; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radiosensitizer; a photosensitizer; a radiation source, optionally together with a radiosensitizer or photosensitizer; or other commonly used therapeutic agents.

In some embodiments, the therapeutic agent is a chemotherapeutic agent. Exemplary chemotherapeutic agents useful in methods described herein are listed in Table 1 below.

TABLE 1

| Alkylating agents |
| --- |
| Nitrogen mustards | mechlorethamine
cyclophosphamide
ifosfamide
melphalan
chlorambucil

| Nitrosoureas |
| --- | carmustine (BCNU)
lomustine (CCNU)
semustine (methyl-CCNU)

| Ethylenimine/Methyl-melamine |
| --- | thriethylenemelamine (TEM)
triethylene thiophosphoramide (thiotepa)
hexamethylmelamine (HMM, altretamine)

| Alkyl sulfonates |
| --- | busulfan

TABLE 1-continued

| Triazines |
| --- | dacarbazine (DTIC)

| Antimetabolites |
| --- |

Folic Acid analogs
methotrexate
Trimetrexate
Pemetrexed
Multi-targeted antifolate
Pyrimidine analogs
5-fluorouracil
fluorodeoxyuridine
gemcitabine
cytosine arabinoside
(AraC, cytarabine)
5-azacytidine
2,2'-difluorodeoxy-cytidine
Purine analogs
6-mercaptopurine
6-thioguanine
azathioprine
2'-deoxycoformycin
(pentostatin)
erythrohydroxynonyl-adenine
(EHNA)
fludarabine phosphate
2-chlorodeoxyadenosine
(cladribine, 2-CdA)

| Type I Topoisomerase Inhibitors |
| --- | camptothecin
topotecan
irinotecan
Natural products

| Antimitotic drugs |
| --- | paclitaxel
Vinca alkaloids
vinblastine (VLB)
vincristine
vinorelbine
Taxotere ® (docetaxel)
estramustine
estramustine phosphate

| Epipodophylotoxins |
| --- | etoposide
teniposide

| Antibiotics |
| --- | actimomycin D
daunomycin (rubido-mycin)
doxorubicin (adria-mycin)
mitoxantroneidarubicin
bleomycinsplicamycin
(mithramycin)
mitomycinC
dactinomycin

| Enzymes |
| --- |

L-asparaginase

| Biological response modifiers |
| --- | interferon-alpha
IL-2
G-CSF
GM-CSF

| Differentiation Agents |
| --- | retinoic acid derivatives

| Radiosensitizers |
| --- | metronidazole
misonidazole
desmethylmisonidazole
pimonidazole
etanidazole
nimorazole
RSU 1069

TABLE 1-continued

EO9
RB 6145
SR4233
nicotinamide
5-bromodeozyuridine
5-iododeoxyuridine
bromodeoxycytidine
Miscellaneous agents
Platinium coordination complexes cisplatin
Carboplatin
oxaliplatin
Anthracenedione mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon (*, *, *)
interleukin-2
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines In some embodiments, the combination therapy comprising administration of (a) a liposome or lipid bilayer-coated particle described herein and a therapeutic agent selected from the group consisting of an immune modulator (e.g., an anti-CD40 antibody, an anti-CD40L antibody, an anti-CTLA4 blocking antibody, or soluble LAG-3 based immune modulators), a Toll-like receptor agonist (e.g., MPL, CpG, single-stranded RNA, nucleotides, nucleotide analogs like CL087, or loxoribine, polyinosine-polycytidylic acid (poly I:C), flagellin, resiquimod, imiquimod, and gardiquimod), a Nod ligand (e.g., muramyl dipeptide, murabutide, peptidoglycan), an anti-viral agent (e.g., oseltamivir phosphate), an antifungal agent (e.g., amphotericin B), an antibiotic, an antiviral antibody (e.g., palivizumab), a cancer immune therapeutic (e.g., herceptin, alemtuzumab, gemtuzumab, rituximab, ibritumomab tiuxetan, and other monoclonal antibody based cancer treatments), a chemotherapy agent, a kinase inhibitor (e.g., imatinib and erlotinib), a cytotoxic agent (e.g., cyclophosphamide), an anti-asthmatic agent, an antihistamine agent, an anti-inflammatory agent, a vaccine adjuvant (e.g., virus-like particles), a second liposome or lipid bilayer-coated particle, an artificial antigen presenting cell, a cytokine or chemokine blocking antibody (e.g., infliximab, adalimumab, basiliximab), and mixtures thereof.

Treatment with the liposomes or lipid bilayer-coated particles described herein may precede or follow the administration of the standard of care treatment or therapeutic agent by intervals ranging from minutes to weeks. In embodiments where the standard of care treatment (or therapeutic agent) and a liposome or lipid bilayer-coated particle described herein are administered separately, one would generally ensure that a significant period of time did not expire between the times of each delivery, such that the standard of care treatment (or therapeutic agent) and the liposome or lipid bilayer-coated particle would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated.

The invention is further described in the following Examples. The Examples serve only to illustrate the invention and are not intended to limit the scope of the invention in any way.

EXAMPLES

Example 1—Manufacture of Liposomes

This example describes a general procedure for the manufacture of liposomes containing two lipids and a nonglycosidic ceramide.

The liposomes described herein were manufactured using the Solvent Dilution method. In this method, the lipids are dissolved in an appropriate solvent, which is then slowly diluted in an aqueous buffer to form multilamellar vesicles (MLV's). In some embodiments, an antigen is added to the aqueous buffer when antigen-encapuslated lipsomes are desired. The resulting material is passed through an extruder with a specific pore size to generate large unilamellar vesicles (LUV's). The LUV suspension is diafiltered against buffer to remove solvent, and if desired, to concentrate the liposomes to the final concentration. Finally, the material is filtered through one or more sterilizing grade filters before being filled into vials.

Specifically, a stock solution (5 mg/mL) of the nonglycosidic ceramide was prepared by dissolving 25 mg of the nonglycosidic ceramide in 5.0 mL t-butanol/water (95/5, v/v), with heating at 60° C. Appropriate lipids were weighed and an aliquot of the nonglycosidic ceramide stock solution was added to the lipids to obtain the desired nonglycosidic ceramide to lipid ratio. The volume of mixture was then adjusted with t-butanol:water (95:5, v:v) to a total volume of 1.0 mL, and the mixture heated at 60° C. to dissolve the lipids. An aliquot of Rh-PE (5 mg/mL in ethanol) was added (at 0.25 mol %) to the dissolved lipid/nonglycosidic ceramide solution. The resulting solution was diluted into 9 mL of 145 mM NaCl-10 mM phosphate buffer pH 6.5 (PBS), pre-heated to 60° C. to produce multi-lamellar vesicles (MLVs) at 5.0 mg/mL total lipid, 10% solvent. The MLVs were then extruded at 60° C. through two stacked 80 nm polycarbonate filters, using a 10 mL LIPEX™ extruder (Northern Lipids), to produce large unilamellar vesicles (LUVs), with a target vesicle size of 100 nm or less. Using a SPECTRUM™ cartridge (55 cm$^2$, 500,000 molecular weight cut-off (MWCO)), the sample was concentrated to approximately 5 mL, then diafiltered against 10 volumes phosphate buffered saline (PBS) to remove the solvent. The sample was then sterile filtered by passing it through a 0.2 µm SARTORIUS™ MINISART® syringe filter and aliquots transferred to clean depyrogenated vials, which were then stoppered and capped. Because the lipids were sterile filtered, they are acceptable for clinical use. Samples were stored at 2-8° C. This process can also be practiced under industrial conditions using the GMP process.

Example 2—Method of Manufacturing Liposomes with Different Components

This example describes a procedure for the manufacture of liposomes containing egg phosphatidylcholine, egg phosphatidylglycerol, and theritol ceramide (EPC:EPG:TC).

A stock solution (5 mg/mL) of threitolceramide was prepared by dissolving 25 mg in 5.0 mL t-butanol/water (95/5, v/v), with heating at 60° C. Appropriate lipids (see Table 2) were weighed and an aliquot of the threitolceramide stock solution was added to the lipids to obtain the desired threitolceramide to lipid ratio. The volume of the mixture was then adjusted with t-butanol:water (95:5, v:v) to a total volume of 1.0 mL, and the mixture heated at 60° C. to dissolve the lipids. An aliquot of Rh-PE (5 mg/mL in ethanol) was added (at 0.25 mol %) to the dissolved lipid/threitolceramide solution. The resulting solution was diluted into 9 mL of 145 mM NaCl-10 mM phosphate buffer pH 6.5 (PBS), pre-heated to 60° C. to produce multi-lamellar vesicles (MLVs) at 5.0 mg/mL total lipid, 10% solvent. The MLVs were then extruded at 60° C. through two stacked 80 nm polycarbonate filters, using a 10 mL LIPEX™ extruder (Northern Lipids), to produce large unilamellar vesicles (LUVs), with a target vesicle size of 100 nm or less. Using a SPECTRUM™ cartridge (55 cm$^2$, 500,000 molecular weight cut-off (MWCO)), the sample was concentrated to approximately 5 mL, then diafiltered against 10 volumes phosphate buffered saline (PBS) to remove the solvent. The sample was then sterile filtered by passing it through a 0.2 µm SARTORIUS™ MINISART® syringe filter and aliquots transferred to clean depyrogenated vials, which were then stoppered and capped. Samples were stored at 2-8° C. The lipid compositions described herein in Table 2 were supplied by Northern Lipid Inc.

TABLE 2

Liposome Compositions (total volume of 5 mL)

| Name | Vesicle Size | wt/wt/wt | TC Content (mg/mL) |
|---|---|---|---|
| EPC/EPG | 41.8 ± 13.3 | 25/75 | 0 |
| EPC/EPG/TC (2) | 44.8 ± 14.2 | 24.5/73.5/2 | 0.134 |
| EPC/EPG/TC (5) | 47.7 ± 16.2 | 23.8/71.3/5 | 0.385 |
| EPC/EPG/TC (10) | 69.0 ± 24.5 | 22.5/67.5/10 | 0.794 |
| EPC/CHOL/TC (2) | 93.1 ± 43.7 | 54/36/10 | 0.663 |
| EPC/DDAB/TC (2) | 69.7 ± 23.4 | 54/36/10 | 0.683 |

EPC = egg phosphatidylcholine;
EPG = egg phosphatidylglycerol;
CHOL = cholesterol;
DDAB = dimethyldioctadecyl ammonium bromide;
TC = threitolceramide

Example 3—Non-Glycosidic Ceramide-Containing Liposomes Activate Natural Killer T Cells in Vitro This Example illustrates ability of the threitolceramide-containing liposomes to activate murine invariant natural killer cells (iNKT) and human cells, as measured by IFNγ release.

Splenocytes were prepared from either wild type (WT) or CD1d$^{-/-}$ (NKT cell deficient) mice and cultured in the presence of titrating amounts (10 µg/ml, 1 µg/ml, 100 ng/ml) of non-glycosidic ceramide containing liposomes (EPC:DDAB:TC(10); EPC:EPG:TC(2); EPC:EPG:TC(5); EPC:EPG:TC(10) and EPC:CHOL:TC(10)), control liposome (EPC:EPG), soluble threitolceramide or soluble α-GalCer for 72 hours. Soluble threitolceramide and soluble α-GalCer were prepared by dissolution in a chloroform/methanol/water solution (10:10:3) at 10 mg/mL. The resulting solution was diluted to a final volume of about 200 µg/mL using vehicle solution comprised of NaCl (about 150 mM) and polyoxyethylene (20) sorbitan monolaurate (i.e., Tween 20, 0.5%). Supernatants were removed from cultures and the amount of IFNγ produced by the cells was quantified by ELISA. Briefly, ELISA plates were coated with 1D1K antibody (Mabtech) and left overnight at 4° C. The plates were washed with 0.05% Tween 20 in PBS (v/v). To eliminate any non-specific antigen binding, the plates were coated (i.e. blocked) with 200 µL of 10% FCS in PBS (v/v) and incubated for 2 h at 37° C. 100 µL of reaction supernatant was transferred to the ELISA plate and the standard was added starting at 50 ng ml$^{-1}$. The plate was then incubated at 4° C. overnight. The following day, the plates were washed with 0.05% Tween 20 in PBS and the biotinylated anti-cytokine detecting mAb was added at 50 µL/well and incubated at room temperature for 2 h. After incubation, the plates were washed eight times with 0.05% Tween 20 in PBS. 100 µL of working dilution of avidin-peroxidase was added per well after which the plates were incubated at room temperature for 2 h. The plates were once again washed eight times with 0.05% Tween 20 in PBS. 100 µl of tetramethylbenzidine (TMB) agent was added per well. Reaction was stopped with 50 solution of 0.5 M H$_2$SO$_4$ and the optical density of each well was measured immediately using a microplate reader (Bio-Rad, model 680) set to 450 nm.

The results are provided below in Table 3.

| Assayed material | IFNγ (ng/ml) |
|---|---|
| EPC:EPG (Control) | 0.31 |
| EPC:EPG:TC (2) | 3.89 |
| EPC:EPG:TC (5) | 5.61 |
| EPC:EPGTC (10) | 7.35 |
| EPC:Chol:TC (10) | 0.45 |
| EPC:DDAB:TC (10) | 3.56 |
| DOPC:Chol:TC | 0.37 |
| Soluble TC | 3.77 |
| Soluble α-GalCer | 9.21 |

Figure 1B:
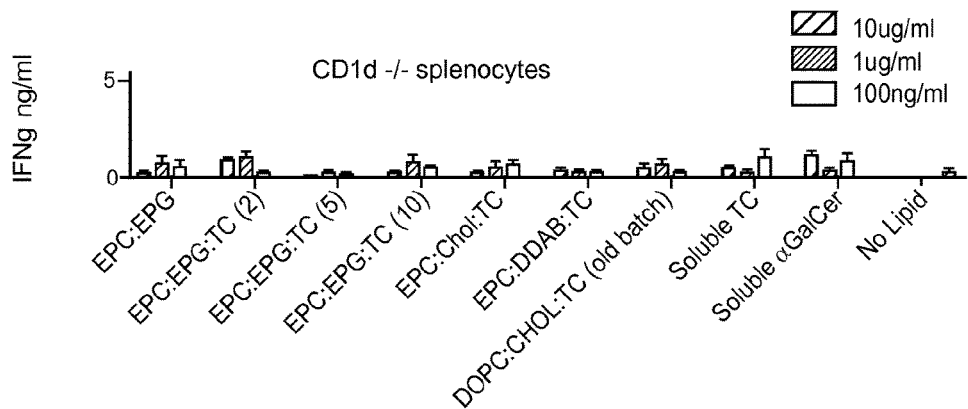
FIG. 1 B shows that the non-glycosidic ceramide containing liposomes caused minimal activation in vitro using splenocyteS prepared from CD1d$^{-/-}$ (NKT-deficient (mice (negative control).

Results indicated that the EPC:EPG and EPC:DDAB:TC liposomes were both able to activate iNKT cells to the same extent as soluble threitolceramide (FIG. 1A). iNKT cell activation was not observed with the EPC:EPG control liposome (FIG. 1B). Likewise, IFNγ in the CD1d$^{-/-}$ splenocyte culture was also not observed with the EPC:EPG control liposome. The EPC:DDAB:TC formulations appeared to aggregate on the cultured cells.

Example 4—Non-Glycosidic Ceramide Containing Liposomes Induced Natural Killer T Cell Activation In Vivo This example illustrates the in vivo effect of threitolceramide-containing liposomes on dendritic cell (DC) maturation, as measured by CD86 and CD40 expression, and iNKT cell activation, as measured by IL-4 and IFNγ release.

WT (n=3) and CD1d$^{-/-}$ (n=1) mice were administered 1 μg of liposomes (EPC:DDAB:TC(10); EPC:EPG:TC(2); EPC:EPG:TC(5); EPC:EPG:TC(10) and EPC:CHOL:TC (10)) or control liposome (EPC:EPG), soluble threitolceramide or soluble α-GalCer by intravenous injection.

DC Maturation:

18 hours post-injection, the spleens of the mice were harvested and the phenotype of DC maturation was examined by flow cytometry as determined by the median fluorescent intensity (MFI) of CD86 and CD40 expression.

Activation of NKT Cells:

Serums were obtained by tail venipuncture 2 and 18 hours post-injection to detect IL-4 and IFN-γ levels by ELISA.

The results are provided below in Table 4.

| Assayed Material | CD86 (DC maturation) Median | CD40 (DC maturation) Median | INFγ (serum) ng/ml | IL-4 (serum) ng/ml |
|---|---|---|---|---|
| EPC:EPG (Control) | 7.9 | 16.8 | 0 | 0 |
| EPC:EPG:TC (2) | 46.8 | 26.9 | 0.27 | 0.63 |
| EPC:EPG:TC (5) | 61.2 | 32.8 | 1.93 | 0.81 |
| EPC:EPGTC (10) | 58.7 | 31.3 | 1.09 | 0.71 |
| EPC:Chol:TC (10) | 68.4 | 39.1 | 3.32 | 0.53 |
| EPC:DDAB:TC (10) | 36.6 | 34.6 | 13.1 | 0.90 |
| DOPC:Chol:TC | 62.6 | 32.9 | 2.07 | 0.62 |
| Soluble TC | 60.1 | 28.9 | 0.99 | 0.12 |
| Soluble α-GalCer | 91.6 | 39.1 | 8.47 | 0.83 |

Results indicated that all threitolceramide-containing liposomes were able to induce DC maturation to the same extent as soluble threitolceramide but the EPC:DDAB:TC liposome also induced DC maturation in CD1d−/− mice (FIG. 2).

Figure 3A:
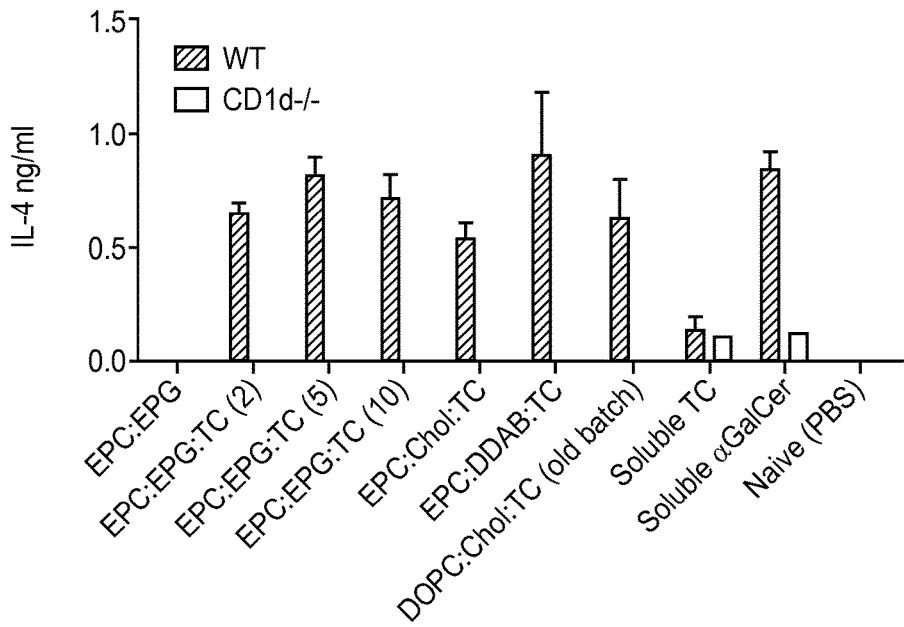
FIGS. 3A and 3B shows serum IL-4 and IFN-γ, respectively, levels 2 hours after injection of either wild-type mice or CD1d$^{-/-}$ (NKT-deficient) mice with liposomes.
Figure 3B:
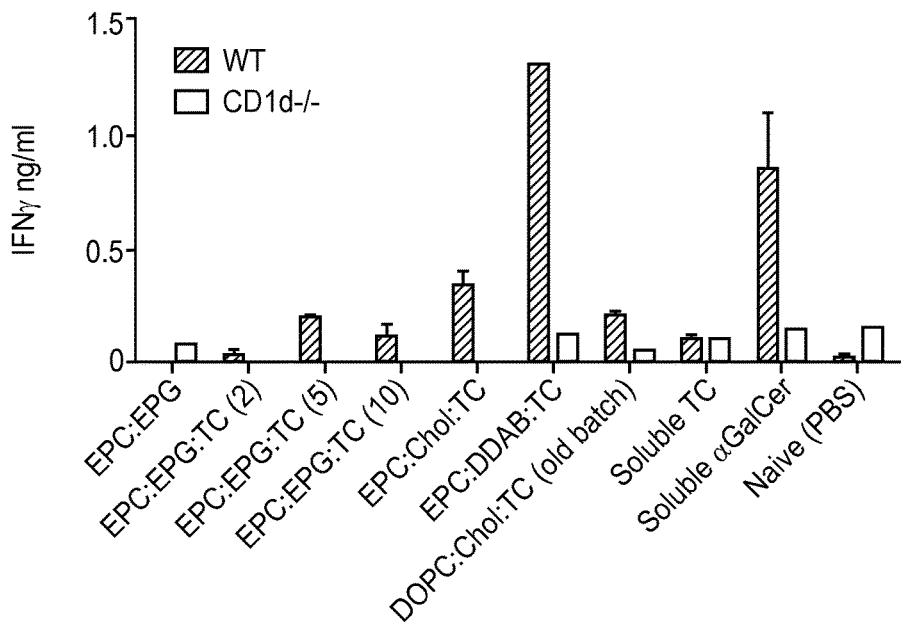

The production of iNKT-cell associated cytokines following activation was either comparable to or greater than soluble threitolceramide at 2 hours (IL-4; FIG. 3A) and 18 hours (IFNγ; FIG. 3B) using the liposomes.

Example 5—Non-Glycosidic Ceramide-Containing Liposomes Induce Dendritic Cell Maturation In Vitro Peripheral blood mononuclear cells (PBMCs) were isolated from healthy mice buffy coats by density gradient centrifugation over Lymphoprep (Nycomed). Monocytes were positively selected using anti-CD14 mAb-coated magnetic beads (MACS; Miltenyi Biotec) and were then cultured in 6-well plates in either X-Vivo 15+2% Human AB serum with 800 U ml$^{-1}$ granulocyte monocyte colony stimulating factor (GM-CSF) and 500 U ml$^{-1}$ IL-4 for 4 days to produce immature DCs. On day 4, liposomes identified in Table 2 (at concentration of 1 μg ml$^{-1}$ or 100 ng ml$^{-1}$), soluble threitolceramide ml$^{-1}$) or soluble α-GalCer (100 ng ml$^{-1}$) were added to the immature DCs, followed by the addition of maturation cocktail (IL-1β, IL-6, TNF-α, and PGE2) after 3 hours. DCs were harvested and assayed with iNKT cells overnight, the supernatants were taken and an IFNγ ELISA, the results of which are set forth in FIG. 6. Briefly, ELISA plates were coated with 1D1K antibody (Mabtech) and left overnight at 4° C. The plates were washed with 0.05% Tween 20 in PBS (v/v). To eliminate any non-specific antigen binding, the plates were coated (i.e. blocked) with 200 μL of 10% FCS in PBS (v/v) and incubated for 2 h at 37° C. 100 μL of reaction supernatant was transferred to the ELISA plate and the standard was added starting at 50 ng ml$^{-1}$. The plate was then incubated at 4° C. overnight. The following day, the plates were washed with 0.05% Tween 20 in PBS and the biotinylated anti-cytokine detecting mAb was added at 50 μL/well and incubated at room temperature for 2 h. After incubation, the plates were washed eight times with 0.05% Tween 20 in PBS. 100 μL of working dilution of avidin-peroxidase was added per well after which the plates were incubated at room temperature for 2 h. The plates were once again washed eight times with 0.05% Tween 20 in PBS. 100 μl of tetramethylbenzidine (TMB) agent was added per well. Reaction was stopped with 50 μl solution of 0.5 M H$_2$SO$_4$ and the optical density of each well was measured immediately using a microplate reader (Bio-Rad, model 680) set to 450 nm.

Figure 9:
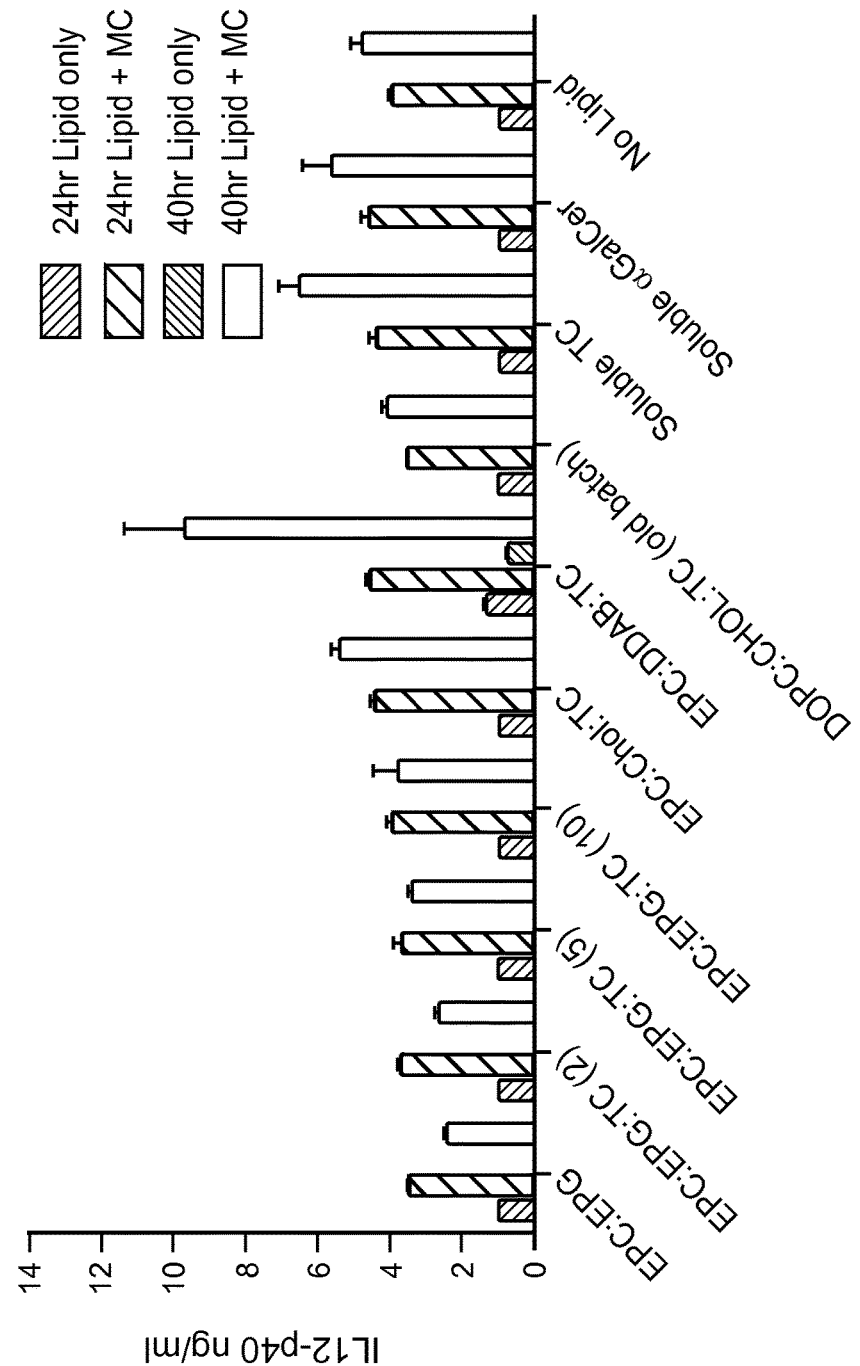
FIG. 9 is a graph showing the functionality of liposome-pulsed dendritic cells in the presence of maturation cocktail (TNFα, IL-1β, IL-6 and PGE2).

The presence of IL12-p40 was also detected by ELISA, the results of which are set forth in FIG. 9.

Figure 5:
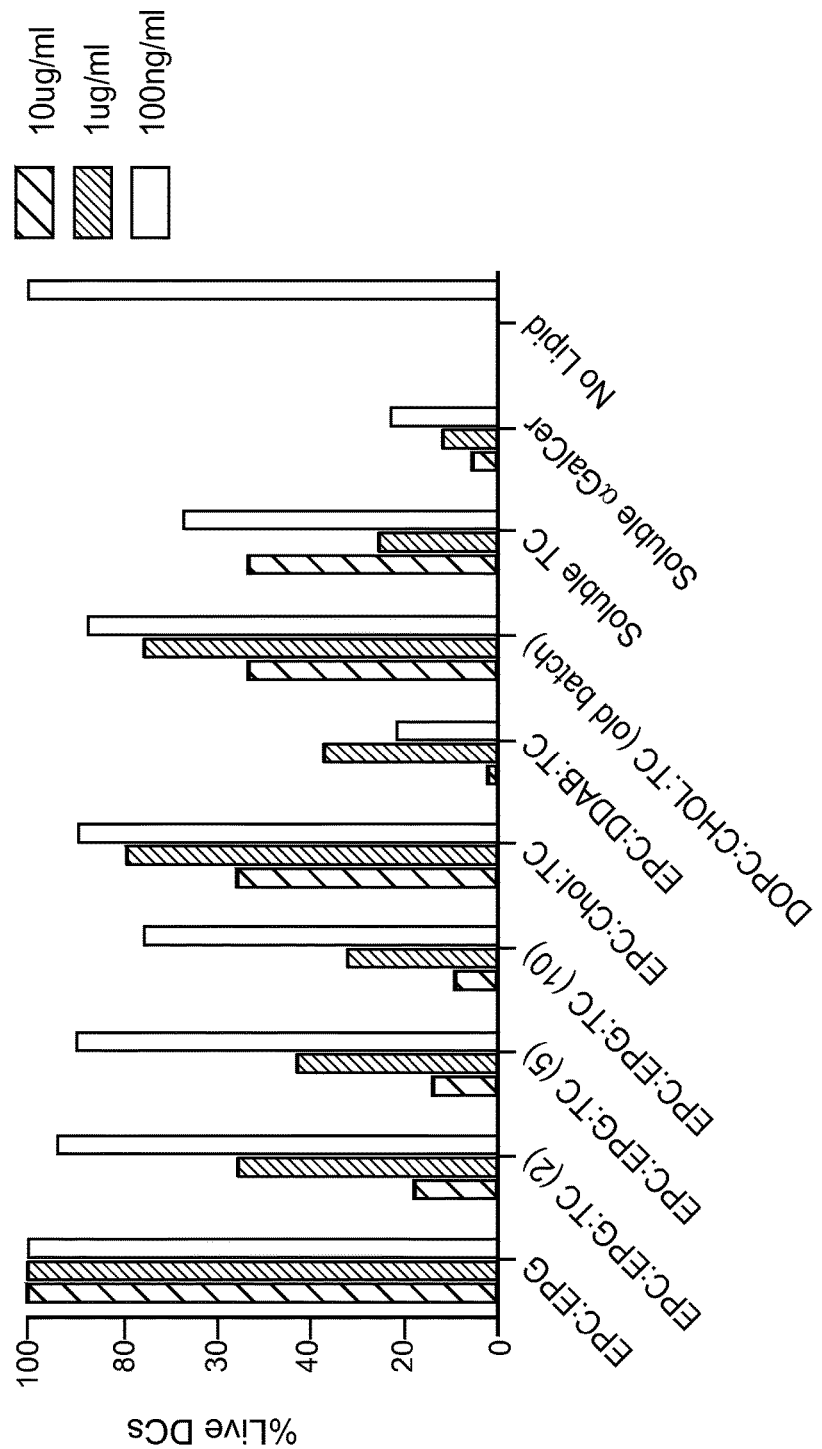
FIG. 5 is a graph showing the viability of lipid pulsed dendritic cells after iNKT interaction.
Figure 6:
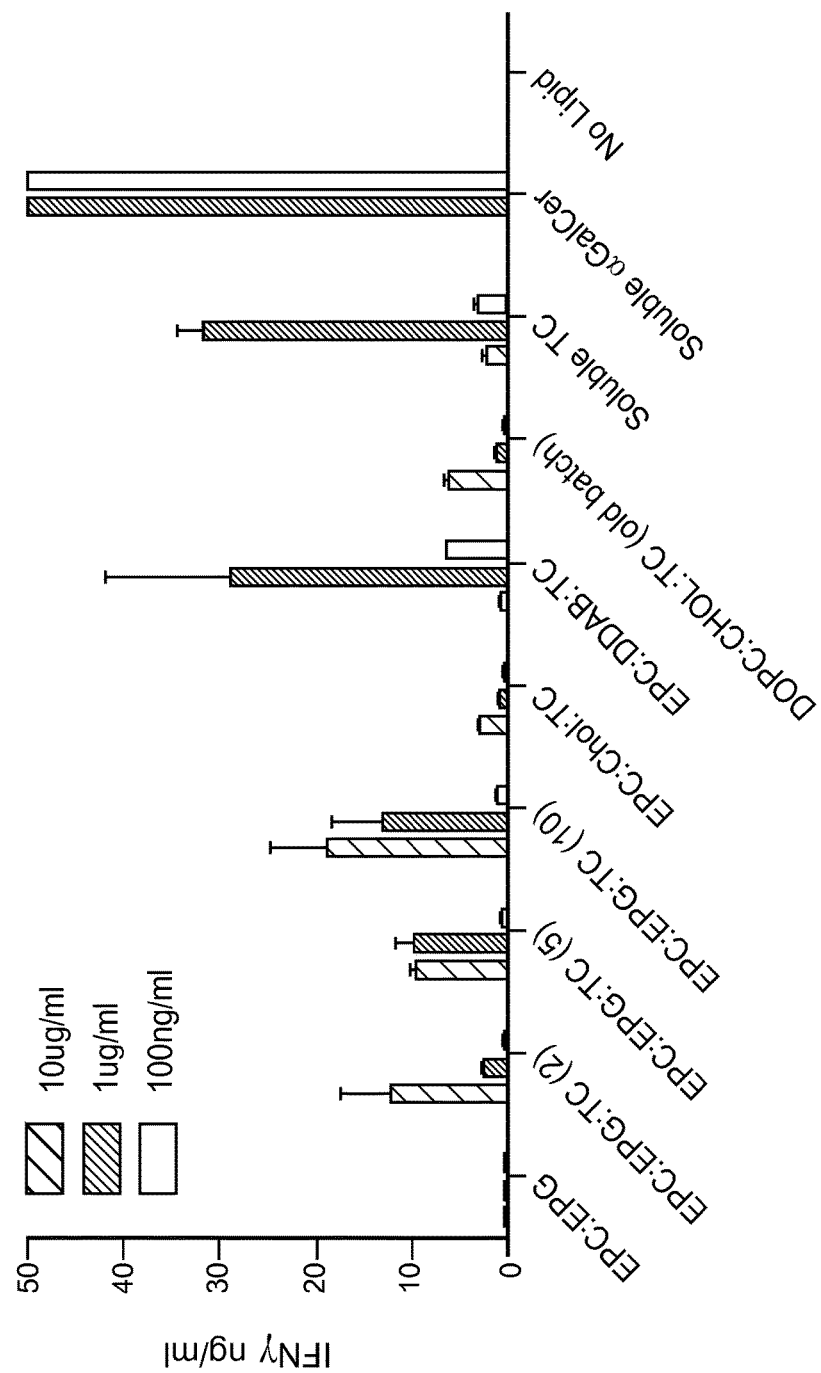
FIG. 6 shows the level of IFN-γ released by invariant natural killer (iNTK) cells that were assayed with dendritic cells pulsed 24 hours with different concentrations of liposomes.
Figure 7:
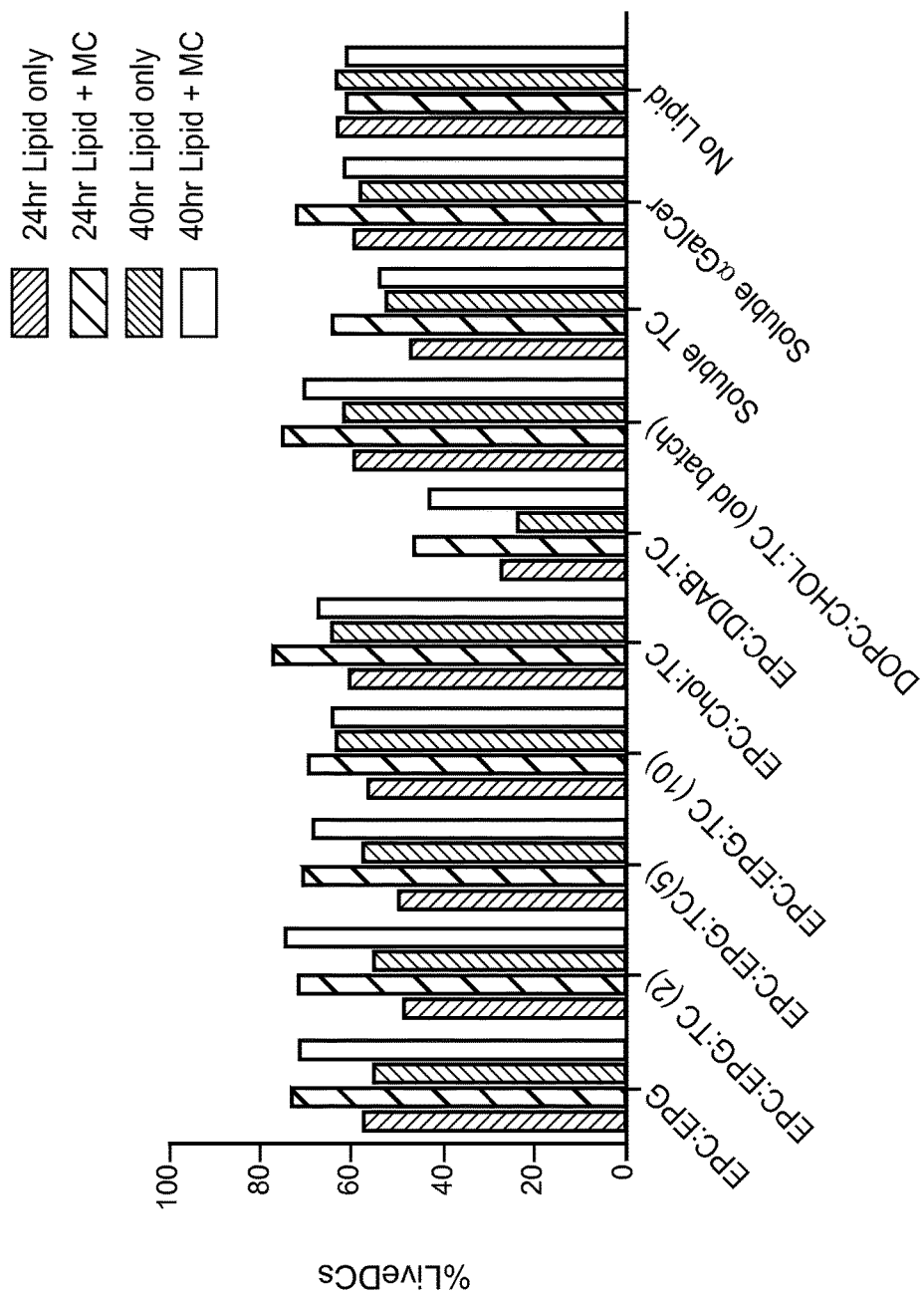
FIG. 7 is a graph showing the viability of liposome-pulsed dendritic cells with and without maturation cocktails for 24 or 48 hours.
Figure 8:
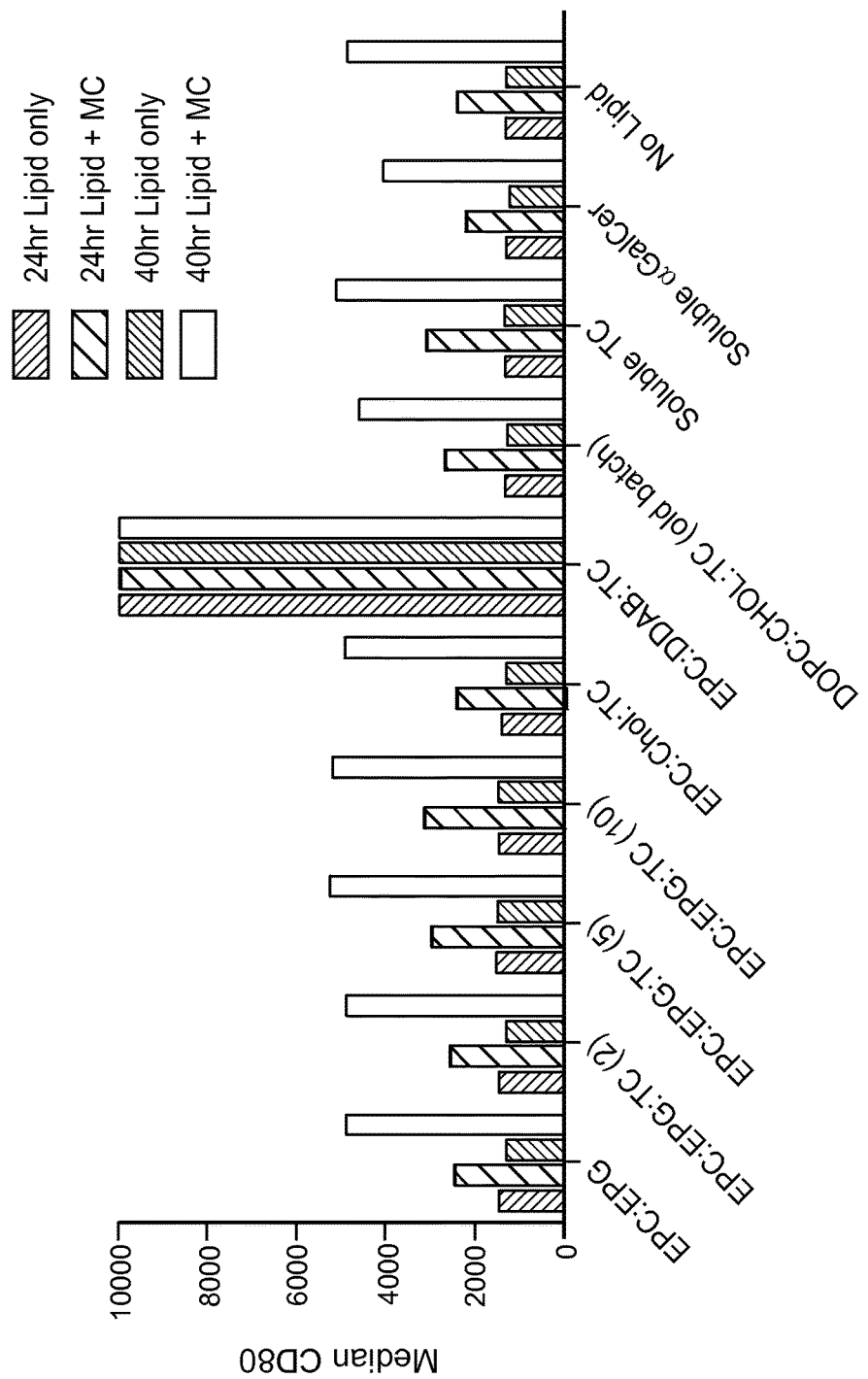
FIG. 8 is a graph showing that upregulation of CD80 on lipid-pulsed dendritic cells is increased in the presence of the maturation cocktail.

DCs were also analyzed by FACS after addition of liposomes for expression of the co-stimulatory molecule CD80 (FIG. 8) and for cell viability (FIGS. 5 and 7).

Figure 4:
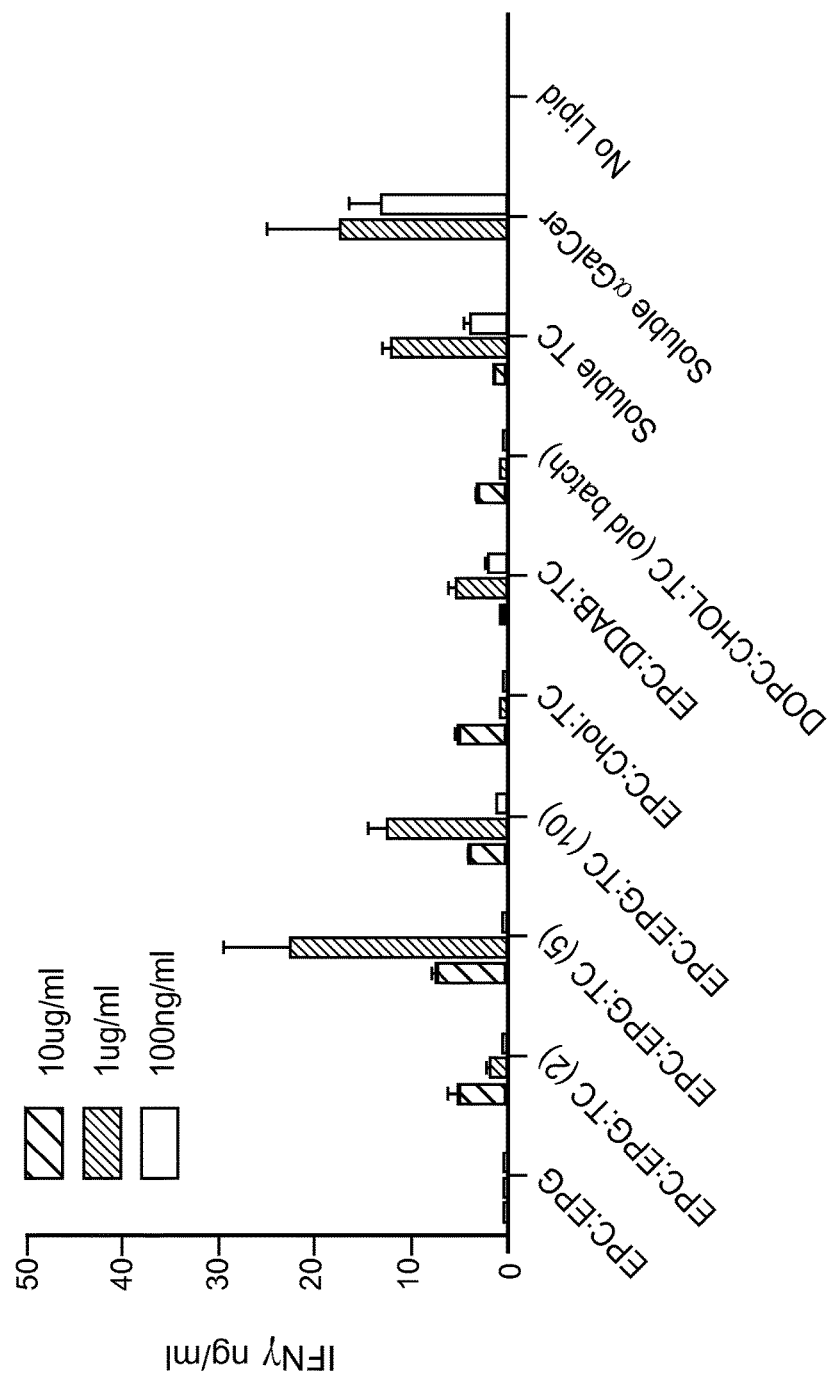
FIG. 4 shows the level of IFN-γ released by invariant natural killer (iNTK) cells that were assayed with dendritic cells pulsed for 40 hours with different concentrations of liposomes.

Results provided in FIG. 4 indicate that the EPC:EPG:TC formulation particularly at 10% threitolceramide was superior to all tested formulations (and easier to handle than EPC:DDAB:TC, data not shown).

Example 6—Human iNKT Cell TCR Binding Assay

This example illustrates the effect of the threitolceramide-containing liposomes on iNKT T-Cell Receptor (TCR) priming in vitro.

The efficiency of binding of liposomes to human CD1d molecule and recognition by the iNKT T-cell-receptor (TCR) was investigated in vitro. C1R human-CD1d expressing cells were cultured overnight with various dilutions of the liposomes identified above in Table 2, soluble α-GalCer or soluble threitolceramide (5 µg/mL to 1 ng/mL). The cells were washed and incubated with a fluorescently labelled iTCR tetramer. Binding of iTCR to lipid-CD1d complex was determined by flow cytometry.

The results are provided in FIG. 10. Results indicated that the EPC:EPG:TC formulation bound with the greatest efficiency, better than soluble threitolceramide. In contrast, the EPC:EPG:CHOL and EPC:EPG:DDAB liposomes bound weakly to the iTCR in comparison to the EPC:EP:TC formulation and soluble threitolceramide (FIG. 10).

Example 7—Adjuvant Properties of EPC:EPG Liposome Formulations

This Example illustrates the expansion of an endogenous T cell repertoire that recognizes the ovalbulmin (OVA) peptide, SIINFEKL (SEQ ID NO: 1), in an in vivo mouse using a threitolceramide-containing liposome.

Figure 11:
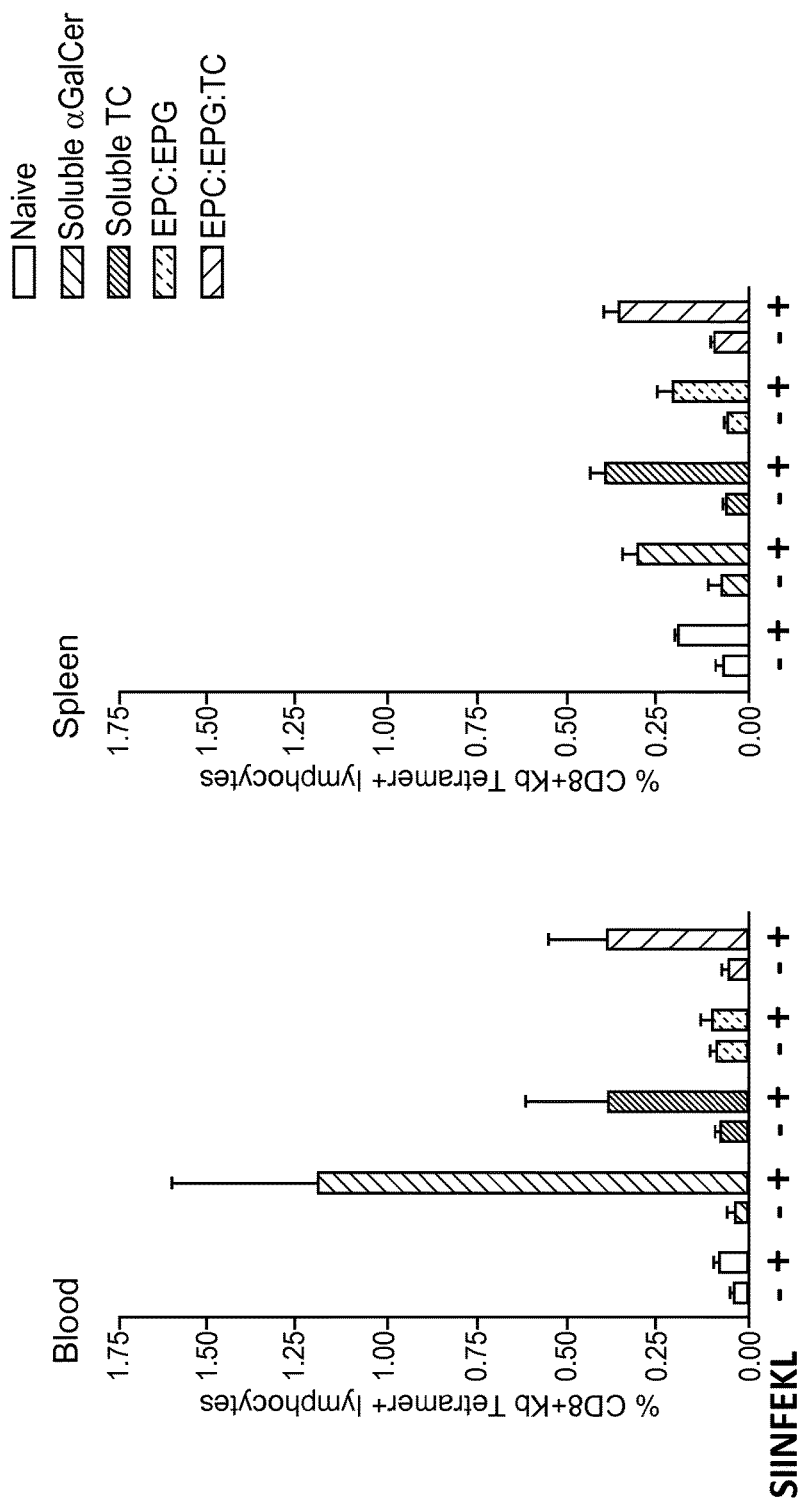
FIGS. 11 and 12 are graphs showing the adjuvant properties of EPC:EPG:TC formulation by showing the levels of CD8+Kb-tetramer+lymphocytes in the blood and spleen of tested mice.

Having established in Example 6 that the EPC:EPG:TC formulation was the most comparable to soluble TC, the ability of the EPC:EPG:TC (10%) liposome to expand an endogenous T cell repertoire that recognizes the ovalbulmin (OVA) peptide, SIINFEKL (SEQ ID NO:1), in an in vivo B6 mouse model was determined. A protocol similar to that which would be used clinically was developed. In this protocol, bone-marrow-derived-DC (BMDC) cultures containing GM-CSF and IL-4 were generated at day −6. At day −1, BMDC were left untreated or pulsed with either EPC:EPG (control liposome), EPC:EPG:TC (10%) or soluble threitolceramide, before being matured with LPS overnight. The following day, SIINFEKL peptide (SEQ ID NO: 1) was added to cultures for 3 hours, cells were then washed, and 1×10$^6$ BMDC injected intravenously. At day 7 post injection, mice were harvested and the percentage of CD8+Kb tetramer positive cells were determined by flow cytometry in the blood and spleen. Results indicated that the degree of CD8+Kb tetramer+ cells expansion using the liposome was directly comparable to that expanded by the soluble threitolceramide (FIG. 11).

Figure 12:
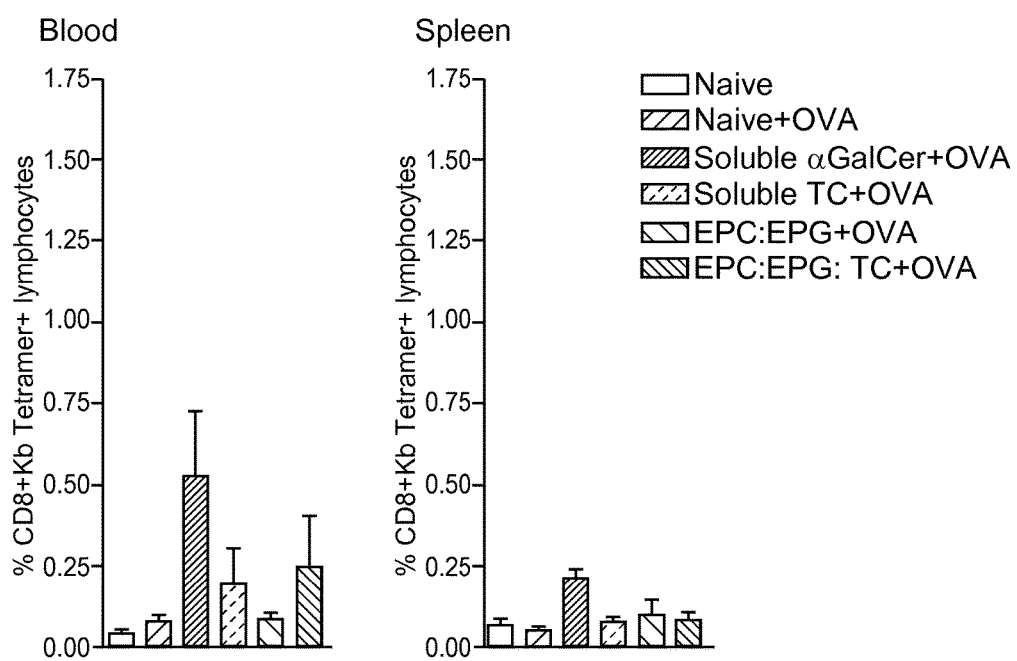

In another protocol, 800 µg of the OVA peptide and either soluble αGalCer, soluble TC, control liposome (EPC:EPG) or a EPC:EPG:TC liposome were injected into B6 mice intravenously. 7 days post injection, OVA-specific T cells were analyzed in the blood serum and the spleen. Results are provided in FIG. 12.

Example 8—Preparation of Antigen-Associated Liposomes

The following Example evaluates the effects of the association of NY-ESO-1 with the EPC/EPG/TC liposome as described in Example 1.

Briefly, ~1 mg/ml of NY-ESO-1 (in 4M urea, 50 mM glycine, 145 mM NaCl, 10 mM phosphate, pH 6.5) was diluted to 1 mg/ml by combining 3 mL of NY-ESO-1 solution with 0.18 mL 4M urea, 50 mM glycine, 145 mM NaCl, 10 mM phosphate, pH 6.5. The diluted NY-ESO1 solution was combined with the EPC/EPG/TC liposomes and the samples were diluted as needed (see Table 5 below) for determination of vesicle size. Vesicle size (dual angle) was determined using a Malvern Nanosizer. Upon dilution of the NY-ESO-1 into the liposome suspension, the NY-ESO-1 binds ionically to the negatively charged surface of the liposomes. This is evidenced by the very low level of association of NY-ESO—with neutral (EPC) liposomes (<6%) and the increased association with liposomes in direct correlation to the molar content of anionic lipid (EPG) in the liposomes. Hydrophobic interactions may also contribute to the interaction of NY-ESO-1 with the liposomes but ionic interactions are clearly dominant.

TABLE 5

| Sample X | NY-ESO-1 (mL) | PBS (mL) | Liposomes (mL) | Required dilution for size | Lipid:protein Mass Ratio | TC:NY-ESO-1 Mass Ratio |
|---|---|---|---|---|---|---|
| 1 | 0.5 | 0.5 | 0 | None | N/A | N/A |
| 2 | 0.5 | 0.384 | 0.116 | None | 1:1 | 0.1:1 |
| 3 | 0.5 | 0.355 | 0.145 | None | 2.5:1 | 0.25:1 |
| 4 | 0.5 | 0.209 | 0.291 | 2.5X | 5:1 | 0.5:1 |
| 5 | 0.5 | 0.064 | 0.436 | 3.75X | 7.5:1 | 0.75:1 |
| 6 | 0.43 | 0.07 (urea, gly, PBS) | 0.5 | 4X | 10:1 | 1:1 |
| 7 | 0 | 0.25 (urea, gly, PBS) | 0.25 | 4X | N/A | N/A |

Table 6 below provides the vesicle size of the liposomes within each sample when mixed with NY-ESO-1. An increase in vesicle size indicates interaction of the NY-ESO-1 antigen with the liposomes. Without wishing to be bound by theory, it is contemplated that this interaction involves frosslinking of the anionic liposomes by the multivalent (positive charges) of NY-ESO-1.

TABLE 6

| Sample | Z-Avg. | PDI | Peak 1 Diameter | Peak 1 Width | Peak 2 Diameter | Peak 2 Width | Peak 3 Diameter | Peak 3 Width |
|---|---|---|---|---|---|---|---|---|
| 1 | 72.86 | 0.402 | 67.19 (88.2%) | 30.05 | 315.3 (5.5%) | 82.85 | 5298 (4.5%) | 403.4 |
| 2 | 3217 | 0.339 | 3145 (100%) | 468.3 | | | | |
| 3 | 3867 | 0.427 | 1837 (100%) | 255.3 | | | | |
| 4 | 1593 | 0.073 | 1673 (100%) | 292.2 | | | | |
| 5 | 1038 | 0.218 | 1283 (100%) | 349.9 | | | | |
| 6 | 755.9 | 0.591 | 1291 (89.9%) | 468.1 | 104.2 (10.1%) | 15.26 | | |
| 7 | 62.29 | 0.102 | 69.77 (100%) | 24.3 | | | | |

Results indicated that there were no obvious physical changes (i.e., no precipitate, no increase in turbidity) when NY-ESO-1 or the liposomes were diluted with PBS. In contrast, when NY-ESO-1 was combined with the liposomes, there was a significant increase in turbidity in all samples, with no apparent difference between samples with varying amounts of lipid. However, after standing at room temperature for a period of time, sample 2 was distinctly flocculant, sample 3 showed some degree of flocculance, and samples 4-6 appeared turbid but homogenous. Large flocculates are difficult to inject and would be expected to have variable efficacy.

The samples were then centrifuged for 5 minutes at 1000×g. After centrifugation, no pellet was observed in samples 1 or 7 (NY-ESO-1 only, liposomes only, respectively). Samples 2 and 3 both had complete pelleting with clear supernatant. Sample 4 had a more loosely packed pellet with clear supernatant. Samples 5 and 6 had no distinct pellets, but appeared to be less homogenous.

Example 9—Activity of Antigen-Associated Liposomes

The liposomes described herein comprising full length NY-ESO-1 protein (prepared according to a method provided in Example 8) are intravenously injected into HHD mice crossed with C57BL6 mice (F1 mice). HLA A2 restricted responses specific for the NY-ESO-1 157-165 peptide are assessed by either HLA A2 tetramer staining or by an ELISPOT assay. Because NY-ESO-1 encodes a H-2 I-Ab epitope (Lopes L. *J. Virol* 82:86-95, 2007, incorporated herein by reference), the experiment is repeated using C57BL/6 mice and I-Ab restricted responses are assessed by ELISPOT assays. Control mice receive recombinant full length NY-ESO-1 protein alone, or with soluble threitolceramide. In another variation the experimental and control mice receive their respective regimen in combination with TLR ligands (e.g., CpG). Anti NY-ESO-1 specific antibody responses are measured by ELISA. The expansion of NY-ESO-1-specific immune responses is demonstrated.

Mice are challenged with H-2b tumor cells or transplanted tumors transduced with lentiviral vectors encoding the full length NY-ESO-1 protein, with or without transfected HLA-A2 cDNAs. Tumor growth or shrinkage and survival times are assessed.

(c) a phosphatidylglycerol (PG) lipid present in an amount of about 65 wt. % to about 75 wt. %, based upon the total weight of the liposome.

2. The liposome of claim 1, wherein the phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), egg phosphatidylcholine (EPC), and mixtures thereof; and wherein the phosphatidylglycerol is selected from the group consisting of 1,2-dierucoyl phosphatidylglycerol (DEPG), 1,2-dilauroyl phosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2-distearoyl phosphatidylglycerol (DSPG), 1-palmitoyl-2-oleoyl phosphatidylglycerol (POPG), egg phosphatidylglycerol (EPG), salts of any of the foregoing, and mixtures thereof.

---

---

What is claimed:

1. A liposome comprising:
   (a) threitolceramide present in an amount of about 3 wt. % to about 12 wt. %, based upon the total weight of the liposome;
   (b) a phosphatidylcholine (PC) lipid that is present in an amount of about 20 wt. % to about 30 wt. %, based upon the total weight of the liposome; and 3. The liposome of claim 1, wherein the PC comprises EPC and the PG comprises EPG.

4. The liposome of claim 1, further comprising at least one antigen.

5. The liposome of claim 4, wherein the antigen comprises a tumor antigen selected from the group consisting of:
   (a) P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, (b) antigenic fragments of any of (a), and (c) mixtures of any of (a) and/or (b).

6. The liposome of claim 4, further comprising at least one adjuvant.

7. The liposome of claim 1, further comprising at least one therapeutic agent or antigen.

8. The liposome of claim 7, wherein the at least one therapeutic agent or antigen is selected from the group consisting of an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments of any of said foregoing antigens, and combinations of any of said therapeutic agents or antigens or antigenic fragments.

9. The liposome of claim 1, having a diameter of about 50 nm to about 150 nm.

10. A composition comprising the liposome of claim 1 and a pharmaceutically acceptable diluent, excipient or carrier.

11. The composition of claim 10, wherein the liposome is present in the composition in an amount of about 1 mg/mL to about 20 mg/mL.

12. The composition of claim 10, wherein the composition is formulated for parenteral, intrathecal, transdermal, rectal, oral, or nasal administration.

13. The composition of claim 10, further comprising at least one therapeutic agent.

14. The composition of claim 13, wherein the therapeutic agent is within the liposome.

15. A method of stimulating an immune response in a mammalian subject comprising administering to the subject the composition of claim 10.

16. The method of claim 15, further comprising administering a therapeutic agent to the mammalian subject.

17. The method of claim 15, wherein the mammalian subject has a cancer.

18. The method of claim 17, further comprising administering to the subject at least one further therapeutic agent, therapy, or antigen selected from the group consisting of a chemotherapeutic agent, a radiotherapeutic agent, radiation therapy, an immune modulator, a Toll-like receptor agonist, a Nod ligand, an anti-viral agent, an antifungal agent, an antibiotic, an antiviral antibody, a cancer immune therapeutic, a chemotherapy agent, a kinase inhibitor, a cytotoxic agent, an anti-asthmatic agent, an antihistamine agent, an anti-inflammatory agent, a vaccine adjuvant, a second liposome, an artificial antigen presenting cell, a cytokine or chemokine blocking antibody, P1A, MUC1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE, antigenic fragments of any of said foregoing antigens, and a combination of any of said therapeutic agents, therapies, antigens or antigenic fragments.

19. The method of claim 15, wherein the subject has an infection caused by an infectious agent selected from the group consisting of a virus, a bacterium, or a parasite.

20. A method of making the liposome of claim 1 comprising:

(a) preparing a stock solution of threitolceramide in an organic solvent;

(b) combining an aliquot of the stock solution with a mixture containing a PC lipid and a PG lipid to form a lipid solution;

(c) diluting the lipid solution with an aqueous solution;

(d) forming multi-lamellar vesicles (MLVs) from the diluted lipid solution; and (e) downsizing the MLVs to about 50 nm to about 150 nm at a temperature above the Tc of the lipids, wherein the threitolceramide is present in an amount of about 3 wt. % to about 12 wt. %, based upon the total weight of the liposome; the PC lipid is present in an amount of about 20 wt. % to about 30 wt. %, based upon the total weight of the liposome; and the PG lipid present in an amount of about 65 wt. % to about 75 wt. %, based upon the total weight of the liposome.

21. The method of claim 15, wherein the subject has an infection caused by a microbe.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Ser Leu Leu Met Trp Ile Thr Gln Cys
1               5
```